United States Patent
Giampietro et al.

(10) Patent No.: US 9,650,372 B2
(45) Date of Patent: May 16, 2017

(54) MOLECULES HAVING PESTICIDAL UTILITY, AND INTERMEDIATES, COMPOSITIONS, AND PROCESSES, RELATED THERETO

(71) Applicant: Dow AgroSciences LLC, Indianapolis, IN (US)

(72) Inventors: Natalie C. Giampietro, Carmel, IN (US); Gary D. Crouse, Noblesville, IN (US); Thomas C. Sparks, Greenfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/241,158

(22) Filed: Aug. 19, 2016

(65) Prior Publication Data
US 2017/0066756 A1 Mar. 9, 2017

Related U.S. Application Data

(60) Provisional application No. 62/214,364, filed on Sep. 4, 2015, provisional application No. 62/214,368, filed on Sep. 4, 2015.

(51) Int. Cl.
*C07D 417/12* (2006.01)
*C07D 249/10* (2006.01)
*A01N 47/02* (2006.01)
*A01N 47/36* (2006.01)
*A01N 43/653* (2006.01)

(52) U.S. Cl.
CPC ......... *C07D 417/12* (2013.01); *A01N 43/653* (2013.01); *A01N 47/02* (2013.01); *A01N 47/36* (2013.01); *C07D 249/10* (2013.01)

(58) Field of Classification Search
CPC .................................................. C07D 417/12
See application file for complete search history.

(56) References Cited

FOREIGN PATENT DOCUMENTS

WO WO-2014/011429 A1 * 1/2014

* cited by examiner

*Primary Examiner* — Laura L. Stockton
(74) *Attorney, Agent, or Firm* — Yung H. Lee

(57) ABSTRACT

This disclosure relates to the field of molecules having pesticidal utility against pests in Phyla Arthropoda, Mollusca, and Nematoda, processes to produce such molecules, intermediates used in such processes, pesticidal compositions containing such molecules, and processes of using such pesticidal compositions against such pests. These pesticidal compositions may be used, for example, as acaricides, insecticides, miticides, molluscicides, and nematicides. This document discloses molecules having the following formula ("Formula One").

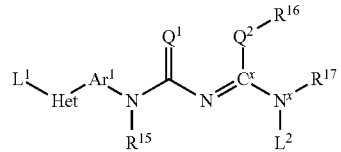

14 Claims, No Drawings

US 9,650,372 B2

MOLECULES HAVING PESTICIDAL UTILITY, AND INTERMEDIATES, COMPOSITIONS, AND PROCESSES, RELATED THERETO

CROSS REFERENCE TO RELATED APPLICATIONS

This application claims priority under 35 U.S.C. §119 of U.S. Provisional Patent Application Ser. No. 62/214,364 and 62/214,368, both filed Sep. 4, 2015, which are hereby incorporated by reference in their entireties.

FIELD OF THIS DISCLOSURE

This disclosure relates to the field of molecules having pesticidal utility against pests in Phyla Arthropoda, Mollusca, and Nematoda, processes to produce such molecules, intermediates used in such processes, pesticidal compositions containing such molecules, and processes of using such pesticidal compositions against such pests. These pesticidal compositions may be used, for example, as acaricides, insecticides, miticides, molluscicides, and nematicides.

BACKGROUND OF THIS DISCLOSURE

"Many of the most dangerous human diseases are transmitted by insect vectors" (Rivero et al.). "Historically, malaria, dengue, yellow fever, plague, filariasis, louse-borne typhus, trypanomiasis, leishmaniasis, and other vector borne diseases were responsible for more human disease and death in the $17^{th}$ through the early $20^{th}$ centuries than all other causes combined" (Gubler). Vector-borne diseases are responsible for about 17% of the global parasitic and infectious diseases. Malaria alone causes over 800,000 deaths a year, 85% of which occur in children under five years of age. Each year there are about 50 to about 100 million cases of dengue fever. A further 250,000 to 500,000 cases of dengue hemorrhagic fever occur each year (Matthews). Vector control plays a critical role in the prevention and control of infectious diseases. However, insecticide resistance, including resistance to multiple insecticides, has arisen in all insect species that are major vectors of human diseases (Rivero et al.). Recently, more than 550 arthropod species have developed resistance to at least one pesticide (Whalon et al.). Furthermore, the cases of insect resistance continue to exceed by far the number of cases of herbicide and fungicide resistance (Sparks et al.).

Each year insects, plant pathogens, and weeds, destroy more than 40% of all food production. This loss occurs despite the application of pesticides and the use of a wide array of non-chemical controls, such as, crop rotations, and biological controls. If just some of this food could be saved, it could be used to feed the more than three billion people in the world who are malnourished (Pimental).

Plant parasitic nematodes are among the most widespread pests, and are frequently one of the most insidious and costly. It has been estimated that losses attributable to nematodes are from about 9% in developed countries to about 15% in undeveloped countries. However, in the United States of America a survey of 35 States on various crops indicated nematode-derived losses of up to 25% (Nicol et al.).

It is noted that gastropods (slugs and snails) are pests of less economic importance than other arthropods or nematodes, but in certain places, they may reduce yields substantially, severely affecting the quality of harvested products, as well as, transmitting human, animal, and plant diseases. While only a few dozen species of gastropods are serious regional pests, a handful of species are important pests on a worldwide scale. In particular, gastropods affect a wide variety of agricultural and horticultural crops, such as, arable, pastoral, and fiber crops; vegetables; bush and tree fruits; herbs; and ornamentals (Speiser).

Termites cause damage to all types of private and public structures, as well as to agricultural and forestry resources. In 2005, it was estimated that termites cause over US $50 billion in damage worldwide each year (Korb).

Consequently, for many reasons, including those mentioned above, there is an on-going need for the costly (estimated to be about US $256 million per pesticide in 2010), time-consuming (on average about 10 years per pesticide), and difficult, development of new pesticides (CropLife America).

CERTAIN REFERENCES CITED IN THIS DISCLOSURE

CropLife America, The Cost of New Agrochemical Product Discovery, Development & Registration, and Research & Development predictions for the Future, 2010.

Drewes, M., Tietjen, K., Sparks, T. C., High-Throughput Screening in Agrochemical Research, *Modern Methods in Crop Protection Research*, Part I, *Methods for the Design and Optimization of New Active Ingredients*, Edited by Jeschke, P., Kramer, W., Schirmer, U., and Matthias W., p. 1-20, 2012.

Gubler, D., Resurgent Vector-Borne Diseases as a Global Health Problem, Emerging Infectious Diseases, Vol. 4, No. 3, p. 442-450, 1998.

Korb, J., Termites, *Current Biology*, Vol. 17, No. 23, 2007.

Matthews, G., Integrated Vector Management: Controlling Vectors of Malaria and Other Insect Vector Borne Diseases, Ch. 1, p. 1, 2011.

Nicol, J., Turner S., Coyne, L., den Nijs, L., Hocksland, L., Tahna-Maafi, Z., Current Nematode Threats to World Agriculture, *Genomic and Molecular Genetics of Plant—Nematode Interactions*, p. 21-43, 2011.

Pimental, D., Pest Control in World Agriculture, *Agricultural Sciences*—Vol. II, 2009.

Rivero, A., Vezilier, J., Weill, M., Read, A., Gandon, S., Insect Control of Vector-Borne Diseases: When is Insect Resistance a Problem? *Public Library of Science Pathogens*, Vol. 6, No. 8, p. 1-9, 2010.

Sparks T. C., Nauen R., IRAC: Mode of action classification and insecticide resistance management, *Pesticide Biochemistry and Physiology* (2014) available online 4 December 2014.

Speiser, B., Molluscicides, *Encyclopedia of Pest Management*, Ch. 219, p. 506-508, 2002.

Whalon, M., Mota-Sanchez, D., Hollingworth, R., Analysis of Global Pesticide Resistance in Arthropods, *Global Pesticide Resistance in Arthropods*, Ch. 1, p. 5-33, 2008.

DEFINITIONS USED IN THIS DISCLOSURE

The examples given in these definitions are generally non-exhaustive and must not be construed as limiting this disclosure. It is understood that a substituent should comply with chemical bonding rules and steric compatibility constraints in relation to the particular molecule to which it is attached. These definitions are only to be used for the purposes of this disclosure.

The phrase "active ingredient" means a material having activity useful in controlling pests, and/or that is useful in helping other materials have better activity in controlling pests, examples of such materials include, but are not limited to, acaricides, algicides, antifeedants, avicides, bactericides, bird repellents, chemosterilants, fungicides, herbicide safeners, herbicides, insect attractants, insect repellents, insecticides, mammal repellents, mating disrupters, molluscicides, nematicides, plant activators, plant growth regulators, rodenticides, synergists, and virucides (see alanwood.net). Specific examples of such materials include, but are not limited to, the materials listed in active ingredient group alpha.

The phrase "active ingredient group alpha" (hereafter "AIGA") means collectively the following materials:

(1) (3-ethoxypropyl)mercury bromide, 1,2-dibromoethane, 1,2-dichloroethane, 1,2-dichloropropane, 1,3-dichloropropene, 1-MCP, 1-methylcyclopropene, 1-naphthol, 2-(octylthio)ethanol, 2,3,3-TPA, 2,3,5-tri-iodobenzoic acid, 2,3,6-TBA, 2,4,5-T, 2,4,5-TB, 2,4,5-TP, 2,4-D, 2,4-DB, 2,4-DEB, 2,4-DEP, 2,4-DES, 2,4-DP, 2,4-MCPA, 2,4-MCPB, 2iP, 2-methoxyethylmercury chloride, 2-phenylphenol, 3,4-DA, 3,4-DB, 3,4-DP, 3,6-dichloropicolinic acid, 4-aminopyridine, 4-CPA, 4-CPB, 4-CPP, 4-hydroxyphenethyl alcohol, 8-hydroxyquinoline sulfate, 8-phenylmercurioxyquinoline, abamectin, abamectin-aminomethyl, abscisic acid, ACC, acephate, acequinocyl, acetamiprid, acethion, acetochlor, acetofenate, acetophos, acetoprole, acibenzolar, aciflurofen, aclonifen, ACN, acrep, acrinathrin, acrolein, acrylonitrile, acypetacs, afidopyropen, afoxolaner, alachlor, alanap, alanycarb, albendazole, aldicarb, aldicarb sulfone, aldimorph, aldoxycarb, aldrin, allethrin, allicin, allidochlor, allosamidin, alloxydim, allyl alcohol, allyxycarb, alorac, alpha-cypermethrin, alpha-endosulfan, alphamethrin, altretamine, aluminium phosphide, aluminum phosphide, ametoctradin, ametridione, ametryn, ametryne, amibuzin, amicarbazone, amicarthiazol, amidithion, amidoflumet, amidosulfuron, aminocarb, aminocyclopyrachlor, aminopyralid, aminotriazole, amiprofos-methyl, amiprophos, amiprophos-methyl, amisulbrom, amiton, amitraz, amitrole, ammonium sulfamate, amobam, amorphous silica gel, amorphous silicon dioxide, ampropylfos, AMS, anabasine, ancymidol, anilazine, anilofos, anisuron, anthraquinone, antu, apholate, aramite, arprocarb, arsenous oxide, asomate, aspirin, asulam, athidathion, atraton, atrazine, aureofungin, avermectin B1, AVG, aviglycine, azaconazole, azadirachtin, azafenidin, azamethiphos, azidithion, azimsulfuron, azinphosethyl, azinphos-ethyl, azinphosmethyl, azinphos-methyl, aziprotryn, aziprotryne, azithiram, azobenzene, azocyclotin, azothoate, azoxystrobin, bachmedesh, barban, barbanate, barium hexafluorosilicate, barium polysulfide, barium silicofluoride, barthrin, basic copper carbonate, basic copper chloride, basic copper sulfate, BCPC, beflubutamid, benalaxyl, benalaxyl-M, benazolin, bencarbazone, benclothiaz, bendaqingbingzhi, bendiocarb, bendioxide, benefin, benfluralin, benfuracarb, benfuresate, benmihuangcaoan, benodanil, benomyl, benoxacor, benoxafos, benquinox, bensulfuron, bensulide, bensultap, bentaluron, bentazon, bentazone, benthiavalicarb, benthiazole, benthiocarb, bentranil, benzadox, benzalkonium chloride, benzamacril, benzamizole, benzamorf, benzene hexachloride, benzfendizone, benzimine, benzipram, benzobicyclon, benzoepin, benzofenap, benzofluor, benzohydroxamic acid, benzomate, benzophosphate, benzothiadiazole, benzovindiflupyr, benzoximate, benzoylprop, benzthiazuron, benzuocaotong, benzyl benzoate, benzyladenine, berberine, beta-cyfluthrin, beta-cypermethrin, bethoxazin, BHC, bialaphos, bicyclopyrone, bifenazate, bifenox, bifenthrin, bifujunzhi, bilanafos, binapacryl, bingqingxiao, bioallethrin, bioethanomethrin, biopermethrin, bioresmethrin, biphenyl, bisazir, bismerthiazol, bismerthiazol-copper, bisphenylmercury methylenedi(x-naphthalene-y-sulphonate), bispyribac, bistrifluron, bisultap, bitertanol, bithionol, bixafen, blasticidin-S, borax, Bordeaux mixture, boric acid, boscalid, BPPS, brassinolide, brassinolide-ethyl, brevicomin, brodifacoum, brofenprox, brofenvalerate, broflanilide, brofluthrinate, bromacil, bromadiolone, bromchlophos, bromethalin, bromethrin, bromfenvinfos, bromoacetamide, bromobonil, bromobutide, bromociclen, bromocyclen, bromo-DDT, bromofenoxim, bromofos, bromomethane, bromophos, bromophos-ethyl, bromopropylate, bromothalonil, bromoxynil, brompyrazon, bromuconazole, bronopol, BRP, BTH, bucarpolate, bufencarb, buminafos, bupirimate, buprofezin, Burgundy mixture, busulfan, busulphan, butacarb, butachlor, butafenacil, butam, butamifos, butane-fipronil, butathiofos, butenachlor, butene-fipronil, butethrin, buthidazole, buthiobate, buthiuron, butifos, butocarboxim, butonate, butopyronoxyl, butoxycarboxim, butralin, butrizol, butroxydim, buturon, butylamine, butylate, butylchlorophos, butylene-fipronil, cacodylic acid, cadusafos, cafenstrole, calciferol, calcium arsenate, calcium chlorate, calcium cyanamide, calcium cyanide, calcium polysulfide, calvinphos, cambendichlor, camphechlor, camphor, captafol, captan, carbam, carbamorph, carbanolate, carbaril, carbaryl, carbasulam, carbathion, carbendazim, carbendazol, carbetamide, carbofenotion, carbofuran, carbon disulfide, carbon tetrachloride, carbonyl sulfide, carbophenothion, carbophos, carbosulfan, carboxazole, carboxide, carboxin, carfentrazone, carpropamid, cartap, carvacrol, carvone, CAVP, CDAA, CDEA, CDEC, cellocidin, CEPC, ceralure, cerenox, cevadilla, Cheshunt mixture, chinalphos, chinalphos-methyl, chinomethionat, chinomethionate, chiralaxyl, chitosan, chlobenthiazone, chlomethoxyfen, chloralose, chloramben, chloramine phosphorus, chloramphenicol, chloraniformethan, chloranil, chloranocryl, chlorantraniliprole, chlorazifop, chlorazine, chlorbenside, chlorbenzuron, chlorbicyclen, chlorbromuron, chlorbufam, chlordane, chlordecone, chlordimeform, chlorempenthrin, chloretazate, chlorethephon, chlorethoxyfos, chloreturon, chlorfenac, chlorfenapyr, chlorfenazole, chlorfenethol, chlorfenidim, chlorfenprop, chlorfenson, chlorfensulphide, chlorfenvinphos, chlorfenvinphos-methyl, chlorfluazuron, chlorflurazole, chlorflurecol, chlorfluren, chlorflurenol, chloridazon, chlorimuron, chlorinate, chlor-IPC, chlormephos, chlormequat, chlormesulone, chlormethoxynil, chlornidine, chlornitrofen, chloroacetic acid, chlorobenzilate, chlorodinitronaphthalenes, chlorofénizon, chloroform, chloromebuform, chloromethiuron, chloroneb, chlorophacinone, chlorophos, chloropicrin, chloropon, chloroprallethrin, chloropropylate, chlorothalonil, chlorotoluron, chloroxifenidim, chloroxuron, chloroxynil, chlorphonium, chlorphoxim, chlorprazophos, chlorprocarb, chlorpropham, chlorpyrifos, chlorpyrifos-methyl, chlorquinox, chlorsulfuron, chlorthal, chlorthiamid, chlorthiophos, chlortoluron, chlozolinate, chltosan, cholecalciferol, choline chloride, chromafenozide, cicloheximide, cimectacarb, cimetacarb, cinerin I, cinerin II, cinerins, cinidon-ethyl, cinmethylin, cinosulfuron, cintofen, ciobutide, cisanilide, cismethrin, clacyfos, clefoxydim, clenpirin, clenpyrin, clethodim, climbazole, cliodinate, clodinafop, cloethocarb, clofencet, clofenotane, clofentezine, clofenvinfos, clofibric acid, clofop, clomazone, clomeprop, clonitralid, cloprop, cloproxydim, clopyralid, cloquintocet, cloransulam, closantel, clothianidin, clotrimazole, cloxyfonac, cloxylacon, clozylacon, CMA, CMMP, CMP, CMU, codlelure, colecalciferol, colophonate, copper 8-quinolinolate, copper acetate, copper acetoarsenite, copper arsenate, copper carbonate, basic, copper hydroxide, copper naphthenate, copper oleate, copper oxychloride, copper silicate, copper sulfate, copper sulfate, basic, copper zinc chromate, coumachlor, coumaféne, coumafos, coumafuryl, coumaphos, coumatetralyl, coumethoxystrobin, coumithoate, coumoxystrobin, CPMC, CPMF, CPPC, credazine, cresol, cresylic acid, crimidine, crotamiton, crotoxyfos, crotoxyphos, crufomate, cryolite, cue-lure, cufraneb, cumyleron, cumyluron, cuprobam, cuprous oxide, curcumenol, CVMP, cyanamide, cyanatryn, cyanazine, cyanofenphos, cyanogen, cyanophos, cyanthoate, cyantraniliprole, cyanuric acid, cyazofamid, cybutryne, cyclafuramid, cyclanilide, cyclaniliprole, cyclethrin, cycloate, cycloheximide, cycloprate, cycloprothrin, cyclopyrimorate, cyclosulfamuron, cycloxydim, cycluron, cyenopyrafen, cyflufenamid, cyflumetofen, cyfluthrin, cyhalodiamide, cyhalofop, cyhalothrin, cyhexatin, cymiazole, cymoxanil, cyometrinil, cypendazole, cypermethrin, cyperquat, cyphenothrin, cyprazine, cyprazole, cyproconazole, cyprodinil, cyprofuram, cypromid, cyprosulfamide, cyromazine, cythioate, cytrex, daimuron, dalapon, daminozide, dayoutong, dazomet, DBCP, d-camphor, DCB, DCIP, DCPA (Japan), DCPA (USA), DCPTA, DCU, DDD, DDPP, DDT, DDVP, debacarb, decafentin, decamethrin, decarbofuran, deet, dehydroacetic acid, deiquat, delachlor, delnav, deltamethrin, demephion, demephion-O, demephion-S, demeton, demeton-methyl, demeton-O, demeton-O-methyl, demeton-S, demeton-S-methyl, demeton-S-methyl sulphone, demeton-S-methylsulphon, DEP, depalléthrine, derris, desmedipham, desmetryn, desmetryne, d-fanshiluquebingjuzhi, diafenthiuron, dialifor, dialifos, diallate, di-allate, diamidafos, dianat, diatomaceous earth, diatomite, diazinon, dibrom, dibutyl phthalate, dibutyl succinate, dicamba, dicapthon, dichlobenil, dichlobentiazox, dichlofenthion, dichlofluanid, dichlone, dichloralurea, dichlorbenzuron, dichlorfenidim, dichlorflurecol, dichlorflurenol, dichlormate, dichlormid, dichloromethane, dichlorophen, dichlorprop, dichlorprop-P, dichlorvos, dichlozolin, dichlozoline, diclobutrazol, diclocymet, diclofop, diclomezine, dicloran, dicloromezotiaz, diclosulam, dicofol, dicophane, dicoumarol, dicresyl, dicrotophos, dicryl, dicumarol, dicyclanil, dicyclonon, dieldrin, dienochlor, diethamquat, diethatyl, diethion, diéthion, diethofencarb, dietholate, diëthon, diethyl pyrocarbonate, diethyltoluamide, difenacoum, difenoconazole, difenopenten, difenoxuron, difenzoquat, difethialone, diflovidazin, diflubenzuron, diflufenican, diflufenicanil, diflufenzopyr, diflumetorim, dikegulac, dilor, dimatif, dimefluthrin, dimefox, dimefuron, dimehypo, dimepiperate, dimetachlone, dimetan, dimethacarb, dimethachlone, dimethachlor, dimethametryn, dimethenamid, dimethenamid-P, dimethipin, dimethirimol, dimethoate, dimethomorph, dimethrin, dimethyl carbate, dimethyl disulfide, dimethyl phthalate, dimethylvinphos, dimetilan, dimexano, dimidazon, dimoxystrobin, dimpylate, dimuron, dinex, dingjunezuo, diniconazole, diniconazole-M, dinitramine, dinitrophenols, dinobuton, dinocap, dinocap-4, dinocap-6, dinocton, dinofenate, dinopenton, dinoprop, dinosam, dinoseb, dinosulfon, dinotefuran, dinoterb, dinoterbon, diofenolan, dioxabenzofos, dioxacarb, dioxathion, dioxation, diphacin, diphacinone, diphenadione, diphenamid, diphenamide, diphenyl sulfone, diphenylamine, diphenylsulphide, diprogulic acid, dipropalin, dipropetryn, dipterex, dipymetitrone, dipyrithione, diquat, disodium tetraborate, disosultap, disparlure, disugran, disul, disulfiram, disulfoton, ditalimfos, dithianon, dithicrofos, dithioether, dithiométon, dithiopyr, diuron, dixanthogen, d-limonene, DMDS, DMPA, DNOC, dodemorph, dodicin, dodine, dofenapyn, doguadine, dominicalure, doramectin, DPC, drazoxolon, DSMA, d-trans-allethrin, d-trans-resmethrin, dufulin, dymron, EBEP, EBP, ebufos, ecdysterone, echlomezol, EDB, EDC, EDDP, edifenphos, eglinazine, emamectin, EMPC, empenthrin, enadenine, endosulfan, endothal, endothall, endothion, endrin, enestroburin, enilconazole, enoxastrobin, ephirsulfonate, EPN, epocholeone, epofenonane, epoxiconazole, eprinomectin, epronaz, epsilon-metofluthrin, epsilon-momfluorothrin, EPTC, erbon, ergocalciferol, erlujixiancaoan, esdépalléthrine, esfenvalerate, ESP, esprocarb, etacelasil, etaconazole, etaphos, etem, ethaboxam, ethachlor, ethalfluralin, ethametsulfuron, ethaprochlor, ethephon, ethidimuron, ethiofencarb, ethiolate, ethion, ethiozin, ethiprole, ethirimol, ethoate-methyl, ethobenzanid, ethofumesate, ethohexadiol, ethoprop, ethoprophos, ethoxyfen, ethoxyquin, ethoxysulfuron, ethychlozate, ethyl formate, ethyl pyrophosphate, ethylan, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, ETM, etnipromid, etobenzanid, etofenprox, etoxazole, etridiazole, etrimfos, étrimphos, eugenol, EXD, famoxadone, famphur, fenac, fenamidone, fenaminosulf, fenaminstrobin, fenamiphos, fenapanil, fenarimol, fenasulam, fenazaflor, fenazaquin, fenbuconazole, fenbutatin oxide, fenchlorazole, fenchlorphos, fenclofos, fenclorim, fenethacarb, fenfluthrin, fenfuram, fenhexamid, fenidin, fenitropan, fenitrothion, fénizon, fenjuntong, fenobucarb, fenolovo, fenoprop, fenothiocarb, fenoxacrim, fenoxanil, fenoxaprop, fenoxaprop-P, fenoxasulfone, fenoxycarb, fenpiclonil, fenpirithrin, fenpropathrin, fenpropidin, fenpropimorph, fenpyrazamine, fenpyroximate, fenquinotrione, fenridazon, fenson, fensulfothion, fenteracol, fenthiaprop, fenthion, fenthion-ethyl, fentiaprop, fentin, fentrazamide, fentrifanil, fenuron, fenuron-TCA, fenvalerate, ferbam, ferimzone, ferric phosphate, ferrous sulfate, fipronil, flamprop, flamprop-M, flazasulfuron, flocoumafen, flometoquin, flonicamid, florasulam, florpyrauxifen, fluacrypyrim, fluazaindolizine, fluazifop, fluazifop-P, fluazinam, fluazolate, fluazuron, flubendiamide, flubenzimine, flubrocythrinate, flucarbazone, flucetosulfuron, fluchloralin, flucofuron, flucycloxuron, flucythrinate, fludioxonil, fluénéthyl, fluenetil, fluensulfone, flufenacet, flufenerim, flufenican, flufenoxuron, flufenoxystrobin, flufenprox, flufenpyr, flufenzine, flufiprole, fluhexafon, flumethrin, flumetover, flumetralin, flumetsulam, flumezin, flumiclorac, flumioxazin, flumipropyn, flumorph, fluometuron, fluopicolide, fluopyram, fluorbenside, fluoridamid, fluoroacetamide, fluoroacetic acid, fluorochloridone, fluorodifen, fluoroglycofen, fluoroimide, fluoromide, fluoromidine, fluoronitrofen, fluoroxypyr, fluothiuron, fluotrimazole, fluoxastrobin, flupoxam, flupropacil, flupropadine, flupropanate, flupyradifurone, flupyrsulfuron, fluquinconazole, fluralaner, flurazole, flurecol, flurenol, fluridone, flurochloridone, fluromidine, fluroxypyr, flurprimidol, flursulamid, flurtamone, flusilazole, flusulfamide, flutenzine, fluthiacet, fluthiamide, flutianil, flutolanil, flutriafol, fluvalinate, fluxametamide, fluxapyroxad, fluxofenim, folpel, folpet, fomesafen, fonofos, foramsulfuron, forchlorfenuron, formaldehyde, formetanate, formothion, formparanate, fosamine, fosetyl, fosmethilan, fospirate, fosthiazate, fosthietan, frontalin, fthalide, fuberidazole, fucaojing, fucaomi, fujunmanzhi, fulumi, fumarin, funaihecaoling, fuphenthiourea, furalane, furalaxyl, furamethrin, furametpyr, furan tebufenozide, furathiocarb, furcarbanil, furconazole, furconazole-cis, furethrin, furfural, furilazole, furmecyclox, furophanate, furyloxyfen, gamma-BHC, gamma-cyhalothrin, gamma-HCH, genit, gibberellic acid, gibberellin A3, gibberellins, gliftor, glitor, glucochloralose, glufosinate, glufosinate-P, glyodin, glyoxime, glyphosate, glyphosine, gossyplure, grandlure, griseofulvin, guanoctine, guazatine, halacrinate, halauxifen, halfenprox, halofenozide, halosafen, halosulfuron, haloxydine, haloxyfop, haloxyfop-P, haloxyfop-R, HCA, HCB, HCH, hemel, hempa, HEOD, heptachlor, heptafluthrin, heptenophos, heptopargil, herbimycin, herbimycin A, heterophos, hexachlor, hexachloran, hexachloroacetone, hexachlorobenzene, hexachlorobutadiene, hexachlorophene, hexaconazole, hexaflumuron, hexafluoramin, hexaflurate, hexalure, hexamide, hexazinone, hexylthiofos, hexythiazox, HHDN, holosulf, homobrassinolide, huancaiwo, huanchongjing, huangcaoling, huanjunzuo, hydramethylnon, hydrargaphen, hydrated lime, hydrogen cyanamide, hydrogen cyanide, hydroprene, hydroxyisoxazole, hymexazol, hyquincarb, IAA, IBA, IBP, icaridin, imazalil, imazamethabenz, imazamox, imazapic, imazapyr, imazaquin, imazethapyr, imazosulfuron, imibenconazole, imicyafos, imidacloprid, imidaclothiz, iminoctadine, imiprothrin, inabenfide, indanofan, indaziflam, indoxacarb, inezin, infusorial earth, iodobonil, iodocarb, iodofenphos, iodomethane, iodosulfuron, iofensulfuron, ioxynil, ipazine, IPC, ipconazole, ipfencarbazone, ipfentrifluconazole, iprobenfos, iprodione, iprovalicarb, iprymidam, ipsdienol, ipsenol, IPSP, IPX, isamidofos, isazofos, isobenzan, isocarbamid, isocarbamide, isocarbophos, isocil, isodrin, isofenphos, isofenphos-methyl, isofetamid, isolan, isomethiozin, isonoruron, isopamphos, isopolinate, isoprocarb, isoprocil, isopropalin, isopropazol, isoprothiolane, isoproturon, isopyrazam, isopyrimol, isothioate, isotianil, isouron, isovaledione, isoxaben, isoxachlortole, isoxadifen, isoxaflutole, isoxapyrifop, isoxathion, isuron, ivermectin, ixoxaben, izopamfos, izopamphos, japonilure, japothrins, jasmolin I, jasmolin II, jasmonic acid, jiahuangchongzong, jiajizengxiaolin, jiaxiangjunzhi, jiecaowan, jiecaoxi, Jinganmycin A, jodfenphos, juvenile hormone I, juvenile hormone II, juvenile hormone III, kadethrin, kappa-bifenthrin, kappa-tefluthrin, karbutilate, karetazan, kasugamycin, kejunlin, kelevan, ketospiradox, kieselguhr, kinetin, kinoprene, kiralaxyl, kresoxim-methyl, kuicaoxi, lactofen, lambda-cyhalothrin, lancotrione, latilure, lead arsenate, lenacil, lepimectin, leptophos, lianbenjingzhi, lime sulfur, lindane, lineatin, linuron, lirimfos, litlure, looplure, lufenuron, lufuqingchongxianan, lüxiancaolin, lvdingjunzhi, lvfumijvzhi, lvxiancaolin, lythidathion, M-74, M-81, MAA, magnesium phosphide, malathion, maldison, maleic hydrazide, malonoben, maltodextrin, MAMA, mancopper, mancozeb, mandestrobin, mandipropamid, maneb, matrine, mazidox, MCC, MCP, MCPA, MCPA-thioethyl, MCPB, MCPP, mebenil, mecarbam, mecarbinzid, mecarphon, mecoprop, mecoprop-P, medimeform, medinoterb, medlure, mefenacet, mefenoxam, mefenpyr, mefentrifluconazole, mefluidide, megatomoic acid, melissyl alcohol, melitoxin, MEMC, menazon, MEP, mepanipyrim, meperfluthrin, mephenate, mephosfolan, mepiquat, mepronil, meptyldinocap, mercaptodimethur, mercaptophos, mercaptophos thiol, mercaptothion, mercuric chloride, mercuric oxide, mercurous chloride, merphos, merphos oxide, mesoprazine, mesosulfuron, mesotrione, mesulfen, mesulfenfos, mesulphen, metacresol, metaflumizone, metalaxyl, metalaxyl-M, metaldehyde, metam, metamifop, metamitron, metaphos, metaxon, metazachlor, metazosulfuron, metazoxolon, metconazole, metepa, metflurazon, methabenzthiazuron, methacrifos, methalpropalin, metham, methamidophos, methasulfocarb, methazole, methfuroxam, methibenzuron, methidathion, methiobencarb, methiocarb, methiopyrisulfuron, methiotepa, methiozolin, methiuron, methocrotophos, métholcarb, methometon, methomyl, methoprene, methoprotryn, methoprotryne, methoquin-butyl, methothrin, methoxychlor, methoxyfenozide, methoxyphenone, methyl apholate, methyl bromide, methyl eugenol, methyl iodide, methyl isothiocyanate, methyl parathion, methylacetophos, methylchloroform, methyldithiocarbamic acid, methyldymron, methylene chloride, methyl-isofenphos, methylmercaptophos, methylmercaptophos oxide, methylmercaptophos thiol, methylmercury benzoate, methylmercury dicyandiamide, methylmercury pentachlorophenoxide, methylneodecanamide, methylnitrophos, methyltriazothion, metiozolin, metiram, metiram-zinc, metobenzuron, metobromuron, metofluthrin, metolachlor, metolcarb, metometuron, metominostrobin, metosulam, metoxadiazone, metoxuron, metrafenone, metriam, metribuzin, metrifonate, metriphonate, metsulfovax, metsulfuron, mevinphos, mexacarbate, miechuwei, mieshuan, miewenjuzhi, milbemectin, milbemycin oxime, milneb, mimanan, mipafox, MIPC, mirex, MNAF, moguchun, molinate, molosultap, momfluorothrin, monalide, monisuron, monoamitraz, monochloroacetic acid, monocrotophos, monolinuron, monomehypo, monosulfiram, monosulfuron, monosultap, monuron, monuron-TCA, morfamquat, moroxydine, morphothion, morzid, moxidectin, MPMC, MSMA, MTMC, muscalure, myclobutanil, myclozolin, myricyl alcohol, N-(ethylmercury)-p-toluenesulphonanilide, NAA, NAAm, nabam, naftalofos, naled, naphthalene, naphthaleneacetamide, naphthalic anhydride, naphthalophos, naphthoxyacetic acids, naphthylacetic acids, naphthylindane-1,3-diones, naphthyloxyacetic acids, naproanilide, napropamide, napropamide-M, naptalam, natamycin, NBPOS, neburea, neburon, nendrin, neonicotine, nichlorfos, niclofen, niclosamide, nicobifen, nicosulfuron, nicotine, nicotine sulfate, nifluridide, nikkomycins, NIP, nipyraclofen, nipyralofen, nitenpyram, nithiazine, nitralin, nitrapyrin, nitrilacarb, nitrofen, nitrofluorfen, nitrostyrene, nitrothal-isopropyl, nobormide, nonanol, norbormide, norea, norflurazon, nornicotine, noruron, novaluron, noviflumuron, NPA, nuarimol, nuranone, OCH, octachlorodipropyl ether, octhilinone, o-dichlorobenzene, ofurace, omethoate, o-phenylphenol, orbencarb, orfralure, orthobencarb, ortho-dichlorobenzene, orthosulfamuron, oryctalure, orysastrobin, oryzalin, osthol, osthole, ostramone, ovatron, ovex, oxabetrinil, oxadiargyl, oxadiazon, oxadixyl, oxamate, oxamyl, oxapyrazon, oxapyrazone, oxasulfuron, oxathiapiprolin, oxaziclomefone, oxinecopper, oxine-Cu, oxolinic acid, oxpoconazole, oxycarboxin, oxydemeton-methyl, oxydeprofos, oxydisulfoton, oxyenadenine, oxyfluorfen, oxymatrine, oxytetracycline, oxythioquinox, PAC, paclobutrazol, paichongding, palléthrine, PAP, para-dichlorobenzene, parafluron, paraquat, parathion, parathion-methyl, parinol, Paris green, PCNB, PCP, PCP-Na, p-dichlorobenzene, PDJ, pebulate, pédinex, pefurazoate, pelargonic acid, penconazole, pencycuron, pendimethalin, penfenate, penflufen, penfluron, penoxalin, penoxsulam, pentachlorophenol, pentachlorophenyl laurate, pentanochlor, penthiopyrad, pentmethrin, pentoxazone, perchlordecone, perfluidone, permethrin, pethoxamid, PHC, phenamacril, phenamacril-ethyl, phénaminosulf, phenazine oxide, phénétacarbe, phenisopham, phenkapton, phenmedipham, phenmedipham-ethyl, phenobenzuron, phenothiol, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosametine, phosazetim, phosazetin, phoscyclotin, phosdiphen, phosethyl, phosfolan, phosfolan-methyl, phosglycin, phosmet, phosnichlor, phosphamide, phosphamidon, phosphine, phosphinothricin, phosphocarb, phosphorus, phostin, phoxim, phoxim-methyl, phthalide, phthalophos, phthalthrin, picarbutrazox, picaridin, picloram, picolinafen, picoxystrobin, pimaricin, pindone, pinoxaden, piperalin, piperazine, piperonyl butoxide, piperonyl cyclonene, piperophos, piproctanly, piproctanyl, piprotal, pirimetaphos, pirimicarb, piriminil, pirimioxyphos, pirimiphos-ethyl, pirimiphos-methyl, pival, pivaldione, plifenate, PMA, PMP, polybutenes, polycarbamate, polychlorcamphene, polyethoxyquinoline, polyoxin D, polyoxins, polyoxorim, polythialan, potassium arsenite, potassium azide, potassium cyanate, potassium ethylxanthate, potassium naphthenate, potassium polysulfide, potassium thiocyanate, pp'-DDT, prallethrin, precocene I, precocene II, precocene III, pretilachlor, primidophos, primisulfuron, probenazole, prochloraz, proclonol, procyazine, procymidone, prodiamine, profenofos, profluazol, profluralin, profluthrin, profoxydim, profurite-aminium, proglinazine, prohexadione, prohydrojasmon, promacyl, promecarb, prometon, prometryn, prometryne, promurit, pronamide, propachlor, propafos, propamidine, propamocarb, propanil, propaphos, propaquizafop, propargite, proparthrin, propazine, propetamphos, propham, propiconazole, propidine, propineb, propisochlor, propoxur, propoxycarbazone, propyl isome, propyrisulfuron, propyzamide, proquinazid, prosuler, prosulfalin, prosulfocarb, prosulfuron, prothidathion, prothiocarb, prothioconazole, prothiofos, prothoate, protrifenbute, proxan, prymidophos, prynachlor, psoralen, psoralene, pydanon, pydiflumetofen, pyflubumide, pymetrozine, pyracarbolid, pyraclofos, pyraclonil, pyraclostrobin, pyraflufen, pyrafluprole, pyramat, pyrametostrobin, pyraoxystrobin, pyrasulfotole, pyraziflumid, pyrazolate, pyrazolynate, pyrazon, pyrazophos, pyrazosulfuron, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridaphenthione, pyridate, pyridinitril, pyrifenox, pyrifluquinazon, pyriftalid, pyrimétaphos, pyrimethanil, pyrimicarbe, pyrimidifen, pyriminobac, pyriminostrobin, pyrimiphos-ethyl, pyrimiphos-methyl, pyrimisulfan, pyrimitate, pyrinuron, pyriofenone, pyriprole, pyripropanol, pyriproxyfen, pyrisoxazole, pyrithiobac, pyrolan, pyroquilon, pyroxasulfone, pyroxsulam, pyroxychlor, pyroxyfur, qincaosuan, qingkuling, quassia, quinacetol, quinalphos, quinalphos-methyl, quinazamid, quinclorac, quinconazole, quinmerac, quinoclamine, quinofumelin, quinomethionate, quinonamid, quinothion, quinoxyfen, quintiofos, quintozene, quizalofop, quizalofop-P, quwenzhi, quyingding, rabenzazole, rafoxanide, R-diniconazole, rebemide, reglone, renriduron, rescalure, resmethrin, rhodethanil, rhodojaponin-III, ribavirin, rimsulfuron, rizazole, R-metalaxyl, rodéthanil, ronnel, rotenone, ryania, sabadilla, saflufenacil, saijunmao, saisentong, salicylanilide, salifluofen, sanguinarine, santonin, S-bioallethrin, schradan, sciliroside, sebuthylazine, secbumeton, sedaxane, selamectin, semiamitraz, sesamex, sesamolin, sesone, sethoxydim, sevin, shuangjiaancaolin, shuangjianancaolin, S-hydroprene, siduron, sifumijvzhi, siglure, silafluofen, silatrane, silica aerogel, silica gel, silthiofam, silthiopham, silthiophan, silvex, simazine, simeconazole, simeton, simetryn, simetryne, sintofen, S-kinoprene, slaked lime, SMA, S-methoprene, S-metolachlor, sodium arsenite, sodium azide, sodium chlorate, sodium cyanide, sodium fluoride, sodium fluoroacetate, sodium hexafluorosilicate, sodium naphthenate, sodium o-phenylphenoxide, sodium orthophenylphenoxide, sodium pentachlorophenate, sodium pentachlorophenoxide, sodium polysulfide, sodium silicofluoride, sodium tetrathiocarbonate, sodium thiocyanate, solan, sophamide, spinetoram, spinosad, spirodiclofen, spiromesifen, spirotetramat, spiroxamine, stirofos, streptomycin, strychnine, sulcatol, sulcofuron, sulcotrione, sulfallate, sulfentrazone, sulfiram, sulfluramid, sulfodiazole, sulfometuron, sulfosate, sulfosulfuron, sulfotep, sulfotepp, sulfoxaflor, sulfoxide, sulfoxime, sulfur, sulfuric acid, sulfuryl fluoride, sulglycapin, sulphosate, sulprofos, sultropen, swep, tau-fluvalinate, tavron, tazimcarb, TBTO, TBZ, TCA, TCBA, TCMTB, TCNB, TDE, tebuconazole, tebufenozide, tebufenpyrad, tebufloquin, tebupirimfos, tebutam, tebuthiuron, tecloftalam, tecnazene, tecoram, tedion, teflubenzuron, tefluthrin, tefuryltrione, tembotrione, temefos, temephos, tepa, TEPP, tepraloxydim, teproloxydim, terallethrin, terbacil, terbucarb, terbuchlor, terbufos, terbumeton, terbuthylazine, terbutol, terbutryn, terbutryne, terraclor, terramicin, terramycin, tetcyclacis, tetrachloroethane, tetrachlorvinphos, tetraconazole, tetradifon, tetradisul, tetrafluron, tetramethrin, tetra methylfluthrin, tetramine, tetranactin, tetraniliprole, tetrapion, tetrasul, thallium sulfate, thallous sulfate, thenylchlor, theta-cypermethrin, thiabendazole, thiacloprid, thiadiazine, thiadifluor, thiamethoxam, thiameturon, thiapronil, thiazafluron, thiazfluron, thiazone, thiazopyr, thicrofos, thicyofen, thidiazimin, thidiazuron, thiencarbazone, thifensulfuron, thifluzamide, thimerosal, thimet, thiobencarb, thiocarboxime, thiochlorfenphim, thiochlorphenphime, thiocyanatodinitrobenzenes, thiocyclam, thiodan, thiodiazole-copper, thiodicarb, thiofanocarb, thiofanox, thiofluoximate, thiohempa, thiomersal, thiometon, thionazin, thiophanate, thiophanate-ethyl, thiophanate-methyl, thiophos, thioquinox, thiosemicarbazide, thiosultap, thiotepa, thioxamyl, thiram, thiuram, thuringiensin, tiabendazole, tiadinil, tiafenacil, tiaojiean, TIBA, tifatol, tiocarbazil, tioclorim, tioxazafen, tioxymid, tirpate, TMTD, tolclofosmethyl, tolfenpyrad, tolprocarb, tolpyralate, tolyfluanid, tolylfluanid, tolylmercury acetate, tomarin, topramezone, toxaphene, TPN, tralkoxydim, tralocythrin, tralomethrin, tralopyril, transfluthrin, transpermethrin, tretamine, triacontanol, triadimefon, triadimenol, triafamone, triallate, triallate, triamiphos, triapenthenol, triarathene, triarimol, triasulfuron, triazamate, triazbutil, triaziflam, triazophos, triazothion, triazoxide, tribasic copper chloride, tribasic copper sulfate, tribenuron, tribufos, tributyltin oxide, tricamba, trichlamide, trichlopyr, trichlorfon, trichlormetaphos-3, trichloronat, trichloronate, trichlorotrinitrobenzenes, trichlorphon, triclopyr, triclopyricarb, tricresol, tricyclazole, tricyclohexyltin hydroxide, tridemorph, tridiphane, trietazine, trifenmorph, trifenofos, trifloxystrobin, trifloxysulfuron, trifludimoxazin, triflumezopyrim, triflumizole, triflumuron, trifluralin, triflusulfuron, trifop, trifopsime, triforine, trihydroxytriazine, trimedlure, trimethacarb, trimeturon, trinexapac, triphenyltin, triprene, tripropindan, triptolide, tritac, trithialan, triticonazole, tritosulfuron, trunc-call, tuoyelin, uniconazole, uniconazole-P, urbacide, uredepa, valerate, validamycin, validamycin A, valifenalate, valone, vamidothion, vangard, vaniliprole, vernolate, vinclozolin, vitamin D3, warfarin, xiaochongliulin, xinjunan, xiwojunan, xiwojunzhi, XMC, xylachlor, xylenols, xylylcarb, xymiazole, yishijing, zarilamid, zeatin, zengxiaoan, zengxiaolin, zeta-cypermethrin, zinc naphthenate, zinc phosphide, zinc thiazole, zinc thiozole, zinc trichlorophenate, zinc trichlorophenoxide, zineb, ziram, zolaprofos, zoocoumarin, zoxamide, zuoanjunzhi, zuocaoan, zuojunzhi, zuomihuanglong, α-chlorohydrin, α-ecdysone, α-multistriatin, α-naphthaleneacetic acids, and β-ecdysone;

(2) the following molecules (a) N-(3-chloro-1-(pyridin-3-yl)-1H-pyrazol-4-yl)-N-ethyl-3-((3,3,3-trifluoropropyl)thio)propanamide (hereafter "AI-1")

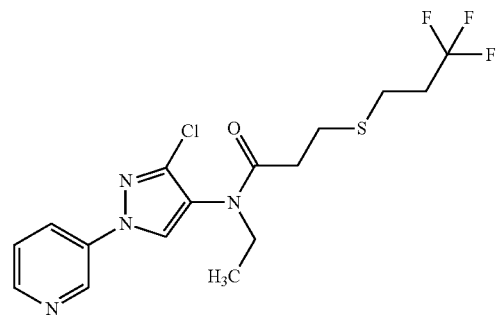 [SMILES: CCN(C(=O)CCSCCC(F)(F)F)c1cn(-c2cccnc2)nc1Cl]

(b) (3S,6S,7R,8R)-8-benzyl-3-(3-((isobutyryloxy)methoxy)-4-methoxypicolinamido)-6-methyl-4,9-dioxo-1,5-dioxonan-7-yl isobutyrate (hereafter "AI-2")

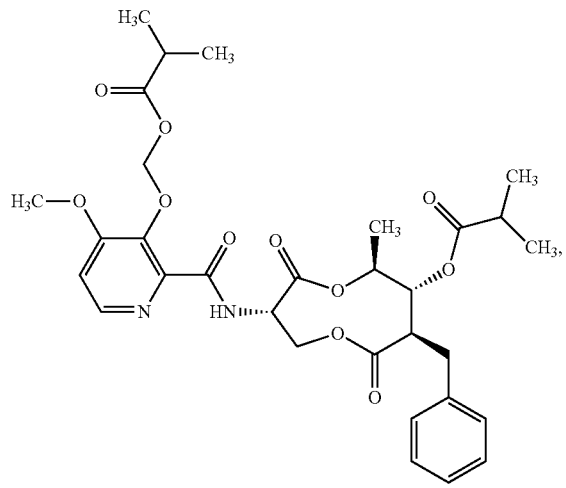 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

(3) a molecule known as Lotilaner that has the following structure

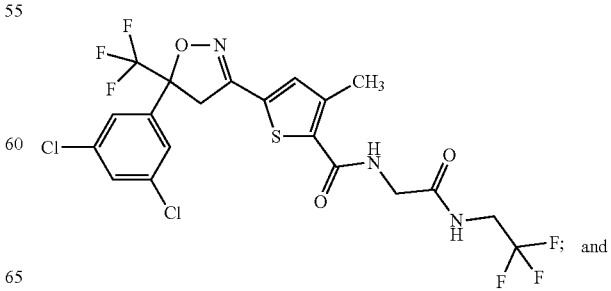

(4) the following molecules in Table A

TABLE A

Structure of M#-active ingredients

| M# | Structure |
|---|---|
| M1 | (structure shown)<br>R = CH, N<br>R₁ = H, Me |
| M2 | (structure shown)<br>X = F, Cl<br>R = H, F |
| M3 | (structure shown) |
| M4 | (structure shown) |
| M5 | (structure shown) |

TABLE A-continued

Structure of M#-active ingredients

| M# | Structure |
|---|---|
| M6 | (structure shown) |

As used in this disclosure, each of the above is an active ingredient. For more information consult the "Compendium of Pesticide Common Names" located at Alanwood.net and various editions, including the on-line edition, of "The Pesticide Manual" located at bcpcdata.com.

A particularly preferred selection of active ingredients are 1,3-dichloropropene, chlorpyrifos, hexaflumuron, methoxyfenozide, noviflumuron, spinetoram, spinosad, sulfoxaflor, and sulfuryl fluoride (hereafter "AIGA-2").

Additionally, another particularly preferred selection of active ingredients are acequinocyl, acetamiprid, acetoprole, avermectin, azinphos-methyl, bifenazate, bifenthrin, carbaryl, carbofuran, chlorfenapyr, chlorfluazuron, chromafenozide, clothianidin, cyfluthrin, cypermethrin, deltamethrin, diafenthiuron, emamectin benzoate, endosulfan, esfenvalerate, ethiprole, etoxazole, fipronil, flonicamid, fluacrypyrim, gamma-cyhalothrin, halofenozide, indoxacarb, lambda-cyhalothrin, lufenuron, malathion, methomyl, novaluron, permethrin, pyridalyl, pyrimidifen, spirodiclofen, tebufenozide, thiacloprid, thiamethoxam, thiodicarb, tolfenpyrad, and zeta-cypermethrin (hereafter "AIGA-3").

The term "alkenyl" means an acyclic, unsaturated (at least one carbon-carbon double bond), branched or unbranched, substituent consisting of carbon and hydrogen, for example, vinyl, allyl, butenyl, pentenyl, and hexenyl.

The term "alkenyloxy" means an alkenyl further consisting of a carbon-oxygen single bond, for example, allyloxy, butenyloxy, pentenyloxy, hexenyloxy.

The term "alkoxy" means an alkyl further consisting of a carbon-oxygen single bond, for example, methoxy, ethoxy, propoxy, isopropoxy, butoxy, isobutoxy, and tert-butoxy.

The term "alkyl" means an acyclic, saturated, branched or unbranched, substituent consisting of carbon and hydrogen, for example, methyl, ethyl, propyl, isopropyl, butyl, and tert-butyl.

The term "alkynyl" means an acyclic, unsaturated (at least one carbon-carbon triple bond), branched or unbranched, substituent consisting of carbon and hydrogen, for example, ethynyl, propargyl, butynyl, and pentynyl.

The term "alkynyloxy" means an alkynyl further consisting of a carbon-oxygen single bond, for example, pentynyloxy, hexynyloxy, heptynyloxy, and octynyloxy.

The term "aryl" means a cyclic, aromatic substituent consisting of hydrogen and carbon, for example, phenyl, naphthyl, and biphenyl.

The term "biopesticide" means a microbial biological pest control agent that, in general, is applied in a similar manner to chemical pesticides. Commonly they are bacterial, but there are also examples of fungal control agents, including *Trichoderma* spp. and *Ampelomyces quisqualis*. One well-known biopesticide example is *Bacillus* species, a bacterial disease of Lepidoptera, Coleoptera, and Diptera. Biopesticides include products based on entomopathogenic fungi (e.g. *Metarhizium anisopliae*), entomopathogenic nematodes (e.g. *Steinernema feltiae*), and entomopathogenic viruses (e.g. *Cydia pomonella* granulovirus). Other examples of entomopathogenic organisms include, but are not limited to, baculoviruses, protozoa, and Microsporidia. For the avoidance of doubt, biopesticides are active ingredients.

The term "cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

The term "cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

The term "cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

The term "cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

The term "halo" means fluoro, chloro, bromo, and iodo.

The term "haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

The term "haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

The term "heterocyclyl" means a cyclic substituent that may be aromatic, fully saturated, or partially or fully unsaturated, where the cyclic structure contains at least one carbon and at least one heteroatom, where said heteroatom is nitrogen, sulfur, or oxygen. Examples are:

(1) aromatic heterocyclyl substituents include, but are not limited to, benzofuranyl, benzoisothiazolyl, benzoisoxazolyl, benzothienyl, benzothiazolyl, benzoxazolyl, cinnolinyl, furanyl, imidazolyl, indazolyl, indolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl;

(2) fully saturated heterocyclyl substituents include, but are not limited to, piperazinyl, piperidinyl, morpholinyl, pyrrolidinyl, tetrahydrofuranyl, and tetrahydropyranyl;

(3) partially or fully unsaturated heterocyclyl substituents include, but are not limited to, 4,5-dihydro-isoxazolyl, 4,5-dihydro-oxazolyl, 4,5-dihydro-1H-pyrazolyl, 2,3-dihydro-[1,3,4]-oxadiazolyl, and 1,2,3,4-tetrahydro-quinolinyl; and (4) Additional examples of heterocyclyls include the following:

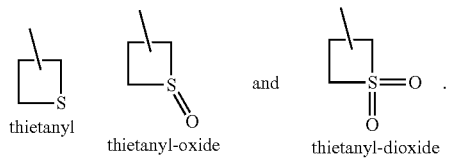

The term "locus" means a habitat, breeding ground, plant, seed, soil, material, or environment, in which a pest is growing, may grow, or may traverse. For example, a locus may be: where crops, trees, fruits, cereals, fodder species, vines, turf, and/or ornamental plants, are growing; where domesticated animals are residing; the interior or exterior surfaces of buildings (such as places where grains are stored); the materials of construction used in buildings (such as impregnated wood); and the soil around buildings.

The phrase "MoA Material" means an active ingredient having a mode of action ("MoA") as indicated in IRAC MoA Classification v. 7.4, located at irac-online.org., which describes the following groups.

(1) Acetylcholinesterase (AChE) inhibitors, includes the following active ingredients acephate, alanycarb, aldicarb, azamethiphos, azinphos-ethyl, azinphos-methyl, bendiocarb, benfuracarb, butocarboxim, butoxycarboxim, cadusafos, carbaryl, carbofuran, carbosulfan, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethiofencarb, ethion, ethoprophos, famphur, fenamiphos, fenitrothion, fenobucarb, fenthion, formetanate, fosthiazate, furathiocarb, heptenophos, imicyafos, isofenphos, isoprocarb, isopropyl O-(methoxyaminothio-phosphoryl)salicylate, isoxathion, malathion, mecarbam, methamidophos, methidathion, methiocarb, methomyl, metolcarb, mevinphos, monocrotophos, Naled, omethoate, oxamyl, oxydemeton-methyl, parathion, parathion-methyl, phenthoate, phorate, phosalone, phosmet, phosphamidon, phoxim, pirimicarb, pirimiphos-methyl, profenofos, propetamphos, propoxur, prothiofos, pyraclofos, pyridaphenthion, quinalphos, sulfotep, tebupirimfos, temephos, terbufos, tetrachlorvinphos, thiodicarb, thiofanox, thiometon, triazamate, triazophos, trichlorfon, trimethacarb, vamidothion, XMC, and xylylcarb.

(2) GABA-gated chloride channel antagonists, includes the following active ingredients chlordane, endosulfan, ethiprole, and fipronil.

(3) Sodium channel modulators, includes the following active ingredients acrinathrin, allethrin, d-cis-trans-allethrin, d-trans-allethrin, bifenthrin, bioallethrin, bioallethrin S-cyclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomers], deltamethrin, empenthrin [(EZ)-(1R)-isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans-isomer], prallethrin, pyrethrins (pyrethrum), resmethrin, silafluofen, tefluthrin, tetramethrin, tetramethrin [(1R)-isomers], tralomethrin, and transfluthrin, and methoxychlor.

(4) Nicotinic acetylcholine receptor (nAChR) agonists, includes the following active ingredients
  (4A) acetamiprid, clothianidin, dinotefuran, imidacloprid, nitenpyram, thiacloprid, thiamethoxam,
  (4B) nicotine,
  (4C) sulfoxaflor,
  (4D) flupyradifurone,
  (4E) triflumezopyrim and dicloromezotiaz.

(5) Nicotinic acetylcholine receptor (nAChR) allosteric activators, includes the following active ingredients spinetoram and spinosad.

(6) Chloride channel activators, includes the following active ingredients abamectin, emamectin benzoate, lepimectin, and milbemectin.

(7) Juvenile hormone mimics, includes the following active ingredients hydroprene, kinoprene, methoprene, fenoxycarb, and pyriproxyfen.

(8) Miscellaneous nonspecific (multi-site) inhibitors, includes the following active ingredients methyl bromide, chloropicrin, sulfuryl fluoride, borax, boric acid, disodium octaborate, sodium borate, sodium metaborate, tartar emetic, diazomet, and metam.

(9) Modulators of Chordotonal Organs, includes the following active ingredients pymetrozine and flonicamid.

(10) Mite growth inhibitors, includes the following active ingredients clofentezine, hexythiazox, diflovidazin, and etoxazole.

(11) Microbial disruptors of insect midgut membranes, includes the following active ingredients *Bacillus thuringiensis* subsp. *israelensis, Bacillus thuringiensis* subsp. *aizawai, Bacillus thuringiensis* subsp. *kurstaki, Bacillus thuringiensis* subsp. *tenebrionenis*, Bt crop proteins (Cry1Ab, Cry1Ac, Cry1Fa, Cry1A.105, Cry2Ab, Vip3A, mCry3A, Cry3Ab, Cry3Bb, Cry34Ab1/Cry35Ab1), and *Bacillus sphaericus.*

(12) Inhibitors of mitochondrial ATP synthase, includes the following active ingredients tetradifon, propargite, azocyclotin, cyhexatin, fenbutatin oxide, and diafenthiuron.

(13) Uncouplers of oxidative phosphorylation via disruption of the proton gradient, includes the following active ingredients chlorfenapyr, DNOC, and sulfluramid.

(14) Nicotinic acetylcholine receptor (nAChR) channel blockers, includes the following active ingredients bensultap, cartap hydrochloride, thiocyclam, and thiosultap-sodium.

(15) Inhibitors of chitin biosynthesis, type 0, includes the following active ingredients bistrifluron, chlorfluazuron, diflubenzuron, flucycloxuron, flufenoxuron, hexaflumuron, lufenuron, novaluron, noviflumuron, teflubenzuron, and triflumuron.

(16) Inhibitors of chitin biosynthesis, type 1, includes the following active ingredient buprofezin.

(17) Moulting disruptor, Dipteran, includes the following active ingredient cyromazine.

(18) Ecdysone receptor agonists, includes the following active ingredients chromafenozide, halofenozide, methoxyfenozide, and tebufenozide.

(19) Octopamine receptor agonists, includes the following active ingredient amitraz.

(20) Mitochondrial complex III electron transport inhibitors, includes the following active ingredients hydramethylnon, acequinocyl, and fluacrypyrim.

(21) Mitochondrial complex I electron transport inhibitors, includes the following active ingredients fenazaquin, fenpyroximate, pyrimidifen, pyridaben, tebufenpyrad, tolfenpyrad, and rotenone.

(22) Voltage-dependent sodium channel blockers, includes the following active ingredients indoxacarb and metaflumizone.

(23) Inhibitors of acetyl CoA carboxylase, includes the following active ingredients spirodiclofen, spiromesifen, and spirotetramat.

(24) Mitochondrial complex IV electron transport inhibitors, includes the following active ingredients, aluminium phosphide, calcium phosphide, phosphine, zinc phosphide, and cyanide.

(25) Mitochondrial complex II electron transport inhibitors, includes the following active ingredients cyenopyrafen, cyflumetofen, and pyflubumide, and

(28) Ryanodine receptor modulators, includes the following active ingredients chlorantraniliprole, cyantraniliprole, and flubendiamide.

Groups 26 and 27 are unassigned in this version of the classification scheme. Additionally, there is a Group UN that contains active ingredients of unknown or uncertain mode of action. This group includes the following active ingredients, azadirachtin, benzoximate, bifenazate, bromopropylate, chinomethionat, cryolite, dicofol, pyridalyl, and pyrifluquinazon.

The term "pest" means an organism that is detrimental to humans, or human concerns (such as, crops, food, livestock, etc.), where said organism is from Phyla Arthropoda, Mollusca, or Nematoda. Particular examples are ants, aphids, bed bugs, beetles, bristletails, caterpillars, cockroaches, crickets, earwigs, fleas, flies, grasshoppers, grubs, hornets, jassids, leafhoppers, lice, locusts, maggots, mealybugs, mites, moths, nematodes, plantbugs, planthoppers, psyllids, sawflies, scales, silverfish, slugs, snails, spiders, springtails, stink bugs, symphylans, termites, thrips, ticks, wasps, whiteflies, and wireworms.

Additional examples are pests in (1) Subphyla Chelicerata, Myriapoda, and Hexapoda.

(2) Classes of Arachnida, Symphyla, and Insecta.

(3) Order Anoplura. A non-exhaustive list of particular genera includes, but is not limited to, *Haematopinus* spp., *Hoplopleura* spp., *Linognathus* spp., *Pediculus* spp., *Polyplax* spp., *Solenopotes* spp., and *Neohaematopinis* spp. A non-exhaustive list of particular species includes, but is not limited to, *Haematopinus asini, Haematopinus suis, Linognathus setosus, Linognathus ovillus, Pediculus humanus capitis, Pediculus humanus humanus*, and *Pthirus pubis*.

(4) Order Coleoptera. A non-exhaustive list of particular genera includes, but is not limited to, *Acanthoscelides* spp., *Agriotes* spp., *Anthonomus* spp., *Apion* spp., *Apogonia* spp., *Araecerus* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Dinoderus* spp., *Gnathocerus* spp., *Hemicoelus* spp., *Heterobostruchus* spp., *Hypera* spp., *Ips* spp., *Lyctus* spp., *Megascelis* spp., *Meligethes* spp., *Mezium* spp., *Niptus* spp., *Otiorhynchus* spp., *Pantomorus* spp., *Phyllophaga* spp., *Phyllotreta* spp., *Ptinus* spp., *Rhizotrogus* spp., *Rhynchites* spp., *Rhynchophorus* spp., *Scolytus* spp., *Sphenophorus* spp., *Sitophilus* spp., *Tenebrio* spp., and *Tribolium* spp. A non-exhaustive list of particular species includes, but is not limited to, *Acanthoscelides obtectus, Agrilus planipennis, Ahasverus advena, Alphitobius diaperinus, Anoplophora glabripennis, Anthonomus grandis, Anthrenus verbasci, Anthrenus falvipes, Ataenius spretulus, Atomaria linearis, Attagenus unicolor, Bothynoderes punctiventris, Bruchus pisorum, Callosobruchus maculatus, Carpophilus hemipterus, Cassida vittata, Cathartus quadricollis, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Euvrilletta peltata, Faustinus cubae, Hylobius pales, Hylotrupes bajulus, Hypera postica, Hypothenemus hampei, Lasioderma serricorne, Leptinotarsa decemlineata, Limonius canus, Liogenys fuscus, Liogenys suturalis, Lissorhoptrus oryzophilus, Lophocateres pusillus, Lyctus planicollis, Maecolaspis joliveti, Melanotus communis, Meligethes aeneus, Melolontha melolontha, Necrobia rufipes, Oberea brevis, Oberea linearis, Oryctes rhinoceros, Oryzaephilus mercator, Oryzaephilus surinamensis, Oulema melanopus, Oulema oryzae, Phyllophaga cuyabana, Polycaon stoutti, Popillia japonica, Prostephanus truncatus, Rhyzopertha dominica, Sitona lineatus, Sitophilus granarius, Sitophilus oryzae, Sitophilus zeamais, Stegobium paniceum, Tenebroides mauritanicus, Tribolium castaneum, Tribolium confusum, Trogoderma granarium, Trogoderma variabile, Xestobium rufovillosum*, and *Zabrus tenebrioides*.

(5) Order Dermaptera. A non-exhaustive list of particular species includes, but is not limited to, *Forficula auricularia*.

(6) Order Blattaria. A non-exhaustive list of particular species includes, but is not limited to, *Blattella germanica, Blattella asahinai, Blatta orientalis, Blatta lateralis, Parcoblatta pennsylvanica, Periplaneta americana, Periplaneta australasiae, Periplaneta brunnea, Periplaneta fuliginosa, Pycnoscelus surinamensis*, and *Supella longipalpa*.

(7) Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Culicoides* spp., *Dasineura* spp., *Delia* spp., *Drosophila* spp., *Fannia* spp., *Hylemya* spp., *Liriomyza* spp., *Musca* spp., *Phorbia* spp., *Pollenia* spp., *Psychoda* spp., *Simulium* spp., *Tabanus* spp., and *Tipula* spp. A non-exhaustive list of particular species includes, but is not limited to, *Agromyza frontella, Anastrepha suspensa, Anastrepha ludens, Anastrepha obliqua, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Liriomyza sativa, Melophagus ovinus, Musca autumnalis, Musca domestica, Oestrus ovis, Oscinella frit, Pegomya betae, Piophila casei, Psila rosae, Rhagoletis cerasi, Rhagoletis pomonella, Rhagoletis mendax, Sitodiplosis mosellana*, and *Stomoxys calcitrans*.

(8) Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Euschistus* spp., *Lepidosaphes* spp., *Lagynotomus* spp., *Lygus* spp., *Macrosiphum* spp., *Nephotettix* spp., *Nezara* spp., *Nilaparvata* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp., and *Unaspis* spp. A non-exhaustive list of particular species includes, but is not limited to, *Acrostemum hilare, Acyrthosiphon pisum, Aleyrodes proletella, Aleurodicus dispersus, Aleurothrixus floccosus, Amrasca biguttula biguttula, Aonidiella aurantii, Aphis fabae, Aphis gossypii, Aphis glycines, Aphis porni, Aulacorthum solani, Bactericera cockerelli, Bagrada hilaris, Bemisia argentifolii, Bemisia tabaci, Blissus leucopterus, Boisea trivittata, Brachycorynella asparagi, Brevennia rehi, Brevicoryne brassicae, Cacopsylla pyri, Cacopsylla pyricola, Calocoris norvegicus, Ceroplastes rubens, Cimex hemipterus, Cimex lectularius, Coccus pseudomagnoliarum, Dagbertus fasciatus, Dichelops furcatus, Diuraphis noxia, Diaphorina citri, Dysaphis plantaginea, Dysdercus suturellus, Edessa meditabunda, Empoasca vitis, Eriosoma lanigerum, Erythroneura elegantula, Eurygaster maura, Euschistus conspersus, Euschistus heros, Euschistus servus, Halyomorpha halys, Helopeltis antonii, Hyalopterus pruni, Helopeltis antonii, Helopeltis theivora, Icerya purchasi, Idioscopus nitidulus, Jacobiasca formosana, Laodelphax striatellus, Lecanium corni, Leptocorisa oratorius, Leptocorisa varicomis, Lygus hesperus, Maconellicoccus hirsutus, Macrosiphum euphorbiae, Macrosiphum granarium, Macrosiphum rosae, Macrosteles quadrilineatus, Mah-anarva frimbiolata, Megacopta cribraria, Metopolophium dirhodum, Mictis longicomis, Myzus persicae, Nasonovia ribisnigri, Nephotettix cincticeps, Neurocolpus longirostris, Nezara viridula, Nilaparvata lugens, Paracoccus marginatus, Paratrioza cockerelli, Parlatoria pergandii, Parlatoria ziziphi, Peregrinus maidis, Phylloxera vitifoliae, Physokermes piceae, Phytocoris califomicus, Phytocoris relativus, Piezodorus guildinii, Planococcus citri, Planococcus ficus, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis*, and *Zulia entrerriana*.

(9) Order Hymenoptera. A non-exhaustive list of particular genera includes, but is not limited to, *Acromyrmex* spp., *Atta* spp., *Camponotus* spp., *Diprion* spp., *Dolichovespula* spp., *Formica* spp., *Monomorium* spp., *Neodiprion* spp., *Paratrechina* spp., *Pheidole* spp., *Pogonomyrmex* spp., *Polistes* spp., *Solenopsis* spp., *Technomyrmex*, spp., *Tetramorium* spp., *Vespula* spp., *Vespa* spp., and *Xylocopa* spp. A non-exhaustive list of particular species includes, but is not limited to, *Athalia rosae, Atta texana, Caliroa cerasi, Cimbex americana, Iridomyrmex humilis, Linepithema humile, Mellifera Scutellata, Monomorium minimum, Monomorium pharaonis, Neodiprion sertifer, Solenopsis invicta, Solenopsis geminata, Solenopsis molesta, Solenopsis richteri, Solenopsis xyloni, Tapinoma sessile*, and *Wasmannia auropunctata*.

(10) Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes acinaciformis, Coptotermes curvignathus, Coptotermes frenchi, Coptotermes formosanus, Coptotermes gestroi, Cryptotermes brevis, Heterotermes aureus, Heterotermes tenuis, Incisitermes minor, Incisitermes snyderi, Microtermes obesi, Nasutitermes corniger, Odontotermes formosanus, Odontotermes obesus, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis*, and *Reticulitermes virginicus*.

(11) Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Nemapogon* spp., *Peridroma* spp., *Phyllonorycter* spp., *Pseudaletia* spp., *Plutella* spp., *Sesamia* spp., *Spodoptera* spp., *Synanthedon* spp., and *Yponomeuta* spp. A non-exhaustive list of particular species includes, but is not limited to, *Achaea Janata, Adoxophyes orana, Agrotis ipsilon, Alabama argillacea, Amorbia*

*cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Corcyra cephalonica, Cossus cossus, Cydia caryana, Cydia funebrana, Cydia molesta, Cydia nigricana, Cydia pomonella, Darna diducta, Diaphania nitidalis, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Estigmene acrea, Eupoecilia ambiguella, Euxoa auxiliaris, Galleria mellonella, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia derkella, Mahasena corbetti, Mamestra brassicae, Manduca sexta, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Phyllonorycter blancardella, Pieris rapae, Plathypena scabra, Platynota idaeusalis, Plodia interpunctella, Plutella xylostella, Polychrosis viteana, Prays endocarpa, Prays oleae, Pseudaletia unipuncta, Pseudoplusia indudens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tinea pellionella, Tineola bisselliella, Trichoplusia ni, Tuta absoluta, Zeuzera coffeae,* and *Zeuzera pyrina.*

(12) Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae,* and *Trichodectes canis.*

(13) Order Orthoptera. A non-exhaustive list of particular genera includes, but is not limited to, *Melanoplus* spp. and *Pterophylla* spp. A non-exhaustive list of particular species includes, but is not limited to, *Acheta domesticus, Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria,* and *Scudderia furcata.*

(14) Order Psocoptera. A non-exhaustive list of particular species includes, but is not limited to, *Liposcelis decolor, Liposcelis entomophila, Lachesilla quercus,* and *Trogium pulsatorium.*

(15) Order Siphonaptera. A non-exhaustive list of particular species includes, but is not limited to, *Ceratophyllus gallinae, Ceratophyllus niger, Ctenocephalides canis, Ctenocephalides felis,* and *Pulex irritans.*

(16) Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular species includes, but is not limited to, *Caliothrips phaseoli, Frankliniella bispinosa, Frankliniella fusca, Frankliniella occidentalis, Frankliniella schultzei, Frankliniella tritici, Frankliniella williamsi, Heliothrips haemorrhoidalis, Rhipiphorothrips cruentatus, Scirtothrips citri, Scirtothrips dorsalis, Taeniothrips rhopalantennalis, Thrips hawaiiensis, Thrips nigropilosus, Thrips orientalis, Thrips palmi,* and *Thrips tabaci.*

(17) Order Thysanura. A non-exhaustive list of particular genera includes, but is not limited to, *Lepisma* spp. and *Thermobia* spp.

(18) Order Acarina. A non-exhaustive list of particular genera includes, but is not limited to, *Acarus* spp., *Aculops* spp., *Argus* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Liponyssoides sanguineus, Notoedres cati, Oligonychus coffeae, Oligonychus ilicis, Ornithonyssus bacoti, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae, Tyrophagus longior,* and *Varroa destructor.*

(19) Order Araneae. A non-exhaustive list of particular genera includes, but is not limited to, *Loxosceles* spp., *Latrodectus* spp., and *Atrax* spp. A non-exhaustive list of particular species includes, but is not limited to, *Loxosceles recluse, Latrodectus mactans,* and *Atrax robustus.*

(20) Class Symphyla. A non-exhaustive list of particular species includes, but is not limited to, *Scutigerella immaculate.*

(21) Subclass Collembola. A non-exhaustive list of particular species includes, but is not limited to, *Bourletiella hortensis, Onychiurus armatus, Onychiurus fimetarius,* and *Sminthurus viridis.*

(22) Phylum Nematoda. A non-exhaustive list of particular genera includes, but is not limited to, *Aphelenchoides* spp., *Belonolaimus* spp., *Criconemella* spp., *Ditylenchus* spp., *Globodera* spp., *Heterodera* spp., *Hirschmanniella* spp., *Hoplolaimus* spp., *Meloidogyne* spp., *Pratylenchus* spp., and *Radopholus* spp. A non-exhaustive list of particular species includes, but is not limited to, *Dirofilaria immitis, Globodera pallida, Heterodera glycines, Heterodera zeae, Meloidogyne incognita, Meloidogyne javanica, Onchocerca volvulus, Pratylenchus penetrans, Radopholus similis,* and *Rotylenchulus reniformis.*

(23) Phylum Mollusca. A non-exhaustive list of particular species includes, but is not limited to, *Arion vulgaris, Cornu aspersum, Deroceras reticulatum, Limax flavus, Milax gagates,* and *Pomacea canaliculata.*

A particularly preferred pest group to control is sap-feeding pests. Sap-feeding pests, in general, have piercing and/or sucking mouthparts and feed on the sap and inner plant tissues of plants. Examples of sap-feeding pests of particular concern to agriculture include, but are not limited to, aphids, leafhoppers, moths, scales, thrips, psyllids, mealybugs, stinkbugs, and whiteflies. Specific examples of Orders that have sap-feeding pests of concern in agriculture include but are not limited to, Anoplura and Hemiptera. Specific examples of Hemiptera that are of concern in agriculture include, but are not limited to, *Aulacaspis* spp., *Aphrophora* spp., *Aphis* spp., *Bemisia* spp., *Coccus* spp., *Euschistus* spp., *Lygus* spp., *Macrosiphum* spp., *Nezara* spp., and *Rhopalosiphum* spp.

Another particularly preferred pest group to control is chewing pests. Chewing pests, in general, have mouthparts that allow them to chew on the plant tissue including roots, stems, leaves, buds, and reproductive tissues (including, but not limited to flowers, fruit, and seeds). Examples of chewing pests of particular concern to agriculture include, but are not limited to, caterpillars, beetles, grasshoppers, and locusts. Specific examples of Orders that have chewing pests of concern in agriculture include but are not limited to, Coleoptera and Lepidoptera. Specific examples of Coleoptera that are of concern in agriculture include, but are not limited to, *Anthonomus* spp., *Cerotoma* spp., *Chaetocnema* spp., *Colaspis* spp., *Cyclocephala* spp., *Diabrotica* spp., *Hypera* spp., *Phyllophaga* spp., *Phyllotreta* spp., *Sphenophorus* spp., *Sitophilus* spp.

The phrase "pesticidally effective amount" means the amount of a pesticide needed to achieve an observable effect on a pest, for example, the effects of necrosis, death, retardation, prevention, removal, destruction, or otherwise diminishing the occurrence and/or activity of a pest in a locus. This effect may come about when pest populations are repulsed from a locus, pests are incapacitated in, or around, a locus, and/or pests are exterminated in, or around, a locus. Of course, a combination of these effects can occur. Generally, pest populations, activity, or both are desirably reduced more than fifty percent, preferably more than 90 percent, and most preferably more than 99 percent. In general, a pesticidally effective amount, for agricultural purposes, is from about 0.0001 grams per hectare to about 5000 grams per hectare, preferably from about 0.0001 grams per hectare to about 500 grams per hectare, and it is even more preferably from about 0.0001 grams per hectare to about 50 grams per hectare.

DETAILED DESCRIPTION OF THIS DISCLOSURE

This document discloses molecules of Formula One

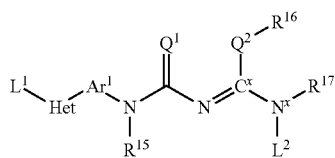

Formula One wherein:

(A) $L^1$ is selected from the group consisting of $(C_1-C_4)$alkyl, $(C_1-C_4)$haloalkyl, $(C_3-C_8)$cycloalkyl, $(C_2-C_6)$alkenyl, $(C_2-C_6)$alkynyl, $(C_1-C_4)$alkyl-O—$(C_1-C_4)$alkyl, and $(C_1-C_4)$alkyl-N($R^x$)—$(C_1-C_4)$alkyl, wherein each alkyl, haloalkyl, cycloalkyl, alkenyl, and alkynyl may be optionally substituted with one or more substituents independently selected from the group consisting of H, F, Cl, Br, I, CN, $NO_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, and $(C_2-C_6)$alkynyl, phenyl, furanyl, pyridazinyl, pyridyl, and thienyl;

wherein each phenyl, furanyl, pyridazinyl, pyridyl, and thienyl may be optionally substituted with one or more substituents independently selected from the group consisting of H, F, Cl, Br, I, CN, $NO_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, $C(O)$—$NR^xR^y$, $(C_1-C_4)$alkyl-$NR^xR^y$, $C(O)$—$(C_1-C_4)$alkyl, $C(O)O$—$(C_1-C_4)$alkyl, $C(O)$—$(C_1-C_4)$haloalkyl, $C(O)O$—$(C_1-C_4)$haloalkyl, $C(O)$—$(C_3-C_8)$cycloalkyl, $C(O)O$—$(C_3-C_8)$cycloalkyl, $C(O)$—$(C_2-C_6)$alkenyl, $C(O)O$—$(C_2-C_6)$alkenyl, $(C_1-C_4)$alkyl-O—$(C_1-C_4)$alkyl, $(C_1-C_4)$alkyl-$S(O)_n$—$(C_1-C_4)$alkyl, $C(O)$—$(C_1-C_4)$alkyl-$C(O)O$—$(C_1-C_4)$alkyl, phenyl, and phenoxy;

(B) Het is a 5- or 6-membered, saturated or unsaturated, heterocyclic ring, containing one or more heteroatoms independently selected from nitrogen, sulfur, or oxygen, and where $L^1$ and $Ar^1$ are not ortho to each other, but may be meta or para, such as, for a five-membered ring they are 1,3, and for a 6-membered ring they are either 1,3 or 1,4, wherein each heterocyclic ring may be optionally substituted with one or more substituents independently selected from the group consisting of H, F, Cl, Br, I, CN, $NO_2$, oxo, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, $C(O)$—$NR^xR^y$, $(C_1-C_4)$alkyl-$NR^xR^y$, $C(O)$—$(C_1-C_4)$alkyl, $C(O)O$—$(C_1-C_4)$alkyl, $C(O)$—$(C_1-C_4)$haloalkyl, $C(O)O$—$(C_1-C_4)$haloalkyl, $C(O)$—$(C_3-C_5)$cycloalkyl, $C(O)O$—$(C_3-C_8)$cycloalkyl, $C(O)$—$(C_2-C_6)$alkenyl, $C(O)O$—$(C_2-C_6)$alkenyl, $(C_1-C_4)$alkyl-O—$(C_1-C_4)$alkyl, $(C_1-C_4)$alkyl-$S(O)_n$—$(C_1-C_4)$alkyl, and $C(O)$—$(C_1-C_4)$alkyl-$C(O)O$—$(C_1-C_4)$alkyl, wherein each alkyl, haloalkyl, cycloalkyl, alkoxy, haloalkoxy, alkenyl, and alkynyl substituent may be optionally substituted with one or more substituents independently selected from the group consisting of H, F, Cl, Br, I, CN, $NO_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, $C(O)$—$NR^xR^y$, $(C_1-C_4)$alkyl-$NR^xR^y$, $C(O)$—$(C_1-C_4)$alkyl, $C(O)O$—$(C_1-C_4)$alkyl, $C(O)$—$(C_1-C_4)$haloalkyl, $C(O)O$—$(C_1-C_4)$haloalkyl, $C(O)$—$(C_3-C_8)$cycloalkyl, $C(O)O$—$(C_3-C_8)$cycloalkyl, $C(O)$—$(C_2-C_6)$alkenyl, $C(O)O$—$(C_2-C_6)$ alkenyl, $(C_1-C_4)$alkyl-O—$(C_1-C_4)$alkyl, $(C_1-C_4)$alkyl-S(O)$_n$—$(C_1-C_4)$alkyl, C(O)—$(C_1-C_4)$alkyl-C(O)O—$(C_1-C_4)$alkyl, phenyl, and phenoxy;

(C) Ar$^1$ is selected from the group consisting of furanyl, phenyl, pyridazinyl, pyridyl, pyrimidinyl, or thienyl, wherein each furanyl, phenyl, pyridazinyl, pyridyl, pyrimidinyl, and thienyl may be optionally substituted with one or more substituents independently selected from the group consisting of H, F, Cl, Br, I, CN, NO$_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, S(O)$_n$—$(C_1-C_4)$alkyl, S(O)$_n$—$(C_1-C_4)$haloalkyl, OSO$_2$—$(C_1-C_4)$alkyl, OSO$_2$—$(C_1-C_4)$haloalkyl, C(O)—NR$^x$R$^y$, $(C_1-C_4)$alkyl-NR$^x$R$^y$, C(O)—$(C_1-C_4)$alkyl, C(O)O—$(C_1-C_4)$alkyl, C(O)—$(C_1-C_4)$haloalkyl, C(O)O—$(C_1-C_4)$haloalkyl, C(O)—$(C_3-C_8)$cycloalkyl, C(O)O—$(C_3-C_8)$cycloalkyl, C(O)—$(C_2-C_6)$alkenyl, C(O)O—$(C_2-C_6)$alkenyl, $(C_1-C_4)$alkyl-O—$(C_1-C_4)$alkyl, $(C_1-C_4)$alkyl-S(O)$_n$—$(C_1-C_4)$alkyl, C(O)—$(C_1-C_4)$alkyl-C(O)O—$(C_1-C_4)$alkyl, phenyl, and phenoxy, wherein each alkyl, haloalkyl, cycloalkyl, alkoxy, haloalkoxy, alkenyl, alkynyl, phenyl, and phenoxy substituent may be optionally substituted with one or more substituents independently selected from the group consisting of H, F, Cl, Br, I, CN, NO$_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, S(O)$_n$—$(C_1-C_4)$alkyl, S(O)$_n$—$(C_1-C_4)$haloalkyl, OSO$_2$—$(C_1-C_4)$alkyl, OSO$_2$—$(C_1-C_4)$haloalkyl, C(O)—NR$^x$R$^y$, $(C_1-C_4)$alkyl-NR$^x$R$^y$, C(O)—$(C_1-C_4)$alkyl, C(O)O—$(C_1-C_4)$alkyl, C(O)—$(C_1-C_4)$haloalkyl, C(O)O—$(C_1-C_4)$haloalkyl, C(O)—$(C_3-C_8)$cycloalkyl, C(O)O—$(C_3-C_8)$cycloalkyl, C(O)—$(C_2-C_6)$alkenyl, C(O)O—$(C_2-C_6)$alkenyl, $(C_1-C_4)$alkyl-O—$(C_1-C_4)$alkyl, $(C_1-C_4)$alkyl-S(O)$_n$—$(C_1-C_4)$alkyl, C(O)—$(C_1-C_4)$alkyl-C(O)O—$(C_1-C_4)$alkyl, phenyl, and phenoxy;

(D) R$^{15}$ is selected from the group consisting of H, $(C_1-C_4)$alkyl, $(C_3-C_8)$cycloalkyl, $(C_2-C_6)$alkenyl, $(C_2-C_6)$alkynyl, S(O)$_n$—$(C_1-C_6)$alkyl, C(O)—NR$^x$R$^y$, C(O)-phenyl, $(C_1-C_6)$alkyl-NR$^x$R$^y$, C(O)O—$(C_1-C_6)$alkyl, C(O)—$(C_3-C_8)$cycloalkyl, C(O)O—$(C_3-C_8)$cycloalkyl, C(O)—$(C_2-C_6)$alkenyl, C(O)O—$(C_2-C_6)$alkenyl, $(C_1-C_4)$alkyl-O—$(C_1-C_4)$alkyl, $(C_1-C_4)$alkyl-OC(O)—$(C_1-C_4)$alkyl, $(C_1-C_4)$alkyl-S(O)$_n$—$(C_1-C_4)$alkyl, $(C_1-C_4)$alkyl-OC(O)O—$(C_1-C_4)$alkyl, wherein each alkyl, cycloalkyl, alkenyl, alkynyl, and phenyl may be optionally substituted with one or more substituents independently selected from the group consisting of H, F, Cl, Br, I, CN, NO$_2$, oxo, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, S(O)$_n$—$(C_1-C_6)$alkyl, S(O)$_n$—$(C_1-C_4)$haloalkyl, OSO$_2$—$(C_1-C_4)$alkyl, OSO$_2$—$(C_1-C_4)$haloalkyl, C(O)—NR$^x$R$^y$, $(C_1-C_4)$alkyl-NR$^x$R$^y$, C(O)—$(C_1-C_4)$alkyl, C(O)O—$(C_1-C_4)$alkyl, C(O)—$(C_1-C_4)$haloalkyl, C(O)O—$(C_1-C_4)$haloalkyl, C(O)—$(C_3-C_8)$cycloalkyl, C(O)O—$(C_3-C_8)$cycloalkyl, C(O)—$(C_2-C_6)$alkenyl, C(O)O—$(C_2-C_6)$alkenyl, $(C_1-C_4)$alkyl-O—$(C_1-C_4)$alkyl, $(C_1-C_4)$alkyl-S(O)$_n$—$(C_1-C_4)$alkyl, C(O)—$(C_1-C_4)$alkyl-C(O)O—$(C_1-C_4)$alkyl, phenyl, and phenoxy;

(E) Q$^1$ is selected from the group consisting of O and S;

(F) Q$^2$ is selected from the group consisting of O and S;

(G) R$^{16}$ is selected from the group consisting of (J), H, $(C_1-C_4)$alkyl, $(C_3-C_8)$cycloalkyl, $(C_2-C_6)$alkenyl, $(C_2-C_6)$alkynyl, C(O)—$(C_1-C_4)$alkyl, $(C_1-C_4)$alkyl-O—$(C_1-C_4)$alkyl, $(C_1-C_4)$alkyl-S(O)$_n$—$(C_1-C_4)$alkyl, $(C_1-C_4)$alkylphenyl, $(C_1-C_4)$alkyl-O-phenyl, C(O)-(Het-1), Het-1, $(C_1-C_4)$alkyl-(Het-1), $(C_1-C_4)$alkyl-OC(O)—$(C_1-C_4)$alkyl, $(C_1-C_4)$alkyl-OC(O)—$(C_1-C_4)$alkyl, $(C_1-C_4)$alkyl-OC(O)O—$(C_1-C_4)$alkyl, $(C_1-C_4)$alkyl-OC(O)—NR$^x$R$^y$, $(C_1-C_4)$alkyl-C(O)—N(R$^x$)($C_1-C_4$)alkyl-(Het-1), $(C_1-C_4)$alkyl-C(O)-(Het-1), $(C_1-C_4)$alkyl-C(O)—N(R$^x$)($C_1-C_4$)alkyl(NR$^x$R$^y$)—C(O)OH, $(C_1-C_4)$alkyl-C(O)—N(R$^x$)($C_1-C_4$)alkyl-NR$^x$R$^y$, $(C_1-C_4)$alkyl-C(O)—N(R$^x$)($C_1-C_4$)alkyl-N(R$^x$)—C(O)O—$(C_1-C_4)$alkyl, $(C_1-C_4)$alkyl-C(O)—N(R$^x$)($C_1-C_4$)alkyl(N(R$^x$)—C(O)O—$(C_1-C_4)$alkyl)-C(O)OH, $(C_1-C_4)$alkyl-C(O)-(Het-1)-C(O)O—$(C_1-C_4)$alkyl, $(C_1-C_4)$alkyl-OC(O)O—$(C_1-C_4)$alkyl, $(C_1-C_4)$alkyl-OC(O)—$(C_1-C_4)$alkyl, $(C_1-C_4)$alkyl-OC(O)—$(C_3-C_8)$cycloalkyl, $(C_1-C_4)$alkyl-OC(O)-(Het-1), $(C_1-C_4)$alkyl-OC(O)—$(C_1-C_4)$alkyl-N(R$^x$)—C(O)O—$(C_1-C_4)$alkyl, $(C_1-C_4)$alkyl-NR$^x$R$^y$, $(C_1-C_4)$alkyl-S(O)$_n$-(Het-1), and $(C_1-C_4)$alkyl-O-(Het-1), wherein each alkyl, cycloalkyl, alkenyl, alkynyl, phenyl, and (Het-1) may be optionally substituted with one or more substituents independently selected from the group consisting of H, F, Cl, Br, I, CN, NO$_2$, NR$^x$R$^y$, $(C_1-C_4)$alkyl, $(C_1-C_4)$haloalkyl, $(C_3-C_8)$cycloalkyl, $(C_1-C_4)$alkoxy, $(C_2-C_6)$alkenyl, $(C_2-C_6)$alkynyl, S(O)$_n$—$(C_1-C_4)$alkyl, S(O)$_n$—$(C_1-C_4)$haloalkyl, OSO$_2$—$(C_1-C_4)$alkyl, OSO$_2$—$(C_1-C_4)$haloalkyl, C(O)H, C(O)OH, C(O)—NR$^x$R$^y$, $(C_1-C_4)$alkyl-NR$^x$R$^y$, C(O)—$(C_1-C_4)$alkyl, C(O)O—$(C_1-C_4)$alkyl, C(O)—$(C_1-C_4)$haloalkyl, C(O)O—$(C_1-C_4)$haloalkyl, C(O)—$(C_3-C_8)$cycloalkyl, C(O)O—$(C_3-C_8)$cycloalkyl, C(O)—$(C_2-C_6)$alkenyl, C(O)O—$(C_2-C_6)$alkenyl, $(C_1-C_4)$alkyl-O—$(C_1-C_4)$alkyl, $(C_1-C_4)$alkyl-S(O)$_n$—$(C_1-C_4)$alkyl, C(O)—$(C_1-C_4)$alkyl-C(O)O—$(C_1-C_4)$alkyl), phenyl, phenoxy, Si(($(C_1-C_4)$alkyl)$_3$, S(O)$_n$—NR$^x$R$^y$, and (Het-1);

(H) R$^{17}$ is selected from the group consisting of (J), H, $(C_1-C_4)$alkyl, $(C_3-C_8)$cycloalkyl, $(C_2-C_6)$alkenyl, $(C_2-C_6)$alkynyl, C(O)—$(C_1-C_4)$alkyl, $(C_1-C_4)$alkyl-O—$(C_1-C_4)$alkyl, $(C_1-C_4)$alkyl-S(O)$_n$—$(C_1-C_4)$alkyl, $(C_1-C_4)$alkylphenyl, $(C_1-C_4)$alkyl-O-phenyl, C(O)-(Het-1), Het-1, $(C_1-C_4)$alkyl-(Het-1), $(C_1-C_4)$alkyl-OC(O)—$(C_1-C_4)$alkyl, $(C_1-C_4)$alkyl-OC(O)—$(C_1-C_4)$alkyl, $(C_1-C_4)$alkyl-OC(O)O—$(C_1-C_4)$alkyl, $(C_1-C_4)$alkyl-OC(O)—NR$^x$R$^y$, $(C_1-C_4)$alkyl-C(O)—N(R$^x$)($C_1-C_4$)alkyl-(Het-1), $(C_1-C_4)$alkyl-C(O)-(Het-1), $(C_1-C_4)$alkyl-C(O)—N(R$^x$)($C_1-C_4$)alkyl(NR$^x$R$^y$)—C(O)OH, $(C_1-C_4)$alkyl-C(O)—N(R$^x$)($C_1-C_4$)alkyl-NR$^x$R$^y$, $(C_1-C_4)$alkyl-C(O)—N(R$^x$)($C_1-C_4$)alkyl-N(R$^x$)—C(O)O—$(C_1-C_4)$alkyl, $(C_1-C_4)$alkyl-C(O)—N(R$^x$)($C_1-C_4$)alkyl(N(R$^x$)—C(O)O—$(C_1-C_4)$alkyl)-C(O)OH, $(C_1-C_4)$alkyl-C(O)-(Het-1)-C(O)O—$(C_1-C_4)$alkyl, $(C_1-C_4)$alkyl-OC(O)O—$(C_1-C_4)$alkyl, $(C_1-C_4)$alkyl-OC(O)—$(C_1-C_4)$alkyl, $(C_1-C_4)$alkyl-OC(O)—$(C_3-C_8)$cycloalkyl, $(C_1-C_4)$alkyl-OC(O)-(Het-1), $(C_1-C_4)$alkyl-OC(O)—$(C_1-C_4)$alkyl-N(R$^x$)—C(O)O—$(C_1-C_4)$alkyl, $(C_1-C_4)$alkyl-NR$^x$R$^y$, $(C_1-C_4)$alkyl-S(O)$_n$-(Het-1), and $(C_1-C_4)$alkyl-O-(Het-1), wherein each alkyl, cycloalkyl, alkenyl, alkynyl, phenyl, and (Het-1) may be optionally substituted with one or more substituents independently selected from the group consisting of H, F, Cl, Br, I, CN, $NO_2$, $NR^xR^y$, $(C_1-C_4)$alkyl, $(C_1-C_4)$haloalkyl, $(C_3-C_8)$cycloalkyl, $(C_1-C_4)$alkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, C(O)H, C(O)OH, C(O)—$NR^xR^y$, $(C_1-C_4)$alkyl-$NR^xR^y$, C(O)—$(C_1-C_4)$alkyl, C(O)O—$(C_1-C_4)$alkyl, C(O)—$(C_1-C_4)$haloalkyl, C(O)O—$(C_1-C_4)$haloalkyl, C(O)—$(C_3-C_8)$cycloalkyl, C(O)O—$(C_3-C_8)$cycloalkyl, C(O)—$(C_2-C_6)$alkenyl, C(O)O—$(C_2-C_6)$alkenyl, $(C_1-C_4)$alkyl-O—$(C_1-C_4)$alkyl, $(C_1-C_4)$alkyl-$S(O)_n$—$(C_1-C_4)$alkyl, C(O)—$(C_1-C_4)$alkyl-C(O)O—$(C_1-C_4)$alkyl, phenyl, phenoxy, $Si((C_1-C_4)alkyl)_3$, $S(O)_n$—$NR^xR^y$, and (Het-1);

(I) $L^2$ is selected from the group consisting of $(C_3-C_8)$cycloalkyl, phenyl, $(C_1-C_4)$alkylphenyl, $(C_1-C_4)$alkyl-O-phenyl, $(C_2-C_6)$alkenyl-O-phenyl, (Het-1), $(C_1-C_4)$alkyl-(Het-1), and $(C_1-C_4)$alkyl-O-(Het-1),
wherein each alkyl, cycloalkyl, alkenyl, phenyl, and (Het-1) may be optionally substituted with one or more substituents independently selected from the group consisting of H, F, Cl, Br, I, CN, $NO_2$, $NR^xR^y$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, C(O)H, C(O)—$NR^xR^y$, $(C_1-C_4)$alkyl-$NR^xR^y$, C(O)—$(C_1-C_4)$alkyl, C(O)O—$(C_1-C_4)$alkyl, C(O)—$(C_1-C_4)$haloalkyl, C(O)O—$(C_1-C_4)$haloalkyl, C(O)—$(C_3-C_8)$cycloalkyl, C(O)O—$(C_1-C_4)$cycloalkyl, C(O)—$(C_2-C_6)$alkenyl, C(O)O—$(C_2-C_6)$alkenyl, O—$(C_1-C_4)$alkyl, S—$(C_1-C_4)$alkyl, $(C_1-C_4)$alkyl-O—$(C_1-C_4)$alkyl, C(O)—$(C_1-C_4)$alkyl-C(O)O—$(C_1-C_4)$alkyl, phenyl, phenoxy, and (Het-1),
wherein each alkyl, cycloalkyl, alkenyl, phenyl, and (Het-1) substituent may be optionally substituted with one or more substituents independently selected from the group consisting of H, F, Cl, Br, I, CN, $NO_2$, $NR^xR^y$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, C(O)H, C(O)—$NR^xR^y$, $(C_1-C_4)$alkyl-$NR^xR^y$, C(O)—$(C_1-C_4)$alkyl, C(O)O—$(C_1-C_4)$alkyl, C(O)—$(C_1-C_4)$haloalkyl, C(O)O—$(C_1-C_4)$haloalkyl, C(O)—$(C_3-C_8)$cycloalkyl, C(O)O—$(C_1-C_4)$cycloalkyl, C(O)—$(C_2-C_6)$alkenyl, C(O)O—$(C_2-C_6)$alkenyl, O—$(C_1-C_4)$alkyl, S—$(C_1-C_4)$alkyl, $(C_1-C_4)$alkyl-O—$(C_1-C_4)$alkyl, C(O)—$(C_1-C_4)$alkyl-C(O)O—$(C_1-C_4)$alkyl, phenyl, phenoxy, and (Het-1);

(J) $R^{16}$ and $R^{17}$ along with $C^x(Q^2)(N^x)$, form a 4- to 7-membered saturated or unsaturated, hydrocarbyl cyclic group, which may further contain one or more heteroatoms selected from the group consisting of nitrogen, sulfur, and oxygen,
wherein said hydrocarbyl cyclic group may be optionally substituted with one or more substituents independently selected from the group consisting of oxo, $R^{18}$, and $R^{19}$, wherein $R^{18}$ and $R^{19}$ are each independently selected from the group consisting of H, F, Cl, Br, I, CN, $NO_2$, oxo, thioxo, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, C(O)H, C(O)—$(C_1-C_4)$alkyl, C(O)O—$(C_1-C_4)$alkyl, C(O)—$(C_1-C_4)$haloalkyl, C(O)O—$(C_1-C_4)$haloalkyl, C(O)—$(C_3-C_8)$cycloalkyl, C(O)O—$(C_3-C_8)$cycloalkyl, C(O)—$(C_2-C_6)$alkenyl, C(O)O—$(C_2-C_6)$alkenyl, $(C_1-C_4)$alkyl-O—$(C_1-C_4)$alkyl, $(C_1-C_4)$alkyl-$S(O)_n$—$(C_1-C_4)$alkyl, C(O)—$(C_1-C_4)$alkyl-C(O)O—$(C_1-C_4)$alkyl, phenyl, and (Het-1);

(K) $R^x$ and $R^y$ are each independently selected from the group consisting of H, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, C(O)H, C(O)—$(C_1-C_4)$alkyl, C(O)O—$(C_1-C_4)$alkyl, C(O)—$(C_1-C_4)$haloalkyl, C(O)O—$(C_1-C_4)$haloalkyl, C(O)—$(C_3-C_8)$cycloalkyl, C(O)O—$(C_3-C_8)$cycloalkyl, C(O)—$(C_2-C_6)$alkenyl, C(O)O—$(C_2-C_6)$alkenyl, $(C_1-C_4)$alkyl-O—$(C_1-C_4)$alkyl, $(C_1-C_4)$alkyl-$S(O)_n$—$(C_1-C_4)$alkyl, C(O)—$(C_1-C_4)$alkyl-C(O)O—$(C_1-C_4)$alkyl, and phenyl,
wherein each alkyl, haloalkyl, cycloalkyl, alkoxy, haloalkoxy, alkenyl, alkynyl, and phenyl may be optionally substituted with one or more substituents independently selected from the group consisting of H, F, Cl, Br, I, CN, $NO_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, C(O)H, C(O)—$(C_1-C_4)$alkyl, C(O)O—$(C_1-C_4)$alkyl, C(O)—$(C_1-C_4)$haloalkyl, C(O)O—$(C_1-C_4)$haloalkyl, C(O)—$(C_3-C_8)$cycloalkyl, C(O)O—$(C_3-C_8)$cycloalkyl, C(O)—$(C_2-C_6)$alkenyl, C(O)O—$(C_2-C_6)$alkenyl, $(C_1-C_4)$alkyl-O—$(C_1-C_4)$alkyl, $(C_1-C_4)$alkyl-$S(O)_n$—$(C_1-C_4)$alkyl, C(O)—$(C_1-C_4)$alkyl-C(O)O—$(C_1-C_4)$alkyl, phenyl, and (Het-1);

(L) (Het-1) is a 5- or 6-membered, saturated or unsaturated, heterocyclic ring, containing one or more heteroatoms independently selected from nitrogen, sulfur, or oxygen,
wherein each heterocyclic ring may be optionally substituted with one or more substituents independently selected from the group consisting of H, F, Cl, Br, I, CN, $NO_2$, oxo, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, C(O)—$NR^xR^y$, $(C_1-C_4)$alkyl-$NR^xR^y$, C(O)—$(C_1-C_4)$alkyl, C(O)O—$(C_1-C_4)$alkyl, C(O)—$(C_1-C_4)$haloalkyl, C(O)O—$(C_1-C_4)$haloalkyl, C(O)—$(C_3-C_8)$cycloalkyl, C(O)O—$(C_3-C_8)$cycloalkyl, C(O)—$(C_2-C_6)$alkenyl, C(O)O—$(C_2-C_6)$alkenyl, $(C_1-C_4)$alkyl-O—$(C_1-C_4)$alkyl, $(C_1-C_4)$alkyl-$S(O)_n$—$(C_1-C_4)$alkyl, C(O)—$(C_1-C_4)$alkyl-C(O)O—$(C_1-C_4)$alkyl, phenyl, and phenoxy,
wherein each alkyl, haloalkyl, cycloalkyl, alkoxy, haloalkoxy, alkenyl, alkynyl, phenyl, and phenoxy substituent may be optionally substituted with one or more substituents independently selected from the group consisting of H, F, Cl, Br, I, CN, $NO_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, C(O)—$NR^xR^y$, $(C_1-C_4)$alkyl-$NR^xR^y$, C(O)—$(C_1-C_4)$alkyl, C(O)O—$(C_1-C_4)$alkyl, C(O)—$(C_1-C_4)$haloalkyl, C(O)O—$(C_1-C_4)$haloalkyl, C(O)—$(C_3-C_8)$cycloalkyl, C(O)O—$(C_3-C_8)$cycloalkyl, C(O)—$(C_2-C_6)$alkenyl, C(O)O—$(C_2-C_6)$alkenyl, $(C_1-C_4)$alkyl-O—$(C_1-C_4)$alkyl, $(C_1-C_4)$alkyl-$S(O)_n$—$(C_1-C_4)$alkyl, C(O)—$(C_1-C_4)$alkyl-C(O)O—$(C_1-C_4)$alkyl, phenyl, and phenoxy;

(M) n are each independently 0, 1, or 2; and

N-oxides, agriculturally acceptable acid addition salts, salt derivatives, solvates, crystal polymorphs, isotopes, resolved stereoisomers, and tautomers, of the molecules of Formula One.

The molecules of Formula One may exist in different geometric or optical isomeric or different tautomeric forms. One or more centers of chirality may be present in which case molecules of Formula One may be present as pure enantiomers, mixtures of enantiomers, pure diastereomers or mixtures of diastereomers. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. There may be double bonds present in the molecule, in which case compounds of Formula One may exist as single geometric isomers (cis or trans, E or Z) or mixtures of geometric isomers (cis and trans, E and Z). Centers of tautomerisation may be present. This disclosure covers all such isomers, tautomers, and mixtures thereof, in all proportions. The structures disclosed in the present disclosure are drawn in only one geometric form for clarity, but are intended to represent all geometric forms of the molecule.

In another embodiment $L^1$ is selected from the group consisting of,

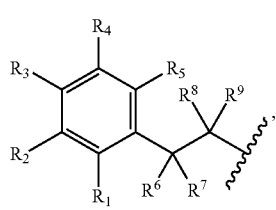
(1a)

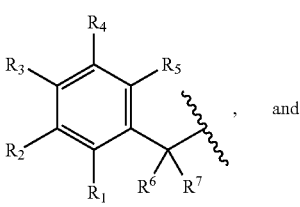
(1b)

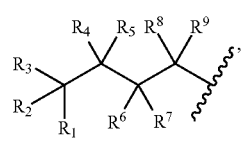
(1c)

wherein, $R^1$, $R^2$, $R^3$, $R^4$, $R^5$, $R^6$, $R^7$, $R^8$, $R^9$ are each one or more substituents independently selected from the group consisting of H, F, $(C_1-C_4)$haloalkyl, and $(C_1-C_4)$haloalkoxy. This embodiment may be used in combination with the other embodiments of Het, $Ar^1$, $R^{18}$, $Q^1$, $Q^2$, $R^{16}$, $R^{17}$, and $L^2$.

In another embodiment $L^1$ is (1a), (1b), or (1c), wherein are $R^3$ is $CF_3$ or $OCF_3$. This embodiment may be used in combination with the other embodiments of $R^1$, $R^2$, $R^4$, $R^5$, $R^6$, $R^7$, $R^8$, $R^9$, Het, $Ar^1$, $R^{15}$, $Q^1$, $Q^2$, $R^{16}$, $R^{17}$, and $L^2$.

In another embodiment Het is (1d)

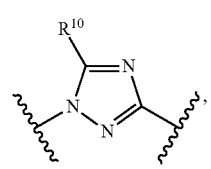
(1d)

wherein, $R^{10}$ is H. This embodiment may be used in combination with the other embodiments of $L^1$, $Ar^1$, $R^{18}$, $Q^1$, $Q^2$, $R^{16}$, $R^{17}$, and $L^2$.

In another embodiment $Ar^1$ is (1e)

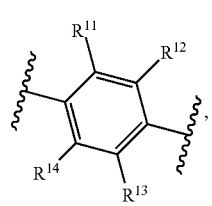
(1e)

wherein, $R^{11}$, $R^{12}$, $R^{13}$, and $R^{14}$ are each independently H. This embodiment may be used in combination with the other embodiments of $L^1$, Het, $R^{15}$, $Q^1$, $Q^2$, $R^{16}$, $R^{17}$, and $L^2$.

In another embodiment $R^{15}$ is H. This embodiment may be used in combination with the other embodiments of $L^1$, Het, $Ar^1$, $Q^1$, $Q^2$, $R^{16}$, $R^{17}$, and $L^2$.

In another embodiment $Q^1$ is O. This embodiment may be used in combination with the other embodiments of $L^1$, Het, $Ar^1$, $R^{15}$, $Q^2$, $R^{16}$, $R^{17}$, and $L^2$.

In another embodiment $Q^2$ is S. This embodiment may be used in combination with the other embodiments of $L^1$, Het, $Ar^1$, $R^{15}$, $Q^1$, $R^{16}$, $R^{17}$, and $L^2$.

In another embodiment $L^2$ is (1f)

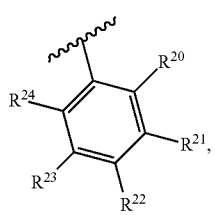
(1f)

wherein:
(1) $R^{20}$ is $(C_1-C_4)$alkyl;
(2) $R^{21}$, $R^{22}$, and $R^{24}$ are each independently H; and
(3) $R^{23}$ is $(C_1-C_4)$alkyl.

This embodiment may be used in combination with the other embodiments of $L^1$, Het, $Ar^1$, $R^{15}$, $Q^1$, $Q^2$, $R^{16}$, and $R^{17}$.

In another embodiment $L^2$ is (1f), wherein $R^{20}$ is $CH(CH_3)_2$. This embodiment may be used in combination with the other embodiments of $L^1$, Het, $Ar^1$, $Q^1$, $Q^2$, $R^{16}$, $R^{17}$, $R^{21}$, $R^{22}$, $R^{23}$, and $R^{24}$.

In another embodiment $L^2$ is (1f), wherein $R^{23}$ is $CH_3$. This embodiment may be used in combination with the other embodiments of $L^1$, Het, $Ar^1$, $Q^1$, $Q^2$, $R^{16}$, $R^{17}$, $R^{20}$, $R^{21}$, $R^{22}$, and $R^{24}$.

In another embodiment $R^{16}$ and $R^{17}$ along with $C^x(Q^2)(N^x)$, is (1g)

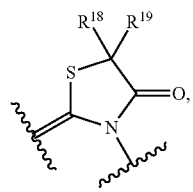
(1g)

wherein, $R^{18}$ and $R^{19}$ are each independently H. This embodiment may be used in combination with the other embodiments of $L^1$, Het, $Ar^1$, $R^{15}$, $Q^1$, and $L^2$.

In another embodiment
(A) $L^1$ is selected from the group consisting of

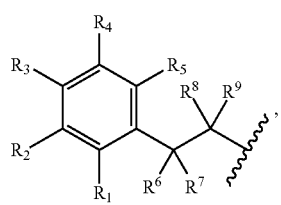
(1a)

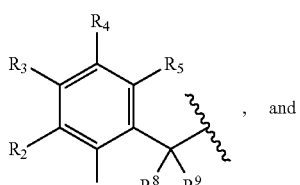
(1b), and

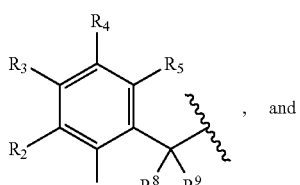

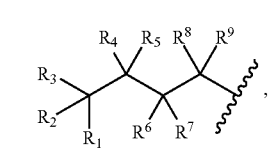
(1c)

wherein, $R^1$, $R^2$, $R^3$, $R^4$, $R^5$, $R^6$, $R^7$, $R^8$, $R^9$ are each independently selected from the group consisting of H, F, Cl, Br, I, CN, $NO_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, and $(C_2-C_6)$alkynyl, phenyl, furanyl, pyridazinyl, pyridyl, and thienyl;

wherein each phenyl, furanyl, pyridazinyl, pyridyl, and thienyl may be optionally substituted with one or more substituents independently selected from the group consisting of H, F, Cl, Br, I, CN, $NO_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, $C(O)$—$NR^xR^y$, $(C_1-C_4)$alkyl-$NR^xR^y$, $C(O)$—$(C_1-C_4)$alkyl, $C(O)O$—$(C_1-C_4)$alkyl, $C(O)$—$(C_1-C_4)$haloalkyl, $C(O)O$—$(C_1-C_4)$haloalkyl, $C(O)$—$(C_3-C_8)$cycloalkyl, $C(O)O$—$(C_3-C_8)$cycloalkyl, $C(O)$—$(C_2-C_6)$alkenyl, $C(O)O$—$(C_2-C_6)$alkenyl, $(C_1-C_4)$alkyl-O—$(C_1-C_4)$alkyl, $(C_1-C_4)$alkyl-$S(O)_n$—$(C_1-C_4)$alkyl, $C(O)$—$(C_1-C_4)$alkyl-$C(O)O$—$(C_1-C_4)$alkyl, phenyl, and phenoxy;

(B) Het is (1d)

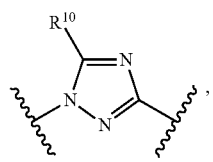
(1d)

wherein, $R^{10}$ may be optionally substituted with a substituent selected from the group consisting of H, F, Cl, Br, I, CN, $NO_2$, oxo, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, $C(O)$—$NR^xR^y$, $(C_1-C_4)$alkyl-$NR^xR^y$, $C(O)$—$(C_1-C_4)$alkyl, $C(O)O$—$(C_1-C_4)$alkyl, $C(O)$—$(C_1-C_4)$haloalkyl, $C(O)O$—$(C_1-C_4)$haloalkyl, $C(O)$—$(C_3-C_8)$cycloalkyl, $C(O)O$—$(C_3-C_8)$cycloalkyl, $C(O)$—$(C_2-C_6)$alkenyl, $C(O)O$—$(C_2-C_6)$alkenyl, $(C_1-C_4)$alkyl-O—$(C_1-C_4)$alkyl, $(C_1-C_4)$alkyl-$S(O)_n$—$(C_1-C_4)$alkyl, and $C(O)$—$(C_1-C_4)$alkyl-$C(O)O$—$(C_1-C_4)$alkyl, wherein each alkyl, haloalkyl, cycloalkyl, alkoxy, haloalkoxy, alkenyl, and alkynyl substituent may be optionally substituted with one or more substituents independently selected from the group consisting of H, F, Cl, Br, I, CN, $NO_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, $C(O)$—$NR^xR^y$, $(C_1-C_4)$alkyl-$NR^xR^y$, $C(O)$—$(C_1-C_4)$alkyl, $C(O)O$—$(C_1-C_4)$alkyl, $C(O)$—$(C_1-C_4)$haloalkyl, $C(O)O$—$(C_1-C_4)$haloalkyl, $C(O)$—$(C_3-C_8)$cycloalkyl, $C(O)O$—$(C_3-C_8)$cycloalkyl, $C(O)$—$(C_2-C_6)$alkenyl, $C(O)O$—$(C_2-C_6)$alkenyl, $(C_1-C_4)$alkyl-O—$(C_1-C_4)$alkyl, $(C_1-C_4)$alkyl-$S(O)_n$—$(C_1-C_4)$alkyl, $C(O)$—$(C_1-C_4)$alkyl-$C(O)O$—$(C_1-C_4)$alkyl, phenyl, and phenoxy;

(C) Ar$^1$ is (1e)

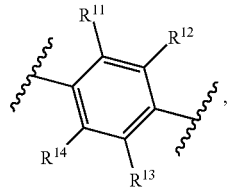

wherein, R$^{11}$, R$^{12}$, R$^{13}$, and R$^{14}$ are each independently selected from the group consisting of H, F, Cl, Br, I, CN, NO$_2$, (C$_1$-C$_4$)alkyl, (C$_1$-C$_4$)haloalkyl, (C$_3$-C$_8$)cycloalkyl, (C$_1$-C$_4$)alkoxy, (C$_1$-C$_4$)haloalkoxy, (C$_2$-C$_6$)alkenyl, (C$_2$-C$_6$)alkynyl, S(O)$_n$—(C$_1$-C$_4$)alkyl, S(O)$_n$—(C$_1$-C$_4$)haloalkyl, OSO$_2$—(C$_1$-C$_4$)alkyl, OSO$_2$—(C$_1$-C$_4$)haloalkyl, C(O)—NR$^x$R$^y$, (C$_1$-C$_4$)alkyl-NR$^x$R$^y$, C(O)—(C$_1$-C$_4$)alkyl, C(O)O—(C$_1$-C$_4$)alkyl, C(O)—(C$_1$-C$_4$)haloalkyl, C(O)O—(C$_1$-C$_4$)haloalkyl, C(O)—(C$_3$-C$_8$)cycloalkyl, C(O)O—(C$_3$-C$_8$)cycloalkyl, C(O)—(C$_2$-C$_6$)alkenyl, C(O)O—(C$_2$-C$_6$)alkenyl, (C$_1$-C$_4$)alkyl-O—(C$_1$-C$_4$)alkyl, (C$_1$-C$_4$)alkyl-S(O)$_n$—(C$_1$-C$_4$)alkyl, C(O)—(C$_1$-C$_4$)alkyl-C(O)O—(C$_1$-C$_4$)alkyl, phenyl, and phenoxy, wherein each alkyl, haloalkyl, cycloalkyl, alkoxy, haloalkoxy, alkenyl, alkynyl, phenyl, and phenoxy substituent may be optionally substituted with one or more substituents independently selected from the group consisting of H, F, Cl, Br, I, CN, NO$_2$, (C$_1$-C$_4$)alkyl, (C$_1$-C$_4$)haloalkyl, (C$_3$-C$_8$)cycloalkyl, (C$_1$-C$_4$)alkoxy, (C$_1$-C$_4$)haloalkoxy, (C$_2$-C$_6$)alkenyl, (C$_2$-C$_6$)alkynyl, S(O)$_n$—(C$_1$-C$_4$)alkyl, S(O)$_n$—(C$_1$-C$_4$)haloalkyl, OSO$_2$—(C$_1$-C$_4$)alkyl, OSO$_2$—(C$_1$-C$_4$)haloalkyl, C(O)—NR$^x$R$^y$, (C$_1$-C$_4$)alkyl-NR$^x$R$^y$, C(O)—(C$_1$-C$_4$)alkyl, C(O)O—(C$_1$-C$_4$)alkyl, C(O)—(C$_1$-C$_4$)haloalkyl, C(O)O—(C$_1$-C$_4$)haloalkyl, C(O)—(C$_3$-C$_8$)cycloalkyl, C(O)O—(C$_3$-C$_8$)cycloalkyl, C(O)—(C$_2$-C$_6$)alkenyl, C(O)O—(C$_2$-C$_6$)alkenyl, (C$_1$-C$_4$)alkyl-O—(C$_1$-C$_4$)alkyl, (C$_1$-C$_4$)alkyl-S(O)$_n$—(C$_1$-C$_4$)alkyl, C(O)—(C$_1$-C$_4$)alkyl-C(O)O—(C$_1$-C$_4$)alkyl, phenyl, and phenoxy;

(D) R$^{15}$ is selected from the group consisting of H, (C$_1$-C$_4$)alkyl, (C$_3$-C$_8$)cycloalkyl, (C$_2$-C$_6$)alkenyl, (C$_2$-C$_6$)alkynyl, S(O)$_n$—(C$_1$-C$_6$)alkyl, C(O)—NR$^x$R$^y$, C(O)-phenyl, (C$_1$-C$_6$)alkyl-NR$^x$R$^y$, C(O)O—(C$_1$-C$_6$)alkyl, C(O)—(C$_3$-C$_8$)cycloalkyl, C(O)O—(C$_3$-C$_8$)cycloalkyl, C(O)—(C$_2$-C$_6$)alkenyl, C(O)O—(C$_2$-C$_6$)alkenyl, (C$_1$-C$_4$)alkyl-O—(C$_1$-C$_4$)alkyl, (C$_1$-C$_4$)alkyl-OC(O)—(C$_1$-C$_4$)alkyl, (C$_1$-C$_4$)alkyl-S(O)$_n$—(C$_1$-C$_4$)alkyl, (C$_1$-C$_4$)alkyl-OC(O)O—(C$_1$-C$_4$)alkyl, wherein each alkyl, cycloalkyl, alkenyl, alkynyl, and phenyl may be optionally substituted with one or more substituents independently selected from the group consisting of H, F, Cl, Br, I, CN, NO$_2$, oxo, (C$_1$-C$_4$)alkyl, (C$_1$-C$_4$)haloalkyl, (C$_3$-C$_8$)cycloalkyl, (C$_1$-C$_4$)alkoxy, (C$_1$-C$_4$)haloalkoxy, (C$_2$-C$_6$)alkenyl, (C$_2$-C$_6$)alkynyl, S(O)$_n$—(C$_1$-C$_6$)alkyl, S(O)$_n$—(C$_1$-C$_4$)haloalkyl, OSO$_2$—(C$_1$-C$_4$)alkyl, OSO$_2$—(C$_1$-C$_4$)haloalkyl, C(O)—NR$^x$R$^y$, (C$_1$-C$_4$)alkyl-NR$^x$R$^y$, C(O)—(C$_1$-C$_4$)alkyl, C(O)O—(C$_1$-C$_4$)alkyl, C(O)—(C$_1$-C$_4$)haloalkyl, C(O)O—(C$_1$-C$_4$)haloalkyl, C(O)—(C$_3$-C$_8$)cycloalkyl, C(O)O—(C$_3$-C$_8$)cycloalkyl, C(O)—(C$_2$-C$_6$)alkenyl, C(O)O—(C$_2$-C$_6$)alkenyl, (C$_1$-C$_4$)alkyl-O—(C$_1$-C$_4$)alkyl, (C$_1$-C$_4$)alkyl-S(O)$_n$—(C$_1$-C$_4$)alkyl, C(O)—(C$_1$-C$_4$)alkyl-C(O)O—(C$_1$-C$_4$)alkyl, phenyl, and phenoxy;

(E) Q$^1$ is selected from the group consisting of O and S;
(F) Q$^2$ is selected from the group consisting of O and S;
(G) R$^{16}$ is selected from the group consisting of (J), H, (C$_1$-C$_4$)alkyl, (C$_3$-C$_8$)cycloalkyl, (C$_2$-C$_6$)alkenyl, (C$_2$-C$_6$)alkynyl, C(O)—(C$_1$-C$_4$)alkyl, (C$_1$-C$_4$)alkyl-O—(C$_1$-C$_4$)alkyl, (C$_1$-C$_4$)alkyl-S(O)$_n$—(C$_1$-C$_4$)alkyl, (C$_1$-C$_4$)alkylphenyl, (C$_1$-C$_4$)alkyl-O-phenyl, C(O)-(Het-1), Het-1, (C$_1$-C$_4$)alkyl-(Het-1), (C$_1$-C$_4$)alkyl-OC(O)—(C$_1$-C$_4$)alkyl, (C$_1$-C$_4$)alkyl-OC(O)—(C$_1$-C$_4$)alkyl, (C$_1$-C$_4$)alkyl-OC(O)O—(C$_1$-C$_4$)alkyl, (C$_1$-C$_4$)alkyl-OC(O)—NR$^x$R$^y$, (C$_1$-C$_4$)alkyl-C(O)—N(R$^x$)(C$_1$-C$_4$)alkyl-(Het-1), (C$_1$-C$_4$)alkyl-C(O)-(Het-1), (C$_1$-C$_4$)alkyl-C(O)—N(R$^x$)(C$_1$-C$_4$)alkyl(NR$^x$R$^y$)—C(O)OH, (C$_1$-C$_4$)alkyl-C(O)—N(R$^x$)(C$_1$-C$_4$)alkyl-NR$^x$R$^y$, (C$_1$-C$_4$)alkyl-C(O)—N(R$^x$)(C$_1$-C$_4$)alkyl-N(R$^x$)—C(O)O—(C$_1$-C$_4$)alkyl, (C$_1$-C$_4$)alkyl-C(O)—N(R$^x$)(C$_1$-C$_4$)alkyl(N(R$^x$)—C(O)O—(C$_1$-C$_4$)alkyl)-C(O)OH, (C$_1$-C$_4$)alkyl-C(O)-(Het-1)-C(O)O—(C$_1$-C$_4$)alkyl, (C$_1$-C$_4$)alkyl-OC(O)O—(C$_1$-C$_4$)alkyl, (C$_1$-C$_4$)alkyl-OC(O)—(C$_1$-C$_4$)alkyl, (C$_1$-C$_4$)alkyl-OC(O)—(C$_3$-C$_8$)cycloalkyl, (C$_1$-C$_4$)alkyl-OC(O)-(Het-1), (C$_1$-C$_4$)alkyl-OC(O)—(C$_1$-C$_4$)alkyl-N(R$^x$)—C(O)O—(C$_1$-C$_4$)alkyl, (C$_1$-C$_4$)alkyl-NR$^x$R$^y$, (C$_1$-C$_4$)alkyl-S(O)$_n$-(Het-1), and (C$_1$-C$_4$)alkyl-O-(Het-1), wherein each alkyl, cycloalkyl, alkenyl, alkynyl, phenyl, and (Het-1) may be optionally substituted with one or more substituents independently selected from the group consisting of H, F, Cl, Br, I, CN, NO$_2$, NR$^x$R$^y$, (C$_1$-C$_4$)alkyl, (C$_1$-C$_4$)haloalkyl, (C$_3$-C$_8$)cycloalkyl, (C$_1$-C$_4$)alkoxy, (C$_2$-C$_6$)alkenyl, (C$_2$-C$_6$)alkynyl, S(O)$_n$—(C$_1$-C$_4$)alkyl, S(O)$_n$—(C$_1$-C$_4$)haloalkyl, OSO$_2$—(C$_1$-C$_4$)alkyl, OSO$_2$—(C$_1$-C$_4$)haloalkyl, C(O)H, C(O)OH, C(O)—NR$^x$R$^y$, (C$_1$-C$_4$)alkyl-NR$^x$R$^y$, C(O)—(C$_1$-C$_4$)alkyl, C(O)O—(C$_1$-C$_4$)alkyl, C(O)—(C$_1$-C$_4$)haloalkyl, C(O)O—(C$_1$-C$_4$)haloalkyl, C(O)—(C$_3$-C$_8$)cycloalkyl, C(O)O—(C$_3$-C$_8$)cycloalkyl, C(O)—(C$_2$-C$_6$)alkenyl, C(O)O—(C$_2$-C$_6$)alkenyl, (C$_1$-C$_4$)alkyl-O—(C$_1$-C$_4$)alkyl, (C$_1$-C$_4$)alkyl-S(O)$_n$—(C$_1$-C$_4$)alkyl, C(O)—(C$_1$-C$_4$)alkyl-C(O)O—(C$_1$-C$_4$)alkyl), phenyl, phenoxy, Si((C$_1$-C$_4$)alkyl)$_3$, S(O)$_n$—NR$^x$R$^y$, and (Het-1);

(H) R$^{17}$ is selected from the group consisting of (J), H, (C$_1$-C$_4$)alkyl, (C$_3$-C$_8$)cycloalkyl, (C$_2$-C$_6$)alkenyl, (C$_2$-C$_6$)alkynyl, C(O)—(C$_1$-C$_4$)alkyl, (C$_1$-C$_4$)alkyl-O—(C$_1$-C$_4$)alkyl, (C$_1$-C$_4$)alkyl-S(O)$_n$—(C$_1$-C$_4$)alkyl, (C$_1$-C$_4$)alkylphenyl, (C$_1$-C$_4$)alkyl-O-phenyl, C(O)-(Het-1), Het-1, (C$_1$-C$_4$)alkyl-(Het-1), (C$_1$-C$_4$)alkyl-OC(O)—(C$_1$-C$_4$)alkyl, (C$_1$-C$_4$)alkyl-OC(O)—(C$_1$-C$_4$)alkyl, (C$_1$-C$_4$)alkyl-OC(O)O—(C$_1$-C$_4$)alkyl, (C$_1$-C$_4$)alkyl-OC(O)—NR$^x$R$^y$, (C$_1$-C$_4$)alkyl-C(O)—N(R$^x$)(C$_1$-C$_4$)alkyl-(Het-1), (C$_1$-C$_4$)alkyl-C(O)-(Het-1), (C$_1$-C$_4$)alkyl-C(O)—N(R$^x$)(C$_1$-C$_4$)alkyl(NR$^x$R$^y$)—C(O)OH, (C$_1$-C$_4$)alkyl-C(O)—N(R$^x$)(C$_1$-C$_4$)alkyl-NR$^x$R$^y$, (C$_1$-C$_4$)alkyl-C(O)—N(R$^x$)(C$_1$-C$_4$)alkyl-N(R$^x$)—C(O)O—(C$_1$-C$_4$)alkyl, (C$_1$-C$_4$)alkyl-C(O)—N(R$^x$)(C$_1$-C$_4$)alkyl(N(R$^x$)—C(O)O—(C$_1$-C$_4$)alkyl)-C(O)OH, (C$_1$-C$_4$)alkyl-C(O)-(Het-1)-C(O)O—(C$_1$-C$_4$)alkyl, (C$_1$-C$_4$)alkyl-OC(O)O—(C$_1$-C$_4$)alkyl, (C$_1$-C$_4$)alkyl-OC(O)—(C$_1$-C$_4$)alkyl, (C$_1$-C$_4$)alkyl-OC(O)—(C$_3$-C$_8$)cycloalkyl, (C$_1$-C$_4$)alkyl-OC(O)-(Het-1), ($C_1$-$C_4$)alkyl-OC(O)—($C_1$-$C_4$)alkyl-N($R^x$)—C(O)O—($C_1$-$C_4$)alkyl, ($C_1$-$C_4$)alkyl-$NR^xR^y$, ($C_1$-$C_4$)alkyl-S(O)$_n$-(Het-1), and ($C_1$-$C_4$)alkyl-O-(Het-1), wherein each alkyl, cycloalkyl, alkenyl, alkynyl, phenyl, and (Het-1) may be optionally substituted with one or more substituents independently selected from the group consisting of H, F, Cl, Br, I, CN, $NO_2$, $NR^xR^y$, ($C_1$-$C_4$)alkyl, ($C_1$-$C_4$)haloalkyl, ($C_3$-$C_8$)cycloalkyl, ($C_1$-$C_4$)alkoxy, ($C_2$-$C_6$)alkenyl, ($C_2$-$C_6$)alkynyl, S(O)$_n$—($C_1$-$C_4$)alkyl, S(O)$_n$—($C_1$-$C_4$)haloalkyl, $OSO_2$—($C_1$-$C_4$)alkyl, $OSO_2$—($C_1$-$C_4$)haloalkyl, C(O)H, C(O)OH, C(O)—$NR^xR^y$, ($C_1$-$C_4$)alkyl-$NR^xR^y$, C(O)—($C_1$-$C_4$)alkyl, C(O)O—($C_1$-$C_4$)alkyl, C(O)—($C_1$-$C_4$)haloalkyl, C(O)O—($C_1$-$C_4$)haloalkyl, C(O)—($C_3$-$C_8$)cycloalkyl, C(O)O—($C_3$-$C_8$)cycloalkyl, C(O)—($C_2$-$C_6$)alkenyl, C(O)O—($C_2$-$C_6$)alkenyl, ($C_1$-$C_4$)alkyl-O—($C_1$-$C_4$)alkyl, ($C_1$-$C_4$)alkyl-S(O)$_n$—($C_1$-$C_4$)alkyl, C(O)—($C_1$-$C_4$)alkyl-C(O)O—($C_1$-$C_4$)alkyl, phenyl, phenoxy, Si(($C_1$-$C_4$)alkyl)$_3$, S(O)$_n$—$NR^xR^y$, and (Het-1);

(I) $L^2$ is (1f)

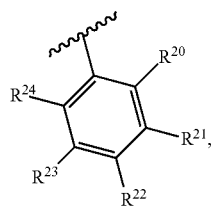

wherein, $R^{20}$, $R^{21}$, $R^{22}$, $R^{23}$, and $R^{24}$ are each independently selected from the group consisting of H, F, Cl, Br, I, CN, $NO_2$, $NR^xR^y$, ($C_1$-$C_4$)alkyl, ($C_1$-$C_4$)haloalkyl, ($C_3$-$C_8$)cycloalkyl, ($C_1$-$C_4$)alkoxy, ($C_1$-$C_4$)haloalkoxy, ($C_2$-$C_6$)alkenyl, ($C_2$-$C_6$)alkynyl, S(O)$_n$—($C_1$-$C_4$)alkyl, S(O)$_n$—($C_1$-$C_4$)haloalkyl, $OSO_2$—($C_1$-$C_4$)alkyl, $OSO_2$—($C_1$-$C_4$)haloalkyl, C(O)H, C(O)—$NR^xR^y$, ($C_1$-$C_4$)alkyl-$NR^xR^y$, C(O)—($C_1$-$C_4$)alkyl, C(O)O—($C_1$-$C_4$)alkyl, C(O)—($C_1$-$C_4$)haloalkyl, C(O)O—($C_1$-$C_4$)haloalkyl, C(O)—($C_3$-$C_8$)cycloalkyl, C(O)O—($C_1$-$C_4$)cycloalkyl, C(O)—($C_2$-$C_6$)alkenyl, C(O)O—($C_2$-$C_6$)alkenyl, O—($C_1$-$C_4$)alkyl, S—($C_1$-$C_4$)alkyl, ($C_1$-$C_4$)alkyl-O—($C_1$-$C_4$)alkyl, C(O)—($C_1$-$C_4$)alkyl-C(O)O—($C_1$-$C_4$)alkyl, phenyl, phenoxy, and (Het-1), wherein each alkyl, cycloalkyl, alkenyl, phenyl, and (Het-1) substituent may be optionally substituted with one or more substituents independently selected from the group consisting of H, F, Cl, Br, I, CN, $NO_2$, $NR^xR^y$, ($C_1$-$C_4$)alkyl, ($C_1$-$C_4$)haloalkyl, ($C_3$-$C_8$)cycloalkyl, ($C_1$-$C_4$)alkoxy, ($C_1$-$C_4$)haloalkoxy, ($C_2$-$C_6$)alkenyl, ($C_2$-$C_6$)alkynyl, S(O)$_n$—($C_1$-$C_4$)alkyl, S(O)$_n$—($C_1$-$C_4$)haloalkyl, $OSO_2$—($C_1$-$C_4$)alkyl, $OSO_2$—($C_1$-$C_4$)haloalkyl, C(O)H, C(O)—$NR^xR^y$, ($C_1$-$C_4$)alkyl-$NR^xR^y$, C(O)—($C_1$-$C_4$)alkyl, C(O)O—($C_1$-$C_4$)alkyl, C(O)—($C_1$-$C_4$)haloalkyl, C(O)O—($C_1$-$C_4$)haloalkyl, C(O)—($C_3$-$C_8$)cycloalkyl, C(O)O—($C_1$-$C_4$)cycloalkyl, C(O)—($C_2$-$C_6$)alkenyl, C(O)O—($C_2$-$C_6$)alkenyl, O—($C_1$-$C_4$)alkyl, S—($C_1$-$C_4$)alkyl, ($C_1$-$C_4$)alkyl-O—($C_1$-$C_4$)alkyl, C(O)—($C_1$-$C_4$)alkyl-C(O)O—($C_1$-$C_4$)alkyl, phenyl, phenoxy, and (Het-1);

(J) $R^{16}$ and $R^{17}$ along with $C^x(Q^2)(N^x)$, is (1g)

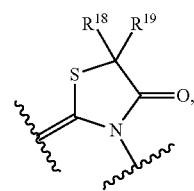

wherein $R^{18}$ and $R^{19}$ are each independently selected from the group consisting of H, F, Cl, Br, I, CN, $NO_2$, oxo, thioxo, ($C_1$-$C_4$)alkyl, ($C_1$-$C_4$)haloalkyl, ($C_3$-$C_8$)cycloalkyl, ($C_1$-$C_4$)alkoxy, ($C_1$-$C_4$)haloalkoxy, ($C_2$-$C_6$)alkenyl, ($C_2$-$C_6$)alkynyl, S(O)$_n$—($C_1$-$C_4$)alkyl, S(O)$_n$—($C_1$-$C_4$)haloalkyl, $OSO_2$—($C_1$-$C_4$)alkyl, $OSO_2$—($C_1$-$C_4$)haloalkyl, C(O)H, C(O)—($C_1$-$C_4$)alkyl, C(O)O—($C_1$-$C_4$)alkyl, C(O)—($C_1$-$C_4$)haloalkyl, C(O)O—($C_1$-$C_4$)haloalkyl, C(O)—($C_3$-$C_8$)cycloalkyl, C(O)O—($C_3$-$C_8$)cycloalkyl, C(O)—($C_2$-$C_6$)alkenyl, C(O)O—($C_2$-$C_6$)alkenyl, ($C_1$-$C_4$)alkyl-O—($C_1$-$C_4$)alkyl, ($C_1$-$C_4$)alkyl-S(O)$_n$—($C_1$-$C_4$)alkyl, C(O)—($C_1$-$C_4$)alkyl-C(O)O—($C_1$-$C_4$)alkyl, phenyl, and (Het-1);

(K) $R^x$ and $R^y$ are each independently selected from the group consisting of H, ($C_1$-$C_4$)alkyl, ($C_1$-$C_4$)haloalkyl, ($C_3$-$C_8$)cycloalkyl, ($C_1$-$C_4$)alkoxy, ($C_1$-$C_4$)haloalkoxy, ($C_2$-$C_6$)alkenyl, ($C_2$-$C_6$)alkynyl, S(O)$_n$—($C_1$-$C_4$)alkyl, S(O)$_n$—($C_1$-$C_4$)haloalkyl, $OSO_2$—($C_1$-$C_4$)alkyl, $OSO_2$—($C_1$-$C_4$)haloalkyl, C(O)H, C(O)—($C_1$-$C_4$)alkyl, C(O)O—($C_1$-$C_4$)alkyl, C(O)—($C_1$-$C_4$)haloalkyl, C(O)O—($C_1$-$C_4$)haloalkyl, C(O)—($C_3$-$C_8$)cycloalkyl, C(O)O—($C_3$-$C_8$)cycloalkyl, C(O)—($C_2$-$C_6$)alkenyl, C(O)O—($C_2$-$C_6$)alkenyl, ($C_1$-$C_4$)alkyl-O—($C_1$-$C_4$)alkyl, ($C_1$-$C_4$)alkyl-S(O)$_n$—($C_1$-$C_4$)alkyl, C(O)—($C_1$-$C_4$)alkyl-C(O)O—($C_1$-$C_4$)alkyl, and phenyl, wherein each alkyl, haloalkyl, cycloalkyl, alkoxy, haloalkoxy, alkenyl, alkynyl, and phenyl may be optionally substituted with one or more substituents independently selected from the group consisting of H, F, Cl, Br, I, CN, $NO_2$, ($C_1$-$C_4$)alkyl, ($C_1$-$C_4$)haloalkyl, ($C_3$-$C_8$)cycloalkyl, ($C_1$-$C_4$)alkoxy, ($C_1$-$C_4$)haloalkoxy, ($C_2$-$C_6$)alkenyl, ($C_2$-$C_6$)alkynyl, S(O)$_n$—($C_1$-$C_4$)alkyl, S(O)$_n$—($C_1$-$C_4$)haloalkyl, $OSO_2$—($C_1$-$C_4$)alkyl, $OSO_2$—($C_1$-$C_4$)haloalkyl, C(O)H, C(O)—($C_1$-$C_4$)alkyl, C(O)O—($C_1$-$C_4$)alkyl, C(O)—($C_1$-$C_4$)haloalkyl, C(O)O—($C_1$-$C_4$)haloalkyl, C(O)—($C_3$-$C_8$)cycloalkyl, C(O)O—($C_3$-$C_8$)cycloalkyl, C(O)—($C_2$-$C_6$)alkenyl, C(O)O—($C_2$-$C_6$)alkenyl, ($C_1$-$C_4$)alkyl-O—($C_1$-$C_4$)alkyl, ($C_1$-$C_4$)alkyl-S(O)$_n$—($C_1$-$C_4$)alkyl, C(O)—($C_1$-$C_4$)alkyl-C(O)O—($C_1$-$C_4$)alkyl, phenyl, and (Het-1);

(L) (Het-1) is a 5- or 6-membered, saturated or unsaturated, heterocyclic ring, containing one or more heteroatoms independently selected from nitrogen, sulfur, or oxygen, wherein each heterocyclic ring may be optionally substituted with one or more substituents independently selected from the group consisting of H, F, Cl, Br, I, CN, $NO_2$, oxo, ($C_1$-$C_4$)alkyl, ($C_1$-$C_4$)haloalkyl, ($C_3$-$C_8$)cycloalkyl, ($C_1$-$C_4$)alkoxy, ($C_1$-$C_4$)haloalkoxy, ($C_2$-

$C_6$)alkenyl, ($C_2$-$C_6$)alkynyl, S(O)$_n$—($C_1$-$C_4$)alkyl, S(O)$_n$—($C_1$-$C_4$)haloalkyl, OSO$_2$—($C_1$-$C_4$)alkyl, OSO$_2$—($C_1$-$C_4$)haloalkyl, C(O)—NR$^x$R$^y$, ($C_1$-$C_4$)alkyl-NR$^x$R$^y$, C(O)—($C_1$-$C_4$)alkyl, C(O)O—($C_1$-$C_4$)alkyl, C(O)—($C_1$-$C_4$)haloalkyl, C(O)O—($C_1$-$C_4$)haloalkyl, C(O)—($C_3$-$C_8$)cycloalkyl, C(O)O—($C_3$-$C_8$)cycloalkyl, C(O)—($C_2$-$C_6$)alkenyl, C(O)O—($C_2$-$C_6$)alkenyl, ($C_1$-$C_4$)alkyl-O—($C_1$-$C_4$)alkyl, ($C_1$-$C_4$)alkyl-S(O)$_n$—($C_1$-$C_4$)alkyl, C(O)—($C_1$-$C_4$)alkyl-C(O)O—($C_1$-$C_4$)alkyl, phenyl, and phenoxy, wherein each alkyl, haloalkyl, cycloalkyl, alkoxy, haloalkoxy, alkenyl, alkynyl, phenyl, and phenoxy substituent may be optionally substituted with one or more substituents independently selected from the group consisting of H, F, Cl, Br, I, CN, NO$_2$, ($C_1$-$C_4$)alkyl, ($C_1$-$C_4$)haloalkyl, ($C_3$-$C_8$)cycloalkyl, ($C_1$-$C_4$)alkoxy, ($C_1$-$C_4$)haloalkoxy, ($C_2$-$C_6$)alkenyl, ($C_2$-$C_6$)alkynyl, S(O)$_n$—($C_1$-$C_4$)alkyl, S(O)$_n$—($C_1$-$C_4$)haloalkyl, OSO$_2$—($C_1$-$C_4$)alkyl, OSO$_2$—($C_1$-$C_4$)haloalkyl, C(O)—NR$^x$R$^y$, ($C_1$-$C_4$)alkyl-NR$^x$R$^y$, C(O)—($C_1$-$C_4$)alkyl, C(O)O—($C_1$-$C_4$)alkyl, C(O)—($C_1$-$C_4$)haloalkyl, C(O)O—($C_1$-$C_4$)haloalkyl, C(O)—($C_3$-$C_8$)cycloalkyl, C(O)O—($C_3$-$C_8$)cycloalkyl, C(O)—($C_2$-$C_6$)alkenyl, C(O)O—($C_2$-$C_6$)alkenyl, ($C_1$-$C_4$)alkyl-O—($C_1$-$C_4$)alkyl, ($C_1$-$C_4$)alkyl-S(O)$_n$—($C_1$-$C_4$)alkyl, C(O)—($C_1$-$C_4$)alkyl-C(O)O—($C_1$-$C_4$)alkyl, phenyl, and phenoxy; and (M) n are each independently 0, 1, or 2.

In another embodiment (A) $L^1$ is selected from the group consisting of

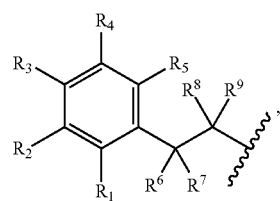
(1a)

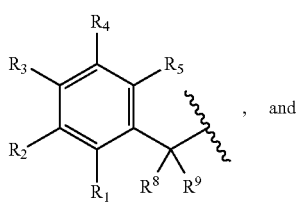
(1b), and

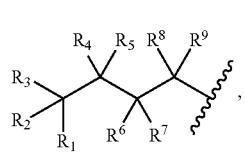
(1c)

wherein, $R^1$, $R^2$, $R^3$, $R^4$, $R^5$, $R^6$, $R^7$, $R^8$, $R^9$ are each independently selected from the group consisting of H, F, ($C_1$-$C_4$)haloalkyl, and ($C_1$-$C_4$)haloalkoxy;

(B) Het is (1d)

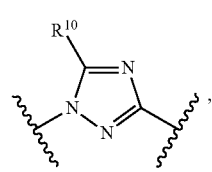
(1d)

wherein, $R^{10}$ is H;

(C) $Ar^1$ is (1e)

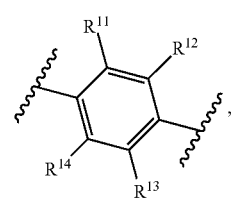
(1e)

wherein, $R^{11}$, $R^{12}$, $R^{13}$, and $R^{14}$ are each independently H;

(D) $R^{15}$ is H;

(E) $Q^1$ is O;

(F) $Q^2$ is S;

(G) $R^{16}$ is (J);

(H) $R^{17}$ is (J);

(I) $L^2$ is (1f)

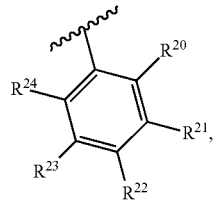
(1f)

wherein, $R^{20}$, $R^{21}$, $R^{22}$, $R^{23}$, and $R^{24}$ are each independently selected from the group consisting of H and ($C_1$-$C_4$)alkyl; and (J) $R^{16}$ and $R^{17}$ along with $C^x(Q^2)(N^x)$, is (1g)

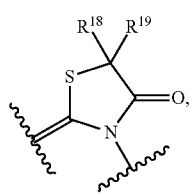
(1g)

wherein $R^{18}$ and $R^{19}$ are each independently H.

In another embodiment (A) $L^1$ is selected from the group consisting of (1a)

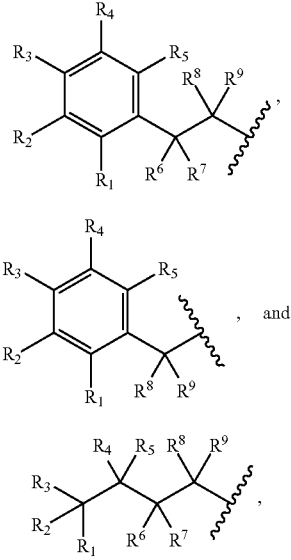

(1b)

(1c)

wherein, $R^1$, $R^2$, $R^3$, $R^4$, $R^5$, $R^6$, $R^7$, $R^8$, $R^9$ are each independently selected from the group consisting of H, F, $CF_3$, and $OCF_3$;

(B) Het is (1d)

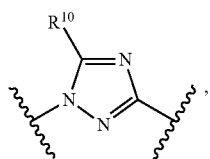

(1d)

wherein, $R^{10}$ is H;

(C) $Ar^1$ is (1e)

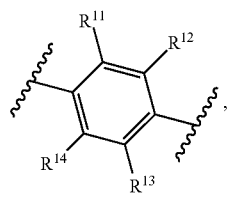

(1e)

wherein, $R^{11}$, $R^{12}$, $R^{13}$, and $R^{14}$ are each independently H;

(D) $R^{15}$ is H;

(E) $Q^1$ is O;

(F) $Q^2$ is S;

(G) $R^{16}$ is (J);

(H) $R^{17}$ is (J);

(I) $L^2$ is (1f)

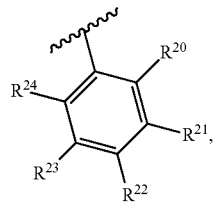

(1f)

wherein, $R^{20}$, $R^{21}$, $R^{22}$, $R^{23}$, and $R^{24}$ are each independently selected from the group consisting of H, $CH_3$, and $CH(CH_3)_2$; and (J) $R^{16}$ and $R^{17}$ along with $C^x(Q^2)(N^x)$, is (1g)

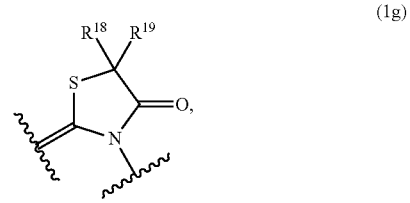

(1g)

wherein, $R^{18}$ and $R^{19}$ are each independently H.

Preparation of Molecules of Formula One

Many of the molecules of Formula One may be depicted in two or more tautomeric forms such as when $R^{16}$ and $R^{17}$ are H (Scheme TAU). For the sake of simplifying the schemes, all molecules have been depicted as existing as a single tautomer. Any and all energetically accessible tautomers are included within the scope of this Formula One, and no inference should be made as to whether the molecule exists as the tautomeric form in which it is drawn.

Scheme TAU

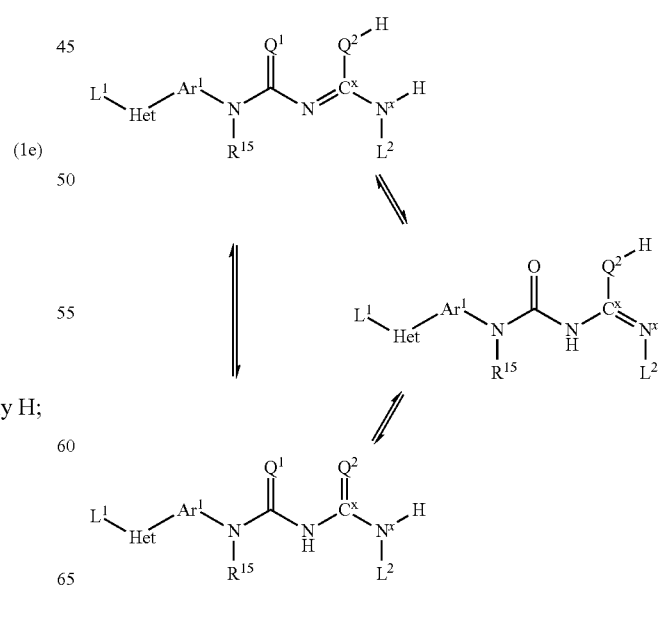

The molecules of Formula One will generally have a molecular mass of about 400 Daltons to about 1200 Daltons.

Preparation of Isocyanates

Molecules of Formula One disclosed herein may be prepared from the corresponding isocyanates 1-2, wherein $L^1$, Het, and $Ar^1$ are as previously disclosed. In some cases these isocyanates are not isolated, but are instead generated in situ from a suitable precursor and used directly in the preparation of molecules of Formula One. Such suitable precursors are amines 1-1, wherein $L^1$, Het, and $Ar^1$ are as previously disclosed, which may be converted into isocyanates 1-2 by using one of several common reagents such as phosgene, diphosgene, or triphosgene, in a mixed solvent system such as dichloromethane and water or diethyl ether and water, in the presence of a base such as sodium bicarbonate or triethylamine, at temperatures from about −10° C. to about 50° C. (Scheme 1, step a).

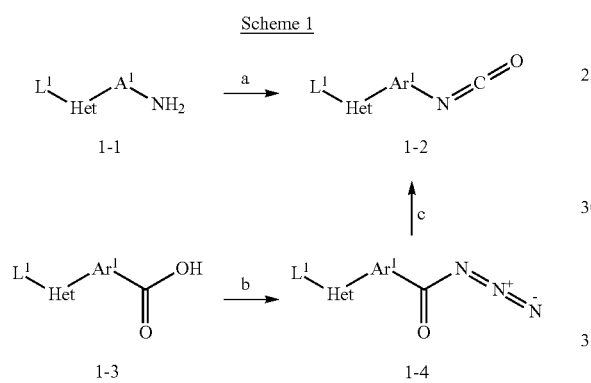

Alternatively, the isocyanates may be generated via the Curtius rearrangement of acyl azides 1-4, wherein $L^1$, Het, and $Ar^1$ are as previously disclosed, which are, in turn, prepared from the corresponding carboxylic acids 1-3, wherein $L^1$, Het, and $Ar^1$ are as previously disclosed. Formation of acyl azides 1-4 may occur either by treatment of the acid with ethyl chloroformate and sodium azide in the presence of an amine base such as triethylamine, or with diphenylphosphoryl azide in the presence of an amine base such as trimethylamine (Scheme 1, step b). Acyl azides 1-4 are then made to undergo a thermally-induced Curtius rearrangement, leading to the corresponding isocyanates 1-2. Depending on the nature of the particular acyl azide, this rearrangement may occur spontaneously at room temperature, or it may require heating from 40° C. to about 100° C. in a solvent, such as toluene, acetonitrile, or an ethereal solvent such as dioxane or tetrahydrofuran. Acyl azides 1-4 are not always fully characterized, but may simply be heated directly without characterization, to generate isocyanates 1-2.

Preparation of Linear Biurets

Isocyanates 1-2 may be treated directly with ureas 2-1, wherein $Q^2$ and $L^2$ are as previously disclosed, in the presence of about 0.1 equivalents to about 2 equivalents of an inorganic base such as cesium carbonate or sodium hydride, resulting in the formation of biurets 2-2, wherein $L^1$, Het, $Ar^1$, $Q^2$, and $L^2$ are as previously disclosed (Scheme 2, step a). The reaction can be performed at temperatures from about 0° C. to about 100° C., preferably from about 20° C. to about 80° C., in an aprotic solvent or solvent mixture chosen from acetonitrile, acetone, toluene, tetrahydrofuran, dichloroethane, dichloromethane, or mixtures thereof, but use of acetonitrile is preferred.

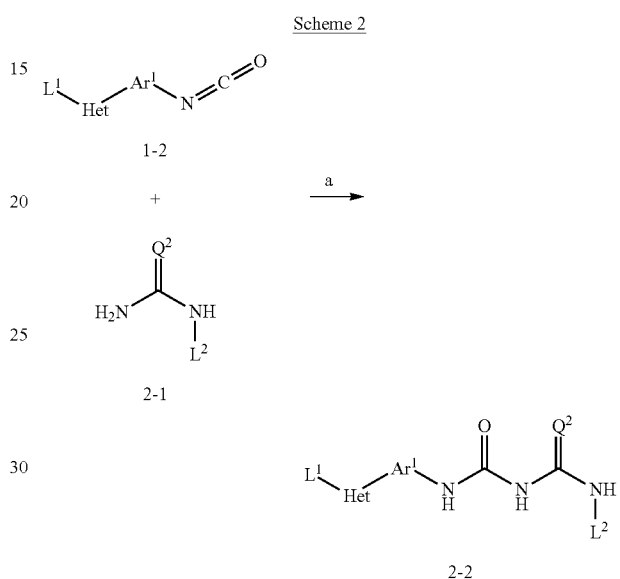

Preparation of Substituted Linear Biurets

Linear biurets 2-2 may be treated with $R^{16}$-halo, wherein $R^{16}$ is as previously disclosed, in a protic solvent, such as ethanol, in the presence of a base, such as sodium acetate, at temperatures from about 0° C. to about 60° C., to yield substituted linear biurets 3-1, wherein $L^1$, Het, $Ar^1$, $Q^2$, $R^{16}$, and $L^2$ are as previously disclosed (Scheme 3, step a).

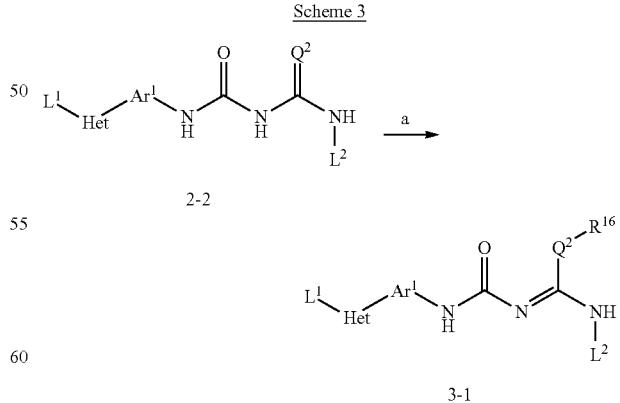

Preparation of Cyclic Biurets

Linear biurets 2-2 generated in situ may be converted directly without purification into a variety of cyclized analogs (Scheme 4), or they can be isolated from the reaction medium prior to cyclization. Cyclization may be achieved by treatment with an a-halo ester such as methyl bromoacetate to form 2-imino-1,3-chalcogenazolin-4-ones 4-1, wherein $L^1$, Het, $Ar^1$, $Q^2$, $R^{18}$, $R^{19}$, and $L^2$ areas previously disclosed (Scheme 4, step a); vicinal dihalides such as 1-bromo-2-chloroethane or 1,2-dichloroethane, to form 2-imino-1,3-chalogenazolines 4-2, wherein $L^1$, Het, $Ar^1$, $Q^2$, $R^{18}$, $R^{19}$, and $L^2$ are as previously disclosed (Scheme 4, step b); a-halo ketones such as chloroacetone to form 2-imino-1,3-chalcogenazoles 4-3, wherein $L^1$, Het, $Ar^1$, $Q^2$, $R^{18}$, $R^{19}$, and $L^2$ are as previously disclosed (Scheme 4, step c); 1,3-dihalopropanes such as 1-bromo-3-chloro-propane to form 2-imino-1,3-chalcogenazinanes 4-4, wherein $L^1$, Het, $Ar^1$, $Q^2$, $R^{18}$, $R^{19}$, and $L^2$ are as previously disclosed (Scheme 4, step d); or α,β-unsaturated acid chlorides such as acryloyl chloride to form 2-imino-1,3-chalcogenazinones 4-5, wherein $L^1$, Het, $Ar^1$, $Q^2$, $R^{18}$, $R^{19}$, and $L^2$ are as previously disclosed (Scheme 4, step e). With step a in Scheme 4, the use of sodium acetate in a protic solvent such as ethanol or methanol, at temperatures ranging from about 20° C. to about 70° C. is preferred. With step b in Scheme 4, the use of an inorganic base such as potassium carbonate in a solvent such as acetonitrile or (preferably) 2-butanone, at a temperature between about 0° C. and about 80° C., is preferred.

An alternative method for preparing cyclic biurets is described in Scheme 5. 2-Imino-1,3-chalcogenazoheterocycles 5-1, wherein $Q^2C^xN^x$, $R^{16}$, $R^{17}$, and $L^2$ are as previously disclosed, may be treated directly with isocyanates 1-2, either in the absence of base or in the presence of about 0.1 equivalents to about 2 equivalents of an inorganic base, such as cesium carbonate or sodium hydride, to form cyclic thiobiurets 5-2, wherein $L^1$, Het, $Ar^1$, $Q^2$, $R^{16}$, $R^{17}$, and $L^2$ are as previously disclosed (Scheme 5, step a). The reaction may be performed at temperatures from about 0° C. to about 100° C., preferably from about 20° C. to about 80° C., in an aprotic solvent or solvent mixture chosen from acetonitrile, acetone, toluene, tetrahydrofuran, 1,2-dichloroethane, dichloromethane, or mixtures thereof, but use of acetonitrile is preferred.

Scheme 4

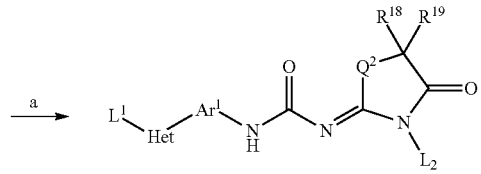

4-1

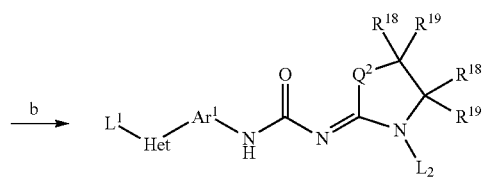

4-2

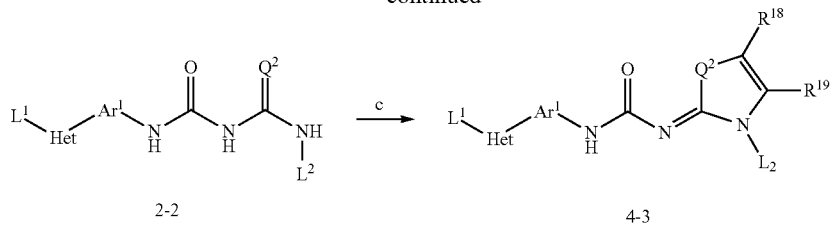

2-2

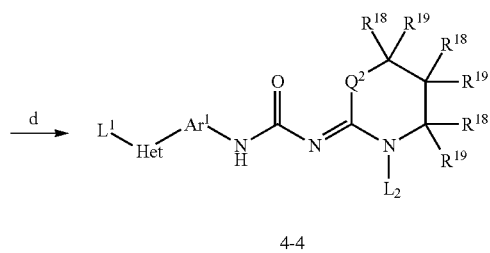

4-3

4-4

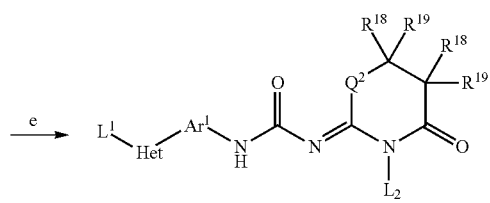

4-5

Alternatively, 2-imino-1,3-chalcogenazoheterocycles 5-1 may be reacted with 4-nitrophenyl chloroformate, forming 4-nitrophenyl carbamates 5-3, wherein $Q^2C^xN^x$, $R^{16}$, $R^{17}$, and $L^2$ are as previously disclosed (Scheme 5, step b). This reaction may be conducted with equimolar quantities of 2-imino-1,3-chalcogenazoheterocycles 5-1 and the chloroformate, in a polar aprotic solvent, such as tetrahydrofuran, dioxane, or acetonitrile, in the presence of from about 0.1 equivalents to about 2 equivalents of an inorganic base, such as cesium carbonate or potassium carbonate, preferably at about room temperature. 4-Nitrophenyl carbamates 5-3 may be isolated by filtration and concentration of the filtrate, or 4-nitrophenyl carbamates 5-3 may be used directly (Scheme 5, step c). Treatment of 4-nitrophenyl carbamates 5-3 with amines 1-1 may generate cyclic thiobiurets 5-2. Step c may also be conducted in the presence of an inorganic base, such as cesium carbonate or potassium carbonate, from about 0.1 equivalents to about 2 equivalents, preferably about 1 equivalents to about 1.2 equivalents, at temperatures from about 0° C. to about 100° C., preferably about room temperature.

Scheme 5

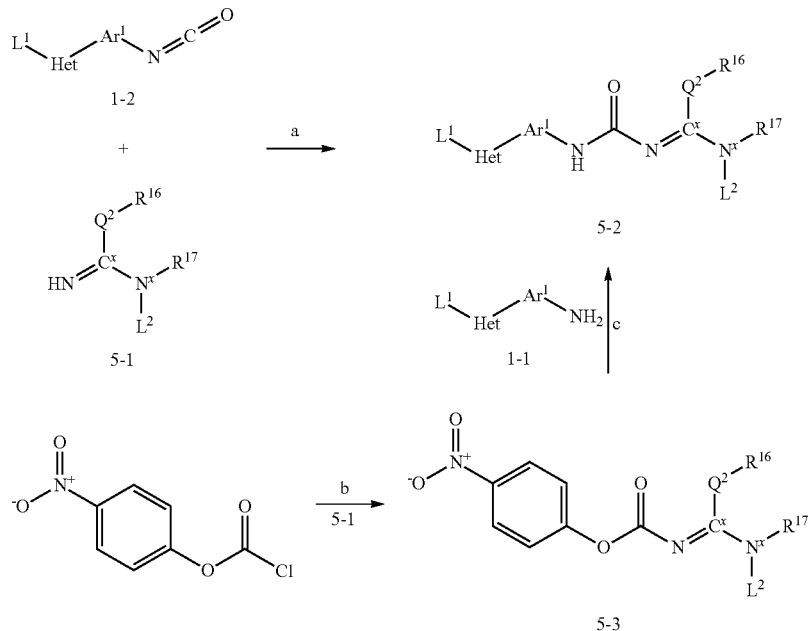

An alternative method for preparing cyclic biurets is described in Scheme 6. Amines 1-1 may be reacted with 4-nitrophenyl chloroformate, forming 4-nitrophenyl carbamates 6-1, wherein $L^1$, Het, and $Ar^1$ are as previously disclosed (Scheme 6, step a). This reaction may be conducted with equimolar quantities of amines 1-1 and the chloroformate, in a polar aprotic solvent, such as tetrahydrofuran, dioxane, or acetonitrile, in the presence of from about 0.1 equivalents to about 2 equivalents of an inorganic base, such as cesium carbonate or potassium carbonate, preferably at about room temperature. 4-Nitrophenyl carbamates 6-1 may be isolated by filtration and concentration of the filtrate, or 4-nitrophenyl carbamates 6-1 may be used directly (Scheme 6, step b). Treatment of 4-nitrophenyl carbamates 6-1 with 2-imino-1,3-chalcogenazoheterocycles 5-1 may generate cyclic thiobiurets 5-2. This reaction may be conducted with equimolar quantities of nitrophenyl carbamates 6-1 and 2-imino-1,3-chalcogenazoheterocycles 5-1, in a polar aprotic solvent, acetonitrile, in the presence of from about 0.1 equivalents to about 2 equivalents of an inorganic base, such as cesium carbonate or potassium carbonate, preferably at about room temperature.

Scheme 6

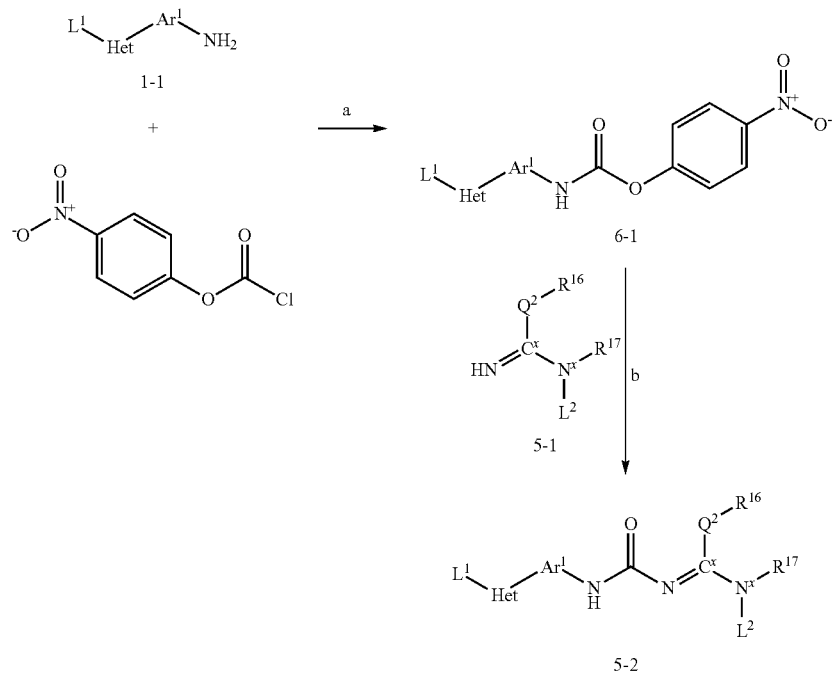

Preparation of Isocyanate Precursors

Precursors required for preparation of isocyanates 1-2 include amines 1-1 and acids 1-3. Methods for their preparation are described in Scheme 7. The coupling of halo-heterocycles 7-1, wherein Halo is Cl, Br, or I, and $L^1$ and Het are as previously disclosed, with J-Ar$^1$—B(OR)$_2$, wherein R is H or tetramethylethylene, J is C(O)OH or C(O)O(C$_1$-C$_4$) alkyl or NH$_2$, and Ar$^1$ is as previously disclosed, may be accomplished using a palladium catalyst such as tetrakis(triphenylphosphine)palladium(O), in the presence of a base, such as sodium bicarbonate, potassium phosphate, or cesium fluoride, in a suitable solvent system, such as acetonitrile and water, at temperatures from about 50° C. to about 120° C., using conventional or microwave heating, to form acids 1-3, esters 7-2, wherein $L^1$, Het, and Ar$^1$ are as previously disclosed, or amines 1-1 (Scheme 7, steps a, b, or c). The esters 7-2 may then be converted into acids 1-3, by treatment with a strong base such as sodium hydroxide or potassium hydroxide or lithium hydroxide, in a suitable solvent such as methanol, at temperatures from about 0° C. to about 50° C. (Scheme 7, step d).

Scheme 7

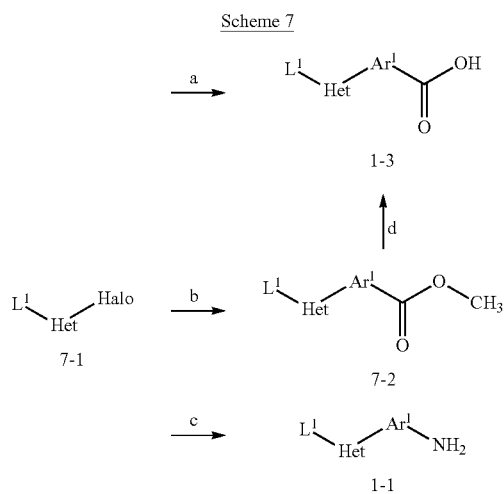

Preparation of Halo-Heterocycles

Methods for preparation of the halo-heterocycles 7-1 required for preparation of molecules of Formula One are described in Scheme 8. The coupling of halo-heterocycles 8-1, wherein LG is Cl, Br, I, mesylate, or tosylate, and $L^1$ is as previously disclosed, with halo-heterocycles 8-2, wherein Het is as previously disclosed, and the Het has a nucleophilic center, may be accomplished by treated the mixture with a base, such as such as cesium carbonate or potassium carbonate, in a suitable solvent, such as acetonitrile to form halo-heterocycles 7-1.

Scheme 8

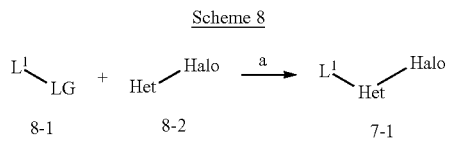

EXAMPLES

These examples are for illustration purposes and are not to be construed as limiting this disclosure to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Examples using "room temperature" were conducted in climate controlled laboratories with temperatures ranging from about 20° C. to about 24° C. Molecules are given their known names, named according to naming programs within ISIS Draw, ChemDraw, or ACD Name Pro. If such programs are unable to name a molecule, such molecule is named using conventional naming rules. $^1$H NMR spectral data are in ppm (δ) and were recorded at 300, 400, 500, or 600 MHz; $^{13}$C NMR spectral data are in ppm (δ) and were recorded at 75, 100, or 150 MHz, and $^{19}$F NMR spectral data are in ppm (δ) and were recorded at 376 MHz, unless otherwise stated.

Example 1

Preparation of 3-bromo-1-(4-(trifluoromethoxy)phenethyl)-1H-1,2,4-triazole (C1)

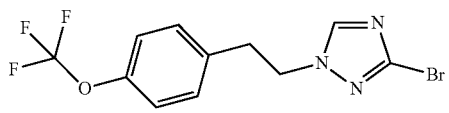

To a suspension of 3-bromo-1H-1,2,4-triazole (0.500 g, 3.38 mmol) and cesium carbonate (1.10 g, 3.38 mmol) in acetonitrile (6.8 mL) was added 1-(2-bromoethyl)-4-(trifluoromethoxy)benzene (0.909 g, 3.38 mmol). The reaction mixture was stirred at room temperature for 3 days. The solution was diluted with dichloromethane and washed with water. The organic extracts were washed with brine, dried, filtered, and concentrated. Purification by flash column chromatography using 0-100% ethyl acetate/hexanes as eluent provided the title compound as a colorless oil (0.410 g, 36%): $^1$H NMR (400 MHz, CDCl$_3$) δ 7.66 (s, 1H), 7.15 (dq, J=7.7, 1.0 Hz, 2H), 7.12-7.04 (m, 2H), 4.39-4.28 (m, 2H), 3.19 (t, J=7.0 Hz, 2H); $^{19}$F NMR (376 MHz, CDCl$_3$) δ −57.93; ESIMS m/z 337 ([M+H]$^+$).

Example 2

Preparation of 4-(1-(4-(trifluoromethoxy)phenethyl)-1H-1,2,4-triazol-3-yl)aniline (C2)

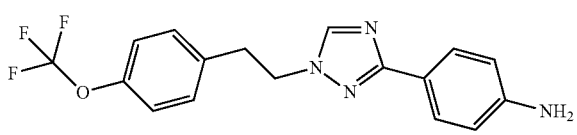 [SMILES: Nc1ccc(-c2ncn(CCc3ccc(OC(F)(F)F)cc3)n2)cc1]

To a 5 mL microwave vial were added 3-bromo-1-(4-(trifluoromethoxy)phenethyl)-1H-1,2,4-triazole (C1) (0.408 g, 1.21 mmol), 4-(4,4,5,5-tetramethyl-1,3,2-dioxaborolan-2-yl)aniline (0.293 g, 1.34 mmol), potassium fluoride (0.183 g, 3.16 mmol), bis(triphenylphosphine)palladium(II) dichloride (0.0850 g, 0.121 mmol), acetonitrile (8.1 mL), and water (8.1 mL). The vial was capped and heated at 115° C. for 15 minutes in a Biotage Initiator® microwave reactor, with external IR-sensor temperature monitoring from the side of the vessel. The reaction mixture was cooled to room temperature and diluted with dichloromethane and water. The organic layer was collected using a phase separator and concentrated. Purification by flash column chromatography using 0-100% ethyl acetate/B, where B is dichloromethane/hexanes (1:1), as eluent provided the title compound as a brown solid (0.150 g, 35%): mp 115-125° C.; $^1$H NMR (400 MHz, CDCl$_3$) δ 7.96-7.86 (m, 2H), 7.73 (s, 1H), 7.16-7.02 (m, 4H), 6.80-6.69 (m, 2H), 4.36 (t, J=6.9 Hz, 2H), 3.82 (s, 2H), 3.23 (t, J=7.0 Hz, 2H); $^{19}$F NMR (376 MHz, CDCl$_3$) δ −57.91; ESIMS m/z 349 ([M+H]$^+$).

Example 3

Preparation of (Z)-1-(3-(2-isopropyl-5-methylphenyl)-4-oxothiazolidin-2-ylidene)-3-(4-(1-(4-(trifluoromethoxy)phenethyl)-1H-1,2,4-triazol-3-yl)phenyl) urea (F1)

To 4-(1-(4-(trifluoromethoxy)phenethyl)-1H-1,2,4-triazol-3-yl)aniline (C2) (0.0600 g, 0.172 mmol) in acetonitrile (4 mL) was added 4-nitrophenyl chloroformate (0.0347 g, 0.172 mmol) in acetonitrile (0.3 mL). The reaction mixture was stirred at room temperature for 45 minutes. To this mixture were added 2-imino-3-(2-isopropyl-5-methylphenyl)thiazolidin-4-one (0.0428 g, 0.172 mmol), cesium carbonate (0.0561 g, 0.172 mmol), and N,N-diisopropylethylamine (0.0600 mL, 0.345 mmol). The reaction mixture was stirred at room temperature for 3 hours, was diluted with ethyl acetate and was washed with brine. The brine was extracted with ethyl acetate. The organic layers were dried over sodium sulfate, filtered, and concentrated. Purification by flash column chromatography 0-100% ethyl acetate/B, where B is dichloromethane/hexanes (1:1), as eluent provided the title compound as an off-white solid (0.0750 g, 69%).

Example 4

Preparation of 3-bromo-1-(4,4,4-trifluorobutyl)-1H-1,2,4-triazole (C3)

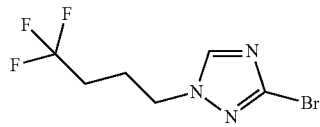

To a suspension of 3-bromo-1H-1,2,4-triazole (5.0 g, 34 mmol) and cesium carbonate (11 g, 34 mmol) in acetonitrile (50 mL) was added 1,1,1-trifluoro-4-iodobutane (6.8 mL, 34 mmol). The solution was stirred at room temperature for 72 hours. The solution was poured into water (50 mL) and extracted with diethyl ether (2×100 mL). The combined organic layers were concentrated. Purification by flash column chromatography using 0-20% ethyl acetate/hexanes as eluent, provided the title compound as a 70:30 mixture of

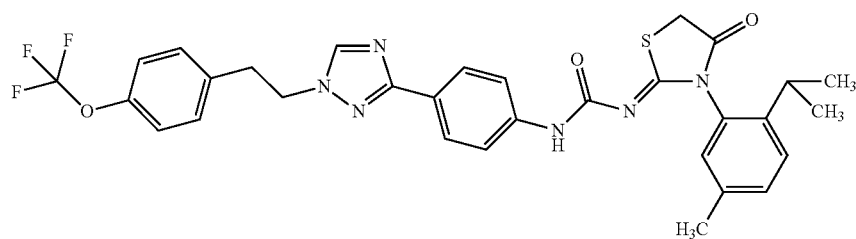 [SMILES: Cc1ccc(C(C)C)c(N2C(=O)CS/C2=N\C(=O)Nc2ccc(-c3ncn(CCc4ccc(OC(F)(F)F)cc4)n3)cc2)c1]

isomers (3.2 g, 37%). The mixture was used in the next step without further purification: $^1$H NMR (400 MHz, CDCl$_3$) δ 7.96 (s, 1H), 4.22 (t, J=6.5 Hz, 2H), 2.27-2.07 (m, 4H); $^{19}$F NMR (376 MHz, CDCl$_3$) δ −65.83.

The following compounds were prepared in like manner to the procedure outlined in Example 4:

3-Bromo-1-(3,3,4,4,5,5,5-heptafluoropentyl)-1H-1,2,4-triazole (C4)

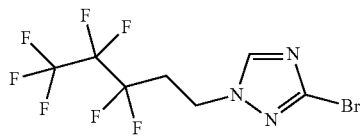 [SMILES: FC(F)(F)C(F)(F)C(F)(F)CCn1cnc(Br)n1]

Isolated as a light-brown liquid (3.5 g, 33%): $^1$H NMR (400 MHz, CDCl$_3$) δ 8.02 (s, 1H), 4.56-4.45 (m, 2H), 2.84-2.66 (m, 2H); ESIMS m/z 344 ([M+H]$^+$).

3-Bromo-1-(5,5,5-trifluoropentyl)-1H-1,2,4-triazole (C5)

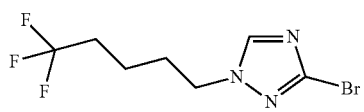 [SMILES: FC(F)(F)CCCCn1cnc(Br)n1]

Isolated as a light-brown liquid (4.0 g, 50%): $^1$H NMR (300 MHz, DMSO-d$_6$) δ 8.58 (s, 1H), 4.23-4.18 (m, 2H), 2.38-2.08 (m, 2H), 1.90-1.74 (m, 2H), 1.58-1.50 (m, 2H); ESIMS m/z 272 ([M+H]$^+$).

3-Bromo-1-(4-(trifluoromethyl)benzyl)-1H-1,2,4-triazole (C6)

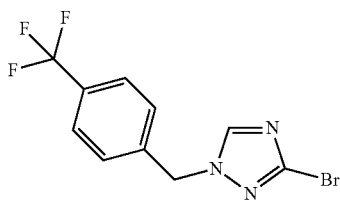 [SMILES: FC(F)(F)c1ccc(Cn2cnc(Br)n2)cc1]

Isolated as an off-white solid (10.0 g, 81%): $^1$H NMR (300 MHz, CDCl$_3$) δ 7.98 (s, 1H), 7.65 (d, J=7.5 Hz, 2H), 7.40 (d, J=8.1 Hz, 2H), 5.36 (s, 2H); ESIMS m/z 306 ([M+H]$^+$).

3-Bromo-1-(4,4,5,5,5-pentafluoropentyl)-1H-1,2,4-triazole (C7)

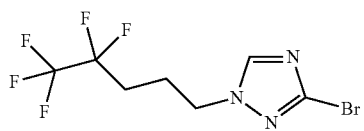 [SMILES: FC(F)(F)C(F)(F)CCCn1cnc(Br)n1]

Prepared using 4,4,5,5,5-pentafluoropentyl methanesulfonate and isolated as a light-brown liquid (3.5 g, 49%): $^1$H NMR (400 MHz, CDCl$_3$) δ 7.90 (s, 1H), 4.32-4.30 (m, 2H), 2.27-2.00 (m, 4H); ESIMS m/z 308 ([M+H]$^+$).

Example 5

Preparation of methyl 4-(1-(4,4,4-trifluorobutyl)-1H-1,2,4-triazol-3-yl)benzoate (C8)

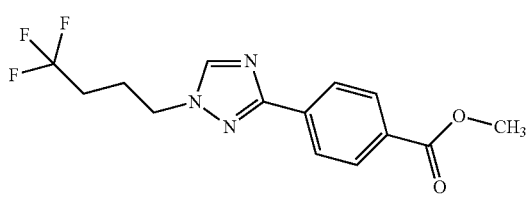 [SMILES: COC(=O)c1ccc(-c2ncn(CCCC(F)(F)F)n2)cc1]

To a microwave vial (25 mL) were added 3-bromo-1-(4,4,4-trifluorobutyl)-1H-1,2,4-triazole (C3) (1.00 g, 3.88 mmol), methyl 4-(4,4,5,5-tetramethyl-1,3,2-dioxaborolan-2-yl)benzoate (1.02 g, 3.88 mmol), tetrakis(triphenylphosphine)palladium(O) (0.448 g, 0.388 mmol), sodium bicarbonate (0.977 g, 11.6 mmol), dioxane (12 mL), and water (3.0 mL). The vial was heated at 140° C. for 30 minutes in a Biotage Initiator® microwave reactor, with external IR-sensor temperature monitoring from the side of the vessel. The solution was cooled, diluted with ethyl acetate, and washed with water. The organic layer was separated, dried, filtered, and concentrated. Purification by flash column chromatography using 0-70% ethyl acetate/hexanes as eluent provided the title compound mixed with excess triphenylphosphine oxide as a white solid (0.396 g, 14%): $^1$H NMR (400 MHz, CDCl$_3$) δ 8.20-8.15 (m, 2H), 8.13-8.11 (m, 3H), 4.29 (t, J=6.6 Hz, 2H), 3.94 (s, 3H), 2.33-2.09 (m, 4H); $^{19}$F NMR (376 MHz, CDCl$_3$) δ −65.81, −65.84; ESIMS m/z 313 ([M+H]$^+$).

The following compounds were prepared in like manner to the procedure outlined in Example 5:

Methyl 4-(1-(3,3,4,4,5,5,5-heptafluoropentyl)-1H-1,2,4-triazol-3-yl)benzoate (C9)

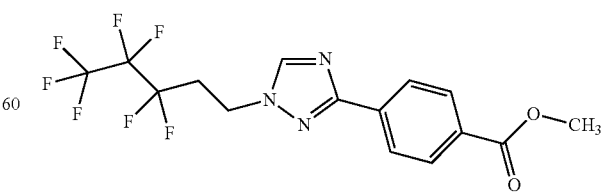

Isolated as a light-brown liquid and a mixture of isomers (1.5 g, 43%): ESIMS m/z 400 ([M+H]$^+$).

Methyl 4-(1-(5,5,5-trifluoropentyl)-1H-1,2,4-triazol-3-yl)benzoate (C10)

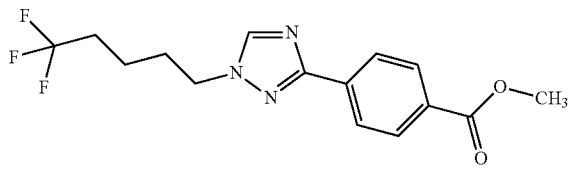 [SMILES: COC(=O)c1ccc(-c2ncn(CCCCC(F)(F)F)n2)cc1]

Isolated as a light-brown liquid and a mixture of isomers (3.5 g, 73%): ¹H NMR (400 MHz, CDCl₃), mixture of two isomers: δ 8.17 (d, J=8.0 Hz, 2H), 8.11 (d, J=8.4 Hz, 2H), 4.26-4.24 (m, 2H), 3.94 (s, 3H), 2.20-2.16 (m, 2H), 2.14-2.00 (m, 2H), 1.68-1.64 (m, 2H); ESIMS m/z 328 ([M+H]⁺).

Methyl 4-(1-(4-(trifluoromethyl)benzyl)-1H-1,2,4-triazol-3-yl)benzoate (C11)

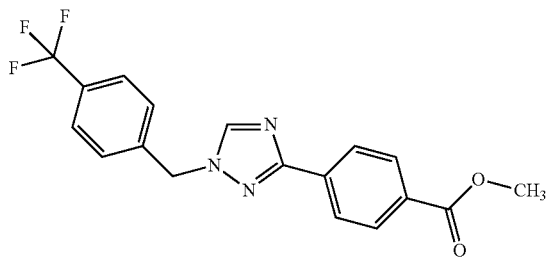 [SMILES: COC(=O)c1ccc(-c2ncn(Cc3ccc(C(F)(F)F)cc3)n2)cc1]

Isolated as an off-white solid (2.5 g, 71%): ¹H NMR (400 MHz, CDCl₃) δ 8.18-8.16 (m, 3H), 8.11 (d, J=8.4 Hz, 2H), 7.65 (d, J=8.0 Hz, 2H), 7.42 (d, J=7.6 Hz, 2H), 5.6 (s, 2H), 3.94 (s, 3H); ESIMS m/z 362 ([M+H]⁺).

Methyl 4-(1-(4,4,5,5,5-pentafluoropentyl)-1H-1,2,4-triazol-3-yl)benzoate (C12)

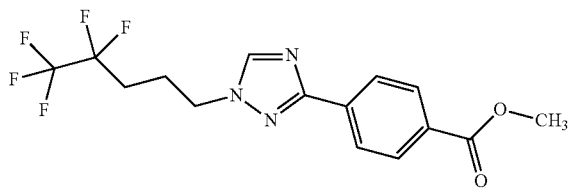 [SMILES: COC(=O)c1ccc(-c2ncn(CCCC(F)(F)C(F)(F)F)n2)cc1]

Isolated as a light-brown liquid (1.5 g, 51%): ESIMS m/z 364 ([M+H]⁺).

Example 6

Preparation of 4-(1-(4,4,4-trifluorobutyl)-1H-1,2,4-triazol-3-yl)benzoic acid (C13)

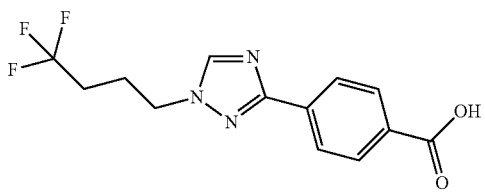 [SMILES: O=C(O)c1ccc(-c2ncn(CCCC(F)(F)F)n2)cc1]

To a solution of methyl 4-(1-(4,4,4-trifluorobutyl)-1H-1,2,4-triazol-3-yl)benzoate (C8) (0.396 g, 1.26 mmol) in methanol (6 mL) was added sodium hydroxide (2 N, 3.60 mL, 7.20 mmol). The solution was stirred at room temperatures for 18 hours, then it was acidified (pH 1) using hydrochloric acid (1 N). The solution was extracted with ethyl acetate and washed with water. The organic layer was dried, filtered, and concentrated to provide the title compound as a light-yellow solid (0.354 g, 88%): ¹H NMR (400 MHz, DMSO-d₆) δ 8.66 (s, 1H), 8.19-7.96 (m, 4H), 4.34 (t, J=7.0 Hz, 2H), 2.45-2.20 (m, 2H), 2.14-2.01 (m, 2H); ¹⁹F NMR (376 MHz, DMSO-d₆) 5-64.78; ESIMS m/z 299 ([M+H]⁺).

The following compounds were prepared in like manner to the procedure outlined in Example 6:

4-(1-(3,3,4,4,5,5,5-Heptafluoropentyl)-1H-1,2,4-triazol-3-yl)benzoic acid (C14)

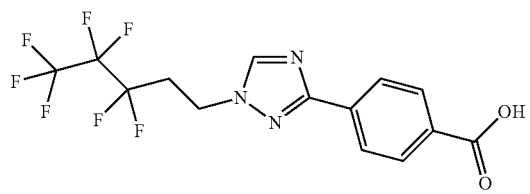 [SMILES: O=C(O)c1ccc(-c2ncn(CCC(F)(F)C(F)(F)C(F)(F)F)n2)cc1]

Isolated as an off-white solid (0.7 g, 49%): mp 186-190° C.; ¹H NMR (300 MHz, DMSO-d₆) δ 13.05 (br s, 1H), 8.72 (s, 1H), 8.12 (d, J=8.4 Hz, 2H), 8.03 (d, J=8.4 Hz, 2H), 4.64 (t, J=6.9 Hz, 2H), 3.10-2.90 (m, 2H); ESIMS m/z 386 ([M+H]⁺).

4-(1-(5,5,5-Trifluoropentyl)-1H-1,2,4-triazol-3-yl)benzoic acid (C15)

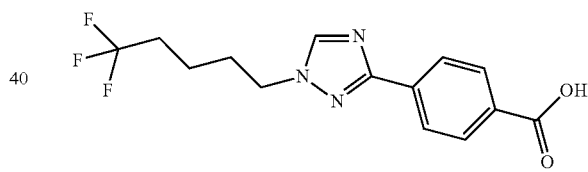

Isolated as an off-white solid (3.5 g, 73%): ¹H (0.85 g, 59%): mp 140-142° C.; ¹H NMR (300 MHz, DMSO-d₆) δ 13.10 (br s, 1H), 8.65 (s, 1H), 8.10 (d, J=8.4 Hz, 2H), 8.03 (d, J=8.4 Hz, 1H), 7.84 (d, J=8.4 Hz, 1H), 4.33-4.27 (m, 2H), 2.37-2.17 (m, 2H), 1.95-1.84 (m, 2H), 1.54-1.40 (m, 2H); ESIMS m/z 314 ([M+H]⁺).

4-(1-(4-(Trifluoromethyl)benzyl)-1H-1,2,4-triazol-3-yl)benzoic acid (C16)

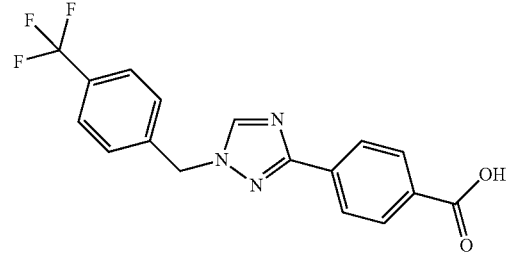 [SMILES: O=C(O)c1ccc(-c2ncn(Cc3ccc(C(F)(F)F)cc3)n2)cc1]

Isolated as an off-white solid (1.7 g, 71%): mp 204-206° C.; ESIMS m/z 348 ([M+H]⁺).

4-(1-(4,4,5,5,5-Pentafluoropentyl)-1H-1,2,4-triazol-3-yl)benzoic acid (C17)

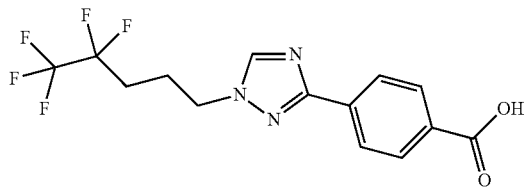 [SMILES: O=C(O)c1ccc(-c2ncn(CCCC(F)(F)C(F)(F)F)n2)cc1]

Isolated as an off-white solid (0.65 g, 45%): mp 148-150° C.; $^1$H NMR (300 MHz, DMSO-d$_6$) δ 13.05 (br s, 1H), 8.66 (s, 1H), 8.11 (d, J=8.4 Hz, 2H), 8.03 (d, J=8.4 Hz, 2H), 4.36 (t, J=7.05 Hz, 2H), 2.40-2.22 (m, 2H), 2.18-2.00 (m, 2H); ESIMS m/z 350 ([M+H]$^+$).

Example 7

Preparation of 4-(1-(4,4,4-trifluorobutyl)-1H-1,2,4-triazol-3-yl)benzoyl azide (C18)

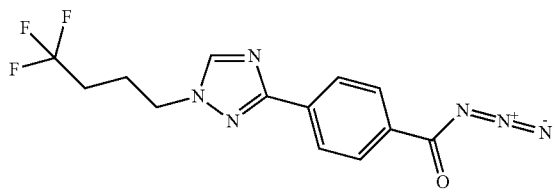 [SMILES: N=[N+]=NC(=O)c1ccc(-c2ncn(CCCC(F)(F)F)n2)cc1]

To a solution of 4-(1-(4,4,4-trifluorobutyl)-1H-1,2,4-triazol-3-yl)benzoic acid (C13) (0.354 g, 1.18 mmol) in toluene (7 mL) was added triethylamine (0.165 mL, 1.18 mmol) followed by diphenylphosphoryl azide (0.254 mL, 1.18 mmol). The solution was stirred at room temperature for 1 hour, then the solvent was concentrated to ½ volume, and the remaining solution was adsorbed onto silica gel. Purification by flash column chromatography using 0-100% ethyl acetate/hexanes as eluent, provided the title compound as a white solid (0.158 g, 41%): $^1$H NMR (400 MHz, CDCl$_3$) δ 8.22-8.17 (m, 2H), 8.13 (s, 1H), 8.12-8.08 (m, 2H), 4.31 (t, J=6.6 Hz, 2H), 2.32-2.12 (m, 4H); $^{19}$F NMR (376 MHz, CDCl$_3$) δ −65.83.

The following compounds were prepared in like manner to the procedure outlined in Example 7:

4-(1-(3,3,4,4,5,5,5-Heptafluoropentyl)-1H-1,2,4-triazol-3-yl)benzoyl azide (C19)

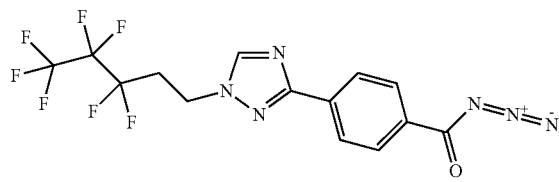 [SMILES: N=[N+]=NC(=O)c1ccc(-c2ncn(CCC(F)(F)C(F)(F)C(F)(F)F)n2)cc1]

Isolated as an off-white solid (0.2 g, 47%): $^1$H NMR (400 MHz, CDCl$_3$) δ 8.18 (m, 3H), 8.10 (d, J=8.4 Hz, 2H), 4.55 (t, J=7.2 Hz, 2H), 2.88-2.78 (m, 2H); ESIMS m/z 411 ([M+H]$^+$).

4-(1-(5,5,5-Trifluoropentyl)-1H-1,2,4-triazol-3-yl)benzoyl azide (C20)

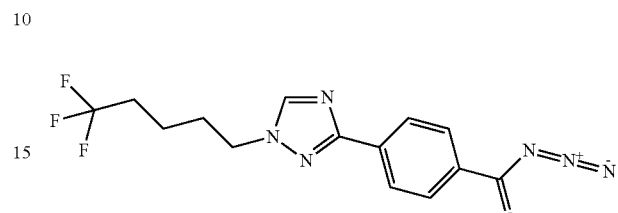

Isolated as an off-white solid (0.2 g, 31%): $^1$H NMR (300 MHz, CDCl$_3$) δ 8.20-8.08 (m, 5H), 4.24 (t, J=6.7 Hz, 2H), 2.20-1.98 (m, 4H), 1.68-1.58 (m, 2H).

4-(1-(4-(Trifluoromethyl)benzyl)-1H-1,2,4-triazol-3-yl)benzoyl azide (C21)

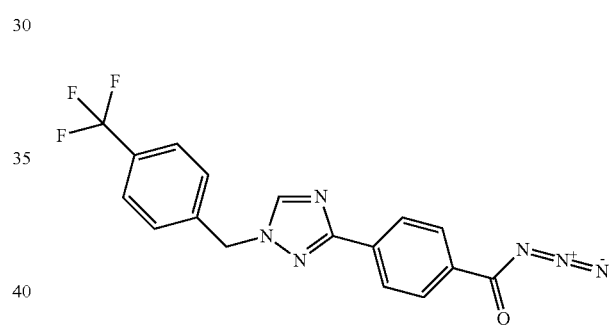

Isolated as an off-white solid (0.7 g, 44%): $^1$H NMR (400 MHz, CDCl$_3$) δ 8.21-8.16 (m, 3H), 8.09 (d, J=8.4 Hz, 2H), 7.65 (d, J=7.6 Hz, 2H), 7.42 (d, J=8.4 Hz, 2H), 5.46 (s, 2H); ESIMS m/z 373 ([M+H]$^+$).

4-(1-(4,4,5,5,5-Pentafluoropentyl)-1H-1,2,4-triazol-3-yl)benzoyl azide (C22)

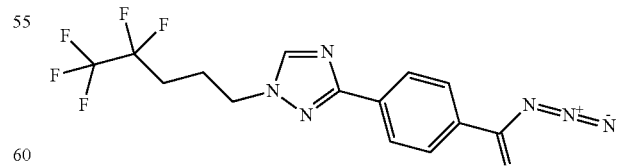

Isolated as an off-white solid (0.17 g, 32%): $^1$H NMR (300 MHz, CDCl$_3$) δ 8.20 (d, J=8.7 Hz, 2H), 8.14-8.09 (m, 3H), 4.32 (t, J=6.6 Hz, 2H), 2.34-2.15 (m, 4H); ESIMS m/z 375 ([M+H]$^+$).

Example 8

Preparation of (Z)-1-(3-(2-isopropyl-5-methylphenyl)-4-oxothiazolidin-2-ylidene)-3-(4-(1-(4,4,4-trifluorobutyl)-1H-1,2,4-triazol-3-yl)phenyl)urea (F6)

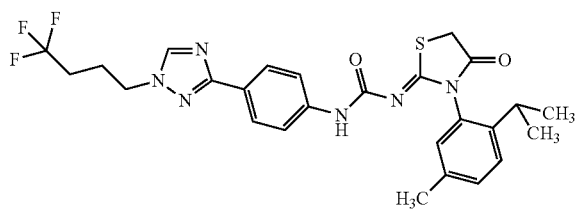 [SMILES: Cc1ccc(C(C)C)c(N2C(=O)CS/C2=N\C(=O)Nc2ccc(-c3ncn(CCCC(F)(F)F)n3)cc2)c1]

A solution of 4-(1-(4,4,4-trifluorobutyl)-1H-1,2,4-triazol-3-yl)benzoyl azide (C18) (0.158 g, 0.487 mmol) in acetonitrile (6.00 mL) was heated at 70° C. for 2 hours. The solution was cooled, and 1-(2-isopropyl-5-methylphenyl)thiourea (0.102 g, 0.487 mmol) and cesium carbonate (0.175 g, 0.536 mmol) were added. The solution was stirred for 18 hours at room temperature and diluted in ethanol (6 mL). Sodium acetate (0.120 g, 1.46 mmol) and methyl bromoacetate (0.149 g, 0.980 mmol) were added, and the solution was heated at 60° C. for 3 hours. The reaction mixture was cooled and concentrated. Purification by reverse-phase HPLC using acetonitrile/water as eluent provided the title compound as a yellow solid (0.101 g, 35%).

The following compounds were prepared in like manner to the procedure outlined in Example 8:

(Z)-1-(3-(2-Isopropylphenyl)-4-oxothiazolidin-2-ylidene)-3-(4-(1-(4,4,5,5,5-pentafluoropentyl)-1H-1,2,4-triazol-3-yl)phenyl)urea (F2)

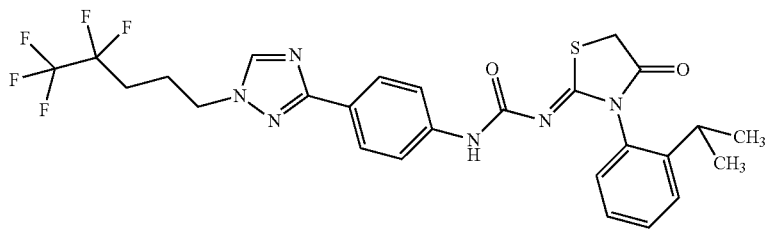 [SMILES: CC(C)c1ccccc1N1C(=O)CS/C1=N\C(=O)Nc1ccc(-c2ncn(CCCC(F)(F)C(F)(F)F)n2)cc1]

Isolated as a light-brown solid (0.07 g, 45%).

(Z)-1-(3-(2-Isopropylphenyl)-4-oxothiazolidin-2-ylidene)-3-(4-(1-(4-(trifluoromethyl)benzyl)-1H-1,2,4-triazol-3-yl)phenyl)urea (F3)

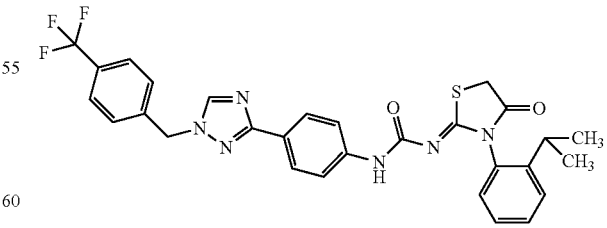

Isolated as an off-white solid (0.05 g, 33%).

(Z)-1-(3-(2-Isopropylphenyl)-4-oxothiazolidin-2-ylidene)-3-(4-(1-(5,5,5-trifluoropentyl)-1H-1,2,4-triazol-3-yl)phenyl)urea (F4)

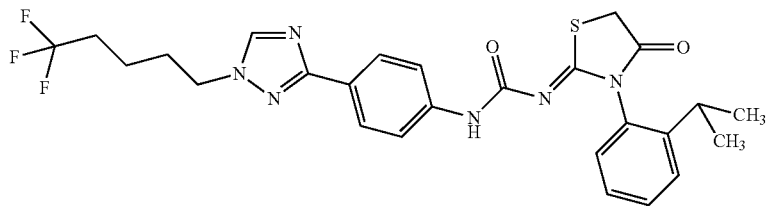 [SMILES: CC(C)c1ccccc1N1C(=O)CS/C1=N\C(=O)Nc1ccc(-c2ncn(CCCCC(F)(F)F)n2)cc1]

Isolated as an off-white solid (0.085 g, 33%).

Example 9

Preparation of (Z)-1-(4-(1-(3,3,4,4,5,5,5-heptafluoropentyl)-1H-1,2,4-triazol-3-yl)phenyl)-3-(3-(2-isopropylphenyl)-4-oxothiazolidin-2-ylidene)urea (F5)

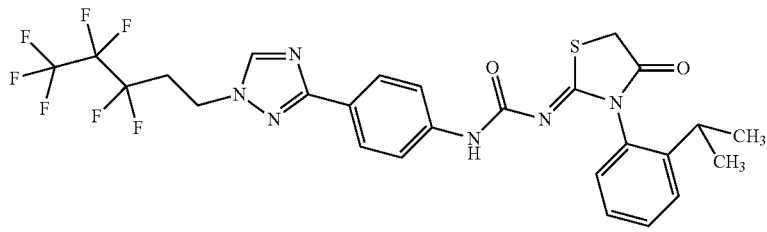 [SMILES: CC(C)c1ccccc1N1C(=O)CS/C1=N\C(=O)Nc1ccc(-c2ncn(CCC(F)(F)C(F)(F)C(F)(F)F)n2)cc1]

A stirred solution of 4-(1-(3,3,4,4,5,5,5-heptafluoropentyl)-1H-1,2,4-triazol-3-yl)benzoyl azide (C19) (0.200 g, 0.487 mmol) and 2-imino-3-(2-isopropylphenyl)thiazolidin-4-one (0.137 g, 0.585 mmol) in toluene (4 mL) was heated at 100° C. for 2 hours. The reaction mixture was cooled to room temperature. The resultant solid was filtered and washed with n-pentane to provide the title compound as an off-white solid (0.100 g, 33%).

It is recognized that some reagents and reaction conditions may not be compatible with certain functionalities that may be present in certain molecules of Formula One or certain molecules used in the preparation of certain molecules of Formula One. In such cases, it may be necessary to employ standard protection and deprotection protocols comprehensively reported in the literature and well known to a person skilled in the art. In addition, in some cases it may be necessary to perform further routine synthetic steps not described herein to complete the synthesis of desired molecules. A person skilled in the art will also recognize that it may be possible to achieve the synthesis of desired molecules by performing some of the steps of the synthetic routes in a different order to that described. A person skilled in the art will also recognize that it may be possible to perform standard functional group interconversions or substitution reactions on desired molecules to introduce or modify substituents.

Biological Assays

The following bioassays against Beet Armyworm (*Spodoptera exigua*), Cabbage Looper (*Trichoplusia ni*), and Yellow Fever Mosquito (*Aedes aegypti*), are included herein due to the damage they inflict. Furthermore, the Beet Armyworm and Cabbage Looper are two good indicator species for a broad range of chewing pests. Additionally, the Green Peach Aphid is a good indicator species for a broad range of sap-feeding pests. The results with these four indicator species along with the Yellow Fever Mosquito show the broad usefulness of the molecules of Formula One in controlling pests in Phyla Arthropoda, Mollusca, and Nematoda (Drewes et al.)

Example A

Bioassays on Beet Armyworm (Spodoptera exigua, LAPHEG) ("BAW") and Cabbage Looper (Trichoplusia ni, TRIPNI) ("CL")

Beet armyworm is a serious pest of economic concern for alfalfa, asparagus, beets, citrus, corn, cotton, onions, peas, peppers, potatoes, soybeans, sugar beets, sunflowers, tobacco, and tomatoes, among other crops. It is native to Southeast Asia but is now found in Africa, Australia, Japan, North America, and Southern Europe. The larvae may feed in large swarms causing devastating crop losses. It is known to be resistant to several pesticides.

Cabbage looper is a serious pest found throughout the world. It attacks alfalfa, beans, beets, broccoli, Brussel sprouts, cabbage, cantaloupe, cauliflower, celery, collards, cotton, cucumbers, eggplant, kale, lettuce, melons, mustard, parsley, peas, peppers, potatoes, soybeans, spinach, squash, tomatoes, turnips, and watermelons, among other crops.

This species is very destructive to plants due to its voracious appetite. The larvae consume three times their weight in food daily. The feeding sites are marked by large accumulations of sticky, wet, fecal material, which may contribute to higher disease pressure thereby causing secondary problems on the plants in the site. It is known to be resistant to several pesticides.

Consequently, because of the above factors control of these pests is important. Furthermore, molecules that control these pests (BAW and CL), which are known as chewing pests, will be useful in controlling other pests that chew on plants.

Certain molecules disclosed in this document were tested against BAW and CL using procedures described in the following examples. In the reporting of the results, the "BAW & CL Rating Table" was used (See Table Section).

Bioassays on BAW

Bioassays on BAW were conducted using a 128-well diet tray assay. One to five second instar BAW larvae were placed in each well (3 mL) of the diet tray that had been previously filled with 1 mL of artificial diet to which 50 $\mu g/cm^2$ of the test molecule (dissolved in 50 µL of 90:10 acetone-water mixture) had been applied (to each of eight wells) and then allowed to dry. Trays were covered with a clear self-adhesive cover, vented to allow gas exchange, and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Bioassays on CL

Bioassays on CL were conducted using a 128-well diet tray assay. One to five second instar CL larvae were placed in each well (3 mL) of the diet tray that had been previously filled with 1 mL of artificial diet to which 50 $\mu g/cm^2$ of the test molecule (dissolved in 50 µL of 90:10 acetone-water mixture) had been applied (to each of eight wells) and then allowed to dry. Trays were covered with a clear self-adhesive cover, vented to allow gas exchange, and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Example B

Bioassays on Yellow Fever Mosquito (Aedes aegypti, AEDSAE) ("YFM")

YFM prefers to feed on humans during the daytime and is most frequently found in or near human habitations. YFM is a vector for transmitting several diseases. It is a mosquito that can spread the dengue fever and yellow fever viruses. Yellow fever is the second most dangerous mosquito-borne disease after malaria. Yellow fever is an acute viral hemorrhagic disease and up to 50% of severely affected persons without treatment will die from yellow fever. There are an estimated 200,000 cases of yellow fever, causing 30,000 deaths worldwide each year. Dengue fever is a nasty, viral disease; it is sometimes called "breakbone fever" or "breakheart fever" because of the intense pain it can produce. Dengue fever kills about 20,000 people annually. Consequently, because of the above factors control of this pest is important. Furthermore, molecules that control this pest (YFM), which is known as a sucking pest, are useful in controlling other pests that cause human and animal suffering.

Certain molecules disclosed in this document were tested against YFM using procedures described in the following paragraph. In the reporting of the results, the "YFM Rating Table" was used (See Table Section).

Master plates containing 400 µg of a molecule dissolved in 100 µL of dimethyl sulfoxide (DMSO) (equivalent to a 4000 ppm solution) are used. A master plate of assembled molecules contains 15 µL per well. To this plate, 135 µL of a 90:10 water/acetone mixture is added to each well. A robot (Biomek® NXP Laboratory Automation Workstation) is programmed to dispense 15 µL aspirations from the master plate into an empty 96-well shallow plate ("daughter" plate). There are 6 reps ("daughter" plates) created per master. The created "daughter" plates are then immediately infested with YFM larvae.

The day before plates are to be treated, mosquito eggs are placed in Millipore water containing liver powder to begin hatching (4 g into 400 mL). After the "daughter" plates are created using the robot, they are infested with 220 µL of the liver powder/larval mosquito mixture (about 1 day-old larvae). After plates are infested with mosquito larvae, a non-evaporative lid is used to cover the plate to reduce drying. Plates are held at room temperature for 3 days prior to grading. After 3 days, each well is observed and scored based on mortality. The results are indicated in the table entitled "Table ABC: Biological Results" (See Table Section).

Agriculturally Acceptable Acid Addition Salts, Salt Derivatives, Solvates, Ester Derivatives, Polymorphs, Isotopes, and Radionuclides Molecules of Formula One may be formulated into agriculturally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxyl-methanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One may be formulated into salt derivatives. By way of a non-limiting example, a salt derivative may be prepared by contacting a free base with a sufficient amount of the desired acid to produce a salt. A free base may be regenerated by treating the salt with a suitable dilute aqueous base solution such as dilute aqueous sodium hydroxide, potassium carbonate, ammonia, and sodium bicarbonate. As an example, in many cases, a pesticide, such as 2,4-D, is made more water-soluble by converting it to its dimethylamine salt.

Molecules of Formula One may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One containing an acid functionality may be made into ester derivatives. These ester derivatives can then be applied in the same manner as the molecules disclosed in this document are applied.

Molecules of Formula One may be made as various crystal polymorphs. Polymorphism is important in the development of agrochemicals since different crystal polymorphs or structures of the same molecule can have vastly different physical properties and biological performances.

Molecules of Formula One may be made with different isotopes. Of particular importance are molecules having $^2H$ (also known as deuterium) or $^3H$ (also known as tritium) in place of $^1H$. Molecules of Formula One may be made with different radionuclides. Of particular importance are molecules having $^{14}C$ (also known as radiocarbon). Molecules of Formula One having deuterium, tritium, or $^{14}C$ may be used in biological studies allowing tracing in chemical and physiological processes and half-life studies, as well as, MoA studies.

Combinations

In another embodiment of this invention, molecules of Formula One may be used in combination (such as, in a compositional mixture, or a simultaneous or sequential application) with one or more active ingredients.

In another embodiment of this invention, molecules of Formula One may be used in combination (such as, in a compositional mixture, or a simultaneous or sequential application) with one or more active ingredients each having a MoA that is the same as, similar to, but more likely—different from, the MoA of the molecules of Formula One.

In another embodiment, molecules of Formula One may be used in combination (such as, in a compositional mixture, or a simultaneous or sequential application) with one or more molecules having acaricidal, algicidal, avicidal, bactericidal, fungicidal, herbicidal, insecticidal, molluscicidal, nematicidal, rodenticidal, and/or virucidal properties.

In another embodiment, the molecules of Formula One may be used in combination (such as, in a compositional mixture, or a simultaneous or sequential application) with one or more molecules that are antifeedants, bird repellents, chemosterilants, herbicide safeners, insect attractants, insect repellents, mammal repellents, mating disrupters, plant activators, plant growth regulators, and/or synergists.

In another embodiment, molecules of Formula One may also be used in combination (such as in a compositional mixture, or a simultaneous or sequential application) with one or more biopesticides.

In another embodiment, in a pesticidal composition combinations of a molecule of Formula One and an active ingredient may be used in a wide variety of weight ratios. For example, in a two-component mixture, the weight ratio of a molecule of Formula One to an active ingredient, the weight ratios in Table B may be used. However, in general, weight ratios less than about 10:1 to about 1:10 are preferred. It is also preferred sometimes to use a three, four, five, six, seven, or more, component mixture comprising a molecule of Formula One and an additional two or more active ingredients.

Weight ratios of a molecule of Formula One to an active ingredient may also be depicted as X: Y; wherein X is the parts by weight of a molecule of Formula One and Y is the parts by weight of active ingredient. The numerical range of the parts by weight for X is $0<X\leq100$ and the parts by weight for Y is $0<Y\leq100$ and is shown graphically in TABLE C. By way of non-limiting example, the weight ratio of a molecule of Formula One to an active ingredient may be 20:1.

Ranges of weight ratios of a molecule of Formula One to an active ingredient may be depicted as $X_1:Y_1$ to $X_2:Y_2$, wherein X and Y are defined as above.

In one embodiment, the range of weight ratios may be $X_1:Y_1$ to $X_2:Y_2$, wherein $X_1>Y_1$ and $X_2<Y_2$. By way of non-limiting example, the range of a weight ratio of a molecule of Formula One to an active ingredient may be between 3:1 and 1:3, inclusive of the endpoints.

In another embodiment, the range of weight ratios may be $X_1:Y_1$ to $X_2:Y_2$, wherein $X_1>Y_1$ and $X_2>Y_2$. By way of non-limiting example, the range of weight ratio of a molecule of Formula One to an active ingredient may be between 15:1 and 3:1, inclusive of the endpoints.

In another embodiment, the range of weight ratios may be $X_1:Y_1$ to $X_2:Y_2$, wherein $X_1<Y_1$ and $X_2<Y_2$. By way of non-limiting example, the range of weight ratios of a molecule of Formula One to an active ingredient may be between about 1:3 and about 1:20, inclusive of the endpoints.

It is envisioned that certain weight ratios of a molecule of Formula One to an active ingredient, as presented in Table B and C, may be synergistic.

Formulations

A pesticide is many times not suitable for application in its pure form. It is usually necessary to add other substances so that the pesticide may be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra-low volume solutions.

Pesticides are applied most often as aqueous suspensions or emulsions prepared from concentrated formulations of such pesticides. Such water-soluble, water-suspendable, or emulsifiable formulations are either solids, usually known as wettable powders, water dispersible granules, liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may, also be added to increase the density and viscosity of the aqueous carrier. It is often most effective to grind and mix the pesticide at the same time by preparing the aqueous mixture and homogenizing it in an implement such as a sand mill, ball mill, or piston-type homogenizer. The pesticide in suspension might be microencapsulated in plastic polymer.

Oil dispersions (OD) comprise suspensions of organic solvent-insoluble pesticides finely dispersed in a mixture of organic solvent and emulsifiers at a concentration in the range from about 2% to about 50% by weight. One or more pesticide might be dissolved in the organic solvent. Useful organic solvents include aromatics, especially xylenes and petroleum fractions, especially the high-boiling naphthalenic and olefinic portions of petroleum such as heavy aromatic naphtha. Other solvents may include vegetable oils, seed oils, and esters of vegetable and seed oils. Suitable emulsifiers for oil dispersions are selected from conventional anionic and non-ionic surfactants. Thickeners or gelling agents are added in the formulation of oil dispersions to modify the rheology or flow properties of the liquid and to prevent separation and settling of the dispersed particles or droplets.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier, which has been pre-formed to the appropriate particle size, in the range of from about 0.5 mm to about 3 mm. Such compositions may also be formulated by making a dough or paste of the carrier and molecule, and then crushing and drying to obtain the desired granular particle size. Another form of granules is a water emulsifiable granule (EG). It is a formulation consisting of granules to be applied as a conventional oil-in-water emulsion of the active ingredient(s), either solubilized or diluted in an organic solvent, after disintegration and dissolution in water. Water emulsifiable granules comprise one or several active ingredient(s), either solubilized or diluted in a suitable organic solvent that is (are) absorbed in a water soluble polymeric shell or some other type of soluble or insoluble matrix.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. Dusts may be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions, the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait, they also consume the pesticide. Baits may take the form of granules, gels, flowable powders, liquids, or solids. Baits may be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings, or in special chambers.

Pesticides may be microencapsulated by suspending the pesticide particles or droplets in plastic polymers of various types. By altering, the chemistry of the polymer or by changing factors in the processing, microcapsules may be formed of various sizes, solubility, wall thicknesses, and degrees of penetrability. These factors govern the speed with which the active ingredient within is released, which in turn, affects the residual performance, speed of action, and odor of the product. The microcapsules might be formulated as suspension concentrates or water dispersible granules.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one molecule which is agriculturally active, and is individually coated with a monolamellar or oligolamellar layer comprising: (1) at least one non-ionic lipophilic surface-active agent, (2) at least one non-ionic hydrophilic surface-active agent, and (3) at least one ionic surface-active agent, wherein the globules having a mean particle diameter of less than 800 nanometers.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate, sodium dioctyl sulfosuccinate, alkyl phenol ethoxylates, and aliphatic alcohol ethoxylates.

A dispersing agent is a substance that adsorbs onto the surface of particles, helps to preserve the state of dispersion of the particles, and prevents them from reaggregating. Dispersing agents are added to agrochemical formulations to facilitate dispersion and suspension during manufacture, and to ensure the particles redisperse into water in a spray tank. They are widely used in wettable powders, suspension concentrates, and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium-naphthalene-sulfonate-formaldehyde-condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates, sodium naphthalene sulfonate formaldehyde condensates, tristyrylphenol-ethoxylate-phosphate-esters, aliphatic alcohol ethoxylates, alkyl ethoxylates, EO-PO block copolymers, and graft copolymers.

An emulsifying agent is a substance that stabilizes a suspension of droplets of one liquid phase in another liquid phase. Without the emulsifying agent, the two liquids would separate into two immiscible liquid phases. The most commonly used emulsifier blends contain an alkylphenol or an aliphatic alcohol with twelve or more ethylene oxide units and the oil-soluble calcium salt of dodecylbenzenesulfonic acid. A range of hydrophile-lipophile balance ("HLB") values from about 8 to about 18 will normally provide good stable emulsions. Emulsion stability can sometimes be improved by the addition of a small amount of an EO-PO block copolymer surfactant.

A solubilizing agent is a surfactant that will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates, linear aliphatic alcohol ethoxylates, and aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules, and water-dispersible granules.

Organic solvents are used mainly in the formulation of emulsifiable concentrates, oil-in-water emulsions, suspoemulsions, oil dispersions, and ultra-low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, oil dispersions, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate and oil dispersion formulations using clays and silicas. Examples of these types of materials, include, but are not limited to, montmorillonite, bentonite, magnesium aluminum silicate, and attapulgite. Water-soluble polysaccharides in water based suspension concentrates have been used as thickening-gelling agents for many years. The types of polysaccharides most commonly used are natural extracts of seeds and seaweeds or are synthetic derivatives of cellulose. Examples of these types of materials include, but are not limited to, guar gum, locust bean gum, carrageenam, alginates, methyl cellulose, sodium carboxymethyl cellulose (SCMC), and hydroxyethyl cellulose (HEC). Other types of anti-settling agents are based on modified starches, polyacrylates, polyvinyl alcohol, and polyethylene oxide. Another good anti-settling agent is xanthan gum.

Microorganisms can cause spoilage of formulated products. Therefore, preservation agents are used to eliminate or reduce their effect. Examples of such agents include, but are not limited to: propionic acid and its sodium salt, sorbic acid and its sodium or potassium salts, benzoic acid and its sodium salt, p-hydroxybenzoic acid sodium salt, methyl p-hydroxybenzoate, and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

Applications

Molecules of Formula One may be applied to any locus. Particular loci to apply such molecules include loci where alfalfa, almonds, apples, barley, beans, canola, corn, cotton, crucifers, flowers, fodder species (Rye Grass, Sudan Grass, Tall Fescue, Kentucky Blue Grass, and Clover), fruits, lettuce, oats, oil seed crops, oranges, peanuts, pears, peppers, potatoes, rice, sorghum, soybeans, strawberries, sugarcane, sugarbeets, sunflowers, tobacco, tomatoes, wheat (for example, Hard Red Winter Wheat, Soft Red Winter Wheat, White Winter Wheat, Hard Red Spring Wheat, and Durum Spring Wheat), and other valuable crops are growing or the seeds thereof are going to be planted.

Molecules of Formula One may also be applied where plants, such as crops, are growing and where there are low levels (even no actual presence) of pests that can commercially damage such plants. Applying such molecules in such locus is to benefit the plants being grown in such locus. Such benefits, may include, but are not limited to: helping the plant grow a better root system; helping the plant better withstand stressful growing conditions; improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

Molecules of Formula One may be applied with ammonium sulfate when growing various plants as this may provide additional benefits.

Molecules of Formula One may be applied on, in, or around plants genetically modified to express specialized traits, such as *Bacillus thuringiensis* (for example, Cry1Ab, Cry1Ac, Cry1Fa, Cry1A.105, Cry2Ab, Vip3A, mCry3A, Cry3Ab, Cry3Bb, Cry34Ab1/Cry35Ab1), other insecticidal toxins, or those expressing herbicide tolerance, or those with "stacked" foreign genes expressing insecticidal toxins, herbicide tolerance, nutrition-enhancement, or any other beneficial traits.

Molecules of Formula One may be applied to the foliar and/or fruiting portions of plants to control pests. Either such molecules will come in direct contact with the pest, or the pest will consume such molecules when eating the plant or while extracting sap or other nutrients from the plant.

Molecules of Formula One may also be applied to the soil, and when applied in this manner, root and stem feeding pests may be controlled. The roots may absorb such molecules thereby taking it up into the foliar portions of the plant to control above ground chewing and sap feeding pests.

Systemic movement of pesticides in plants may be utilized to control pests on one portion of the plant by applying (for example by spraying a locus) a molecule of Formula One to a different portion of the plant. For example, control of foliar-feeding insects may be achieved by drip irrigation or furrow application, by treating the soil with for example pre- or post-planting soil drench, or by treating the seeds of a plant before planting.

Molecules of Formula One may be used with baits. Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait.

Molecules of Formula One may be encapsulated inside, or placed on the surface of a capsule. The size of the capsules can range from nanometer size (about 100-900 nanometers in diameter) to micrometer size (about 10-900 microns in diameter).

Molecules of Formula One may be applied to eggs of pests. Because of the unique ability of the eggs of some pests to resist certain pesticides, repeated applications of such molecules may be desirable to control newly emerged larvae.

Molecules of Formula One may be applied as seed treatments. Seed treatments may be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide tolerance, such as "Roundup Ready" seed, or those with "stacked" foreign genes expressing insecticidal toxins, herbicide tolerance, nutrition-enhancement, drought tolerance, or any other beneficial traits. Furthermore, such seed treatments with molecules of Formula One may further enhance the ability of a plant to withstand stressful growing conditions better. This results in a healthier, more vigorous plant, which can lead to higher yields at harvest time. Generally, about 1 gram of such molecules to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits. Molecules of Formula One may be applied with one or more active ingredients in a soil amendment.

Molecules of Formula One may be used for controlling endoparasites and ectoparasites in the veterinary medicine sector or in the field of non-human-animal keeping. Such molecules may be applied by oral administration in the form of, for example, tablets, capsules, drinks, granules, by dermal application in the form of, for example, dipping, spraying, pouring on, spotting on, and dusting, and by parenteral administration in the form of, for example, an injection.

Molecules of Formula One may also be employed advantageously in livestock keeping, for example, cattle, chickens, geese, goats, pigs, sheep, and turkeys. They may also be employed advantageously in pets such as, horses, dogs, and cats. Particular pests to control would be flies, fleas, and ticks that are bothersome to such animals. Suitable formulations are administered orally to the animals with the drinking water or feed. The dosages and formulations that are suitable depend on the species.

Molecules of Formula One may also be used for controlling parasitic worms, especially of the intestine, in the animals listed above.

Molecules of Formula One may also be employed in therapeutic methods for human health care. Such methods include, but are limited to, oral administration in the form of, for example, tablets, capsules, drinks, granules, and by dermal application.

Molecules of Formula One may also be applied to invasive pests. Pests around the world have been migrating to new environments (for such pest) and thereafter becoming a new invasive species in such new environment. Such molecules may also be used on such new invasive species to control them in such new environments.

Before a pesticide may be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

Molecules according to Formula One may be tested to determine its efficacy against pests. Additionally, a molecule of Formula One may be mixed with another active ingredient to form a pesticidal composition, and then that composition is tested to determine if it is synergistic using conventional testing procedures. Furthermore, mode of action studies may be conducted to determine if said molecule has a different mode of action than other pesticides. Thereafter, such acquired data may be disseminated, such as by the internet, to third parties.

The headings in this document are for convenience only and must not be used to interpret any portion hereof.

Tables

TABLE B

| Weight Ratios Molecule of the Formula One: active ingredient |
|---|
| 100:1 to 1:100 |
| 50:1 to 1:50 |
| 20:1 to 1:20 |
| 10:1 to 1:10 |
| 5:1 to 1:5 |
| 3:1 to 1:3 |
| 2:1 to 1:2 |
| 1:1 |

TABLE C

| | | molecule of Formula One (X) Parts by weight | | | | | | | | |
|---|---|---|---|---|---|---|---|---|---|---|
| | | 1 | 2 | 3 | 5 | 10 | 15 | 20 | 50 | 100 |
| active ingredient | 100 | X,Y | | X,Y | | | X,Y | | | |
| (Y) Parts by weight | 50 | X,Y | X,Y | X,Y | | | X,Y | X,Y | | |
| | 20 | X,Y | | X,Y | X,Y | | X,Y | | X,Y | |
| | 15 | X,Y | X,Y | | | | | X,Y | X,Y | X,Y |
| | 10 | X,Y | | X,Y | | | | | | |
| | 5 | X,Y | X,Y | X,Y | | | | X,Y | | |
| | 3 | X,Y | X,Y | | X,Y | X,Y | | X,Y | X,Y | X,Y |
| | 2 | X,Y | | X,Y | X,Y | | X,Y | | X,Y | |
| | 1 | X,Y | X,Y | X,Y | X,Y | X,Y | X,Y | X,Y | X,Y | X,Y |

TABLE 2
Structure and preparation method for F Series molecules
| No. | Structure | Prep.* |
|---|---|---|
| F1 | 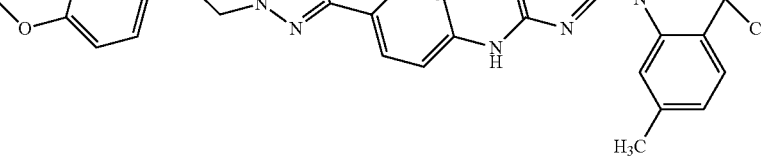 | 3 |
| F2 | 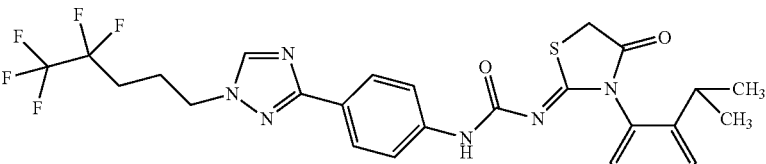 | 8 |
| F3 | 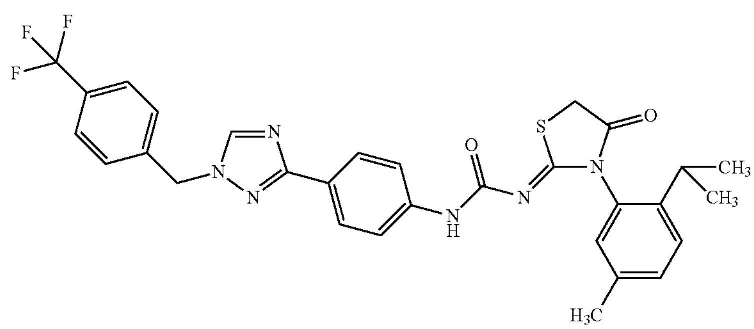 [SMILES: Cc1ccc(C(C)C)c(N2C(=O)CS/C2=N\C(=O)Nc2ccc(-c3ncn(Cc4ccc(C(F)(F)F)cc4)n3)cc2)c1] | 8 |
| F4 | 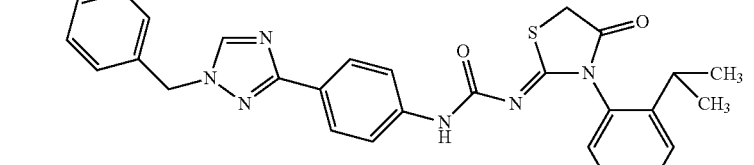 | 8 |
| F5 | 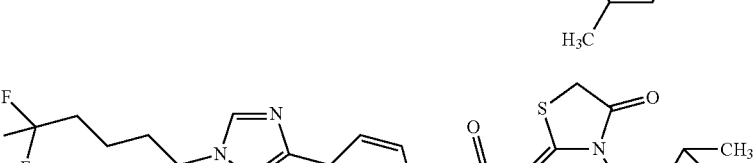 | 9 |
| F6 | 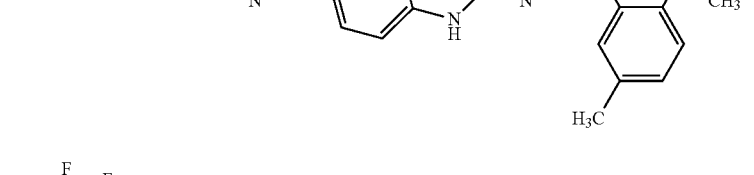 | 8 |
*prepared according to example number

TABLE 3

Structure and preparation method for C series molecules

| No. | Structure | Prep* |
|---|---|---|
| C1 | (structure) | 1 |
| C2 | (structure) | 2 |
| C3 | (structure) | 4 |
| C4 | (structure) | 4 |
| C5 | (structure) | 4 |
| C6 | (structure) | 4 |
| C7 | (structure) | 4 |
| C8 | (structure) | 5 |
| C9 | (structure) | 5 |

TABLE 3-continued
Structure and preparation method for C series molecules
| No. | Structure | Prep* |
|---|---|---|
| C10 | 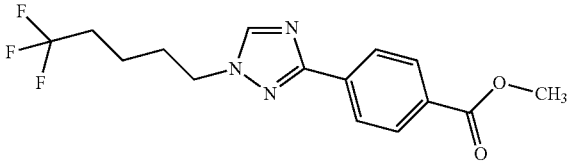 [SMILES: COC(=O)c1ccc(-c2ncn(CCCCC(F)(F)F)n2)cc1] | 5 |
| C11 | 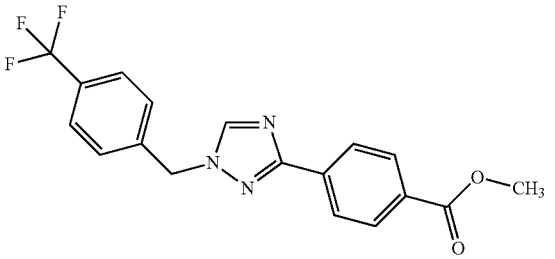 [SMILES: COC(=O)c1ccc(-c2ncn(Cc3ccc(C(F)(F)F)cc3)n2)cc1] | 5 |
| C12 | 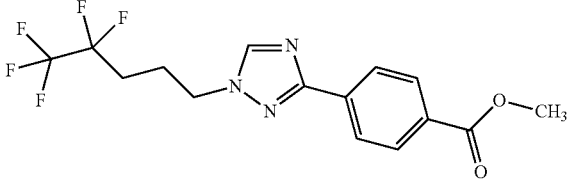 [SMILES: COC(=O)c1ccc(-c2ncn(CCCC(F)(F)C(F)(F)F)n2)cc1] | 5 |
| C13 | 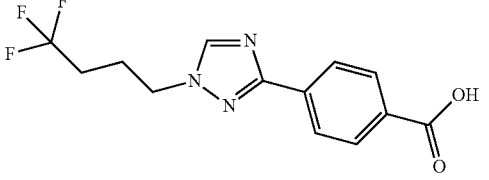 | 6 |
| C14 | 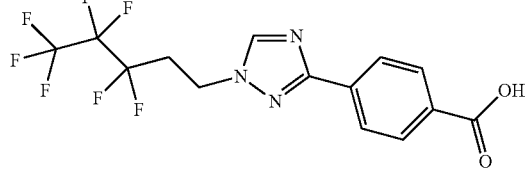 | 6 |
| C15 | 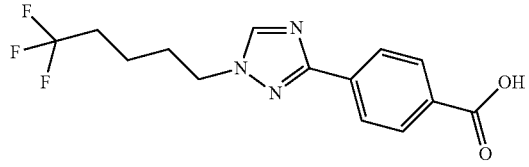 [SMILES: O=C(O)c1ccc(-c2ncn(CCCCC(F)(F)F)n2)cc1] | 6 |
| C16 | 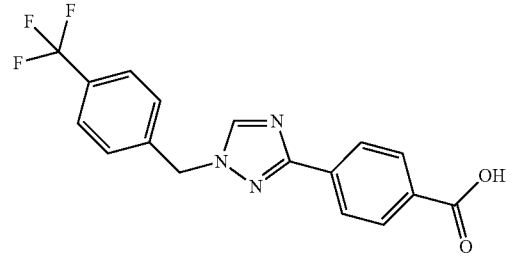 [SMILES: O=C(O)c1ccc(-c2ncn(Cc3ccc(C(F)(F)F)cc3)n2)cc1] | 6 |

TABLE 3-continued
Structure and preparation method for C series molecules
| No. | Structure | Prep* |
|---|---|---|
| C17 | 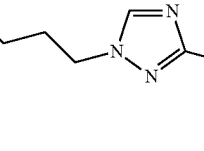 | 6 |
| C18 | 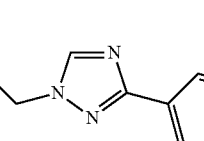 | 7 |
| C19 | 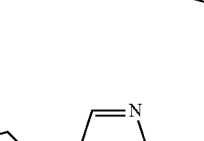 | 7 |
| C20 | 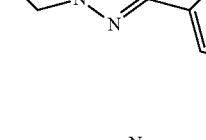 | 7 |
| C21 | 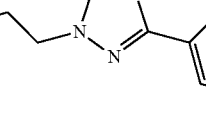 | 7 |
| C22 | 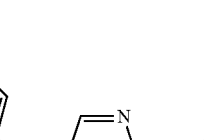 | 7 |
*prepared according to example number
TABLE 4
Analytical data for molecules in Table 2
| No. | Mp (° C.) | IR (cm$^{-1}$) | Mass (m/z) | $^1$H NMR | $^{13}$CNMR; $^{19}$F NMR |
|---|---|---|---|---|---|
| F1 | 202-204 | | ESIMS 623 ([M + H]$^+$) | (400 MHz, CDCl$_3$) δ 8.09-7.98 (m, 2H), 7.76 (s, 1H), 7.63-7.54 (m, 2H), 7.39 (d, J = 8.0 Hz, 1H), 7.35-7.29 (m, 2H), 7.11 (td, J = 8.8, 7.1 Hz, 4H), 6.91 (t, J = 1.4 Hz, 1H), 4.38 (t, J = 6.9 Hz, 2H), 3.98 (d, J = 3.0 Hz, 2H), 3.23 (t, J = 7.0 Hz, 2H), 2.68 (p, | $^{13}$C NMR (126 MHz, CDCl$_3$) δ 171.17, 152.71, 137.87, 135.50, 127.93, 118.59, 80.60, |

TABLE 4-continued

Analytical data for molecules in Table 2

| No. | Mp (° C.) | IR (cm$^{-1}$) | Mass (m/z) | $^1$H NMR | $^{13}$CNMR; $^{19}$F NMR |
|---|---|---|---|---|---|
| | | | | J = 6.8 Hz, 1H), 2.39 (s, 3H), 1.19 (t, J = 6.6 Hz, 6H) | 65.03, 60.41, 28.34, 21.06, 14.20; $^{19}$F NMR (376 MHz, CDCl$_3$) δ −57.91 |
| F2 | 190-192 | | ESIMS 581 ([M + H]$^+$) | (300 MHz, CDCl$_3$) δ 8.04 (d, J = 5.1 Hz, 2H), 8.00 (s, 1H), 7.57 (d, J = 8.4 Hz, 2H), 7.52-7.50 (m, 2H), 7.38-7.34 (m, 2H), 7.09 (d, J = 7.8 Hz, 1H), 4.27 (t, J = 6.6 Hz, 2H), 3.98 (s, 2H), 2.74-2.67 (m, 1H), 2.36-2.05 (m, 4H), 1.23-1.19 (m, 6H) | |
| F3 | 229-232 | | ESIMS 579 ([M + H]$^+$) | (400 MHz, CDCl$_3$) δ 8.10 (s, 1H), 8.03 (d, J = 8.8 Hz, 2H), 7.63 (d, J = 8.8 Hz, 2H), 7.56 (d, J = 8.8 Hz, 2H), 7.52-7.50 (m, 2H), 7.39 (d, J = 8.8 Hz, 2H), 7.38-7.36 (m, 1H), 7.58 (s, 1H), 7.09 (d, J = 8.0 Hz, 1H), 5.42 (s, 2H), 3.98 (d, J = 2.8 Hz, 2H), 2.74-2.70 (m, 1H), 1.22-1.20 (m, 6H) | |
| F4 | 202-206 | | ESIMS 545 ([M + H]$^+$) | (400 MHz, CDCl$_3$) δ 8.02 (m, 3H), 7.56 (d, J = 8.8 Hz, 2H), 7.54-7.50 (m, 2H), 7.38-7.34 (m, 1H), 7.33 (s, 1H), 7.09 (d, J = 8.0 Hz, 1H), 4.20 (t, J = 7.2 Hz, 2H), 3.98 (d, J = 2.8 Hz, 2H), 2.74-2.68 (m, 1H), 2.17-2.00 (m, 4H), 1.66-1.54 (m, 2H), 1.22-1.20 (m, 6H) | |
| F5 | | | ESIMS 617 ([M + H]$^+$) | (400 MHz, CDCl$_3$) δ 8.09 (s, 1H), 8.02 (d, J = 8.4 Hz, 2H), 7.57 (d, J = 8.4 Hz, 2H), 7.52-7.49 (m, 2H), 7.38-7.34 (m, 1H), 7.30 (s, 1H), 7.09 (d, J = 8.0 Hz, 1H), 4.50 (t, J = 7.2 Hz, 2H), 3.98 (s, 2H), 2.86-2.70 (m, 3H), 1.22-1.20 (m, 6H) | |
| F6 | | | ESIMS 544 ([M + H]$^+$) | (400 MHz, CDCl$_3$) δ 8.05 (s, 1H), 8.02 (d, J = 8.7 Hz, 2H), 7.57 (d, J = 8.8 Hz, 2H), 7.37 (t, J = 8.4 Hz, 2H), 7.34-7.29 (m, 1H), 6.92-6.89 (m, 1H), 4.25 (t, J = 6.5 Hz, 2H), 3.97 (d, J = 3.0 Hz, 2H), 2.67 (p, J = 6.9 Hz, 1H), 2.38 (s, 3H), 2.28-2.18 (m, 4H), 1.19 (dd, J = 6.8, 5.9 Hz, 6H) | $^{13}$C NMR (101 MHz, CDCl$_3$) δ 172.95, 170.75, 163.18, 159.89, 144.30, 143.73, 139.39, 137.39, 132.94, 131.70, 129.32, 129.04, 127.55, 127.21, 126.88, 119.13, 48.56, 33.48, 31.39, 28.86, 24.27, 23.12, 21.29; $^{19}$F NMR (376 MHz, CDCl$_3$) δ −65.85 |

BAW & CL Rating Table

| % Control (or Mortality) | Rating |
|---|---|
| 50-100 | A |
| More than 0-Less than 50 | B |
| Not Tested | C |
| No activity noticed in this bioassay | D |

YFM Rating Table

| % Control (or Mortality) | Rating |
|---|---|
| 80-100 | A |
| More than 0-Less than 80 | B |
| Not Tested | C |
| No activity noticed in this bioassay | D |

TABLE ABC

Biological Results

| No. | Species | | |
|---|---|---|---|
| | BAW | CL | YFM |
| F1 | A | A | C |
| F2 | A | A | C |
| F3 | B | A | B |
| F4 | A | A | B |
| F5 | A | A | A |
| F6 | A | A | C |

The invention claimed is:

1. A molecule of the following formula

Formula One

L$^1$—Het—CH$_2$—Ar$^1$—N(R$^{15}$)—C(Q$^1$)=N—C$^x$(Q$^2$)(R$^{16}$)—N$^x$(L$^2$)(R$^{17}$)

wherein:
(A) L$^1$ is selected from the group consisting of (C$_1$-C$_4$)alkyl, (C$_1$-C$_4$)haloalkyl, (C$_3$-C$_8$)cycloalkyl, (C$_2$-C$_6$)alkenyl, (C$_2$-C$_6$)alkynyl, (C$_1$-C$_4$)alkyl-O—(C$_1$-C$_4$)alkyl, and (C$_1$-C$_4$)alkyl-N(R$^x$)—(C$_1$-C$_4$)alkyl, wherein each alkyl, haloalkyl, cycloalkyl, alkenyl, and alkynyl may be optionally substituted with one or more substituents independently selected from the group consisting of H, F, Cl, Br, I, CN, $NO_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, and $(C_2-C_6)$alkynyl, phenyl, furanyl, pyridazinyl, pyridyl, and thienyl;

wherein each phenyl, furanyl, pyridazinyl, pyridyl, and thienyl may be optionally substituted with one or more substituents independently selected from the group consisting of H, F, Cl, Br, I, CN, $NO_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, $C(O)$—$NR^xR^y$, $(C_1-C_4)$alkyl-$NR^xR^y$, $C(O)$—$(C_1-C_4)$alkyl, $C(O)O$—$(C_1-C_4)$alkyl, $C(O)$—$(C_1-C_4)$haloalkyl, $C(O)O$—$(C_1-C_4)$haloalkyl, $C(O)$—$(C_3-C_8)$cycloalkyl, $C(O)O$—$(C_3-C_8)$cycloalkyl, $C(O)$—$(C_2-C_6)$alkenyl, $C(O)O$—$(C_2-C_6)$alkenyl, $(C_1-C_4)$alkyl-O—$(C_1-C_4)$alkyl, $(C_1-C_4)$alkyl-$S(O)_n$—$(C_1-C_4)$alkyl, $C(O)$—$(C_1-C_4)$alkyl-$C(O)O$—$(C_1-C_4)$alkyl, phenyl, and phenoxy;

(B) Het is a 5- or 6-membered, saturated or unsaturated, heterocyclic ring, containing one or more heteroatoms independently selected from nitrogen, sulfur, or oxygen, and where $L^1$ and $Ar^1$ are not ortho to each other, but may be meta or para, such as, for a five-membered ring they are 1,3, and for a 6-membered ring they are either 1,3 or 1,4, wherein each heterocyclic ring may be optionally substituted with one or more substituents independently selected from the group consisting of H, F, Cl, Br, I, CN, $NO_2$, oxo, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, $C(O)$—$NR^xR^y$, $(C_1-C_4)$alkyl-$NR^xR^y$, $C(O)$—$(C_1-C_4)$alkyl, $C(O)O$—$(C_1-C_4)$alkyl, $C(O)$—$(C_1-C_4)$haloalkyl, $C(O)O$—$(C_1-C_4)$haloalkyl, $C(O)$—$(C_3-C_8)$cycloalkyl, $C(O)O$—$(C_3-C_8)$cycloalkyl, $C(O)$—$(C_2-C_6)$alkenyl, $C(O)O$—$(C_2-C_6)$alkenyl, $(C_1-C_4)$alkyl-O—$(C_1-C_4)$alkyl, $(C_1-C_4)$alkyl-$S(O)_n$—$(C_1-C_4)$alkyl, and $C(O)$—$(C_1-C_4)$alkyl-$C(O)O$—$(C_1-C_4)$alkyl, wherein each alkyl, haloalkyl, cycloalkyl, alkoxy, haloalkoxy, alkenyl, and alkynyl substituent may be optionally substituted with one or more substituents independently selected from the group consisting of H, F, Cl, Br, I, CN, $NO_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, $C(O)$—$NR^xR^y$, $(C_1-C_4)$alkyl-$NR^xR^y$, $C(O)$—$(C_1-C_4)$alkyl, $C(O)O$—$(C_1-C_4)$alkyl, $C(O)$—$(C_1-C_4)$haloalkyl, $C(O)O$—$(C_1-C_4)$haloalkyl, $C(O)$—$(C_3-C_8)$cycloalkyl, $C(O)O$—$(C_3-C_8)$cycloalkyl, $C(O)$—$(C_2-C_6)$alkenyl, $C(O)O$—$(C_2-C_6)$alkenyl, $(C_1-C_4)$alkyl-O—$(C_1-C_4)$alkyl, $(C_1-C_4)$alkyl-$S(O)_n$—$(C_1-C_4)$alkyl, $C(O)$—$(C_1-C_4)$alkyl-$C(O)O$—$(C_1-C_4)$alkyl, phenyl, and phenoxy;

(C) $Ar^1$ is selected from the group consisting of furanyl, phenyl, pyridazinyl, pyridyl, pyrimidinyl, and thienyl, wherein each furanyl, phenyl, pyridazinyl, pyridyl, pyrimidinyl, and thienyl may be optionally substituted with one or more substituents independently selected from the group consisting of H, F, Cl, Br, I, CN, $NO_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, $C(O)$—$NR^xR^y$, $(C_1-C_4)$alkyl-$NR^xR^y$, $C(O)$—$(C_1-C_4)$alkyl, $C(O)O$—$(C_1-C_4)$alkyl, $C(O)$—$(C_1-C_4)$haloalkyl, $C(O)O$—$(C_1-C_4)$haloalkyl, $C(O)$—$(C_3-C_8)$cycloalkyl, $C(O)O$—$(C_3-C_8)$cycloalkyl, $C(O)$—$(C_2-C_6)$alkenyl, $C(O)O$—$(C_2-C_6)$alkenyl, $(C_1-C_4)$alkyl-O—$(C_1-C_4)$alkyl, $(C_1-C_4)$alkyl-$S(O)_n$—$(C_1-C_4)$alkyl, $C(O)$—$(C_1-C_4)$alkyl-$C(O)O$—$(C_1-C_4)$alkyl, phenyl, and phenoxy, wherein each alkyl, haloalkyl, cycloalkyl, alkoxy, haloalkoxy, alkenyl, alkynyl, phenyl, and phenoxy substituent may be optionally substituted with one or more substituents independently selected from the group consisting of H, F, Cl, Br, I, CN, $NO_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_4)$alkyl, $S(O)_n$—$(C_1-C_4)$haloalkyl, $OSO_2$—$(C_1-C_4)$alkyl, $OSO_2$—$(C_1-C_4)$haloalkyl, $C(O)$—$NR^xR^y$, $(C_1-C_4)$alkyl-$NR^xR^y$, $C(O)$—$(C_1-C_4)$alkyl, $C(O)O$—$(C_1-C_4)$alkyl, $C(O)$—$(C_1-C_4)$haloalkyl, $C(O)O$—$(C_1-C_4)$haloalkyl, $C(O)$—$(C_3-C_8)$cycloalkyl, $C(O)O$—$(C_3-C_8)$cycloalkyl, $C(O)$—$(C_2-C_6)$alkenyl, $C(O)O$—$(C_2-C_6)$alkenyl, $(C_1-C_4)$alkyl-O—$(C_1-C_4)$alkyl, $(C_1-C_4)$alkyl-$S(O)_n$—$(C_1-C_4)$alkyl, $C(O)$—$(C_1-C_4)$alkyl-$C(O)O$—$(C_1-C_4)$alkyl, phenyl, and phenoxy;

(D) $R^{15}$ is selected from the group consisting of H, $(C_1-C_4)$alkyl, $(C_3-C_8)$cycloalkyl, $(C_2-C_6)$alkenyl, $(C_2-C_6)$alkynyl, $S(O)_n$—$(C_1-C_6)$alkyl, $C(O)$—$NR^xR^y$, $C(O)$-phenyl, $(C_1-C_6)$alkyl-$NR^xR^y$, $C(O)O$—$(C_1-C_6)$alkyl, $C(O)$—$(C_3-C_8)$cycloalkyl, $C(O)O$—$(C_3-C_8)$cycloalkyl, $C(O)$—$(C_2-C_6)$alkenyl, $C(O)O$—$(C_2-C_6)$alkenyl, $(C_1-C_4)$alkyl-O—$(C_1-C_4)$alkyl, $(C_1-C_4)$alkyl-$OC(O)$—$(C_1-C_4)$alkyl, $(C_1-C_4)$alkyl-$S(O)_n$—$(C_1-C_4)$alkyl, and $(C_1-C_4)$alkyl-$OC(O)O$—$(C_1-C_4)$alkyl, wherein each alkyl, cycloalkyl, alkenyl, alkynyl, and phenyl may be optionally substituted with one or more substituents independently selected from the group consisting of H, F, Cl, Br, I, CN, $NO_2$, oxo, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n$—$(C_1-C_6)$alkyl, $S(O)_n$—$(C_1-C_4)$haloalkyl, $OSO_2$—$(C_1-C_4)$alkyl, $OSO_2$—$(C_1-C_4)$haloalkyl, $C(O)$—$NR^xR^y$, $(C_1-C_4)$alkyl-$NR^xR^y$, $C(O)$—$(C_1-C_4)$alkyl, $C(O)O$—$(C_1-C_4)$alkyl, $C(O)$—$(C_1-C_4)$haloalkyl, $C(O)O$—$(C_1-C_4)$haloalkyl, $C(O)$—$(C_3-C_8)$cycloalkyl, $C(O)O$—$(C_3-C_8)$cycloalkyl, $C(O)$—$(C_2-C_6)$alkenyl, $C(O)O$—$(C_2-C_6)$alkenyl, $(C_1-C_4)$alkyl-O—$(C_1-C_4)$alkyl, $(C_1-C_4)$ alkyl-S(O)$_n$—(C$_1$-C$_4$)alkyl, C(O)—(C$_1$-C$_4$)alkyl-C(O)O—(C$_1$-C$_4$)alkyl, phenyl, and phenoxy;

(E) Q$^1$ is selected from the group consisting of O and S;

(F) Q$^2$ is selected from the group consisting of O and S;

(G) R$^{16}$ is selected from the group consisting of (J), H, (C$_1$-C$_4$)alkyl, (C$_3$-C$_8$)cycloalkyl, (C$_2$-C$_6$)alkenyl, (C$_2$-C$_6$)alkynyl, C(O)—(C$_1$-C$_4$)alkyl, (C$_1$-C$_4$)alkyl-O—(C$_1$-C$_4$)alkyl, (C$_1$-C$_4$)alkyl-S(O)$_n$—(C$_1$-C$_4$)alkyl, (C$_1$-C$_4$)alkylphenyl, (C$_1$-C$_4$)alkyl-O-phenyl, C(O)-(Het-1), Het-1, (C$_1$-C$_4$)alkyl-(Het-1), (C$_1$-C$_4$)alkyl-OC(O)—(C$_1$-C$_4$)alkyl, (C$_1$-C$_4$)alkyl-OC(O)—(C$_1$-C$_4$)alkyl, (C$_1$-C$_4$)alkyl-OC(O)O—(C$_1$-C$_4$)alkyl, (C$_1$-C$_4$)alkyl-OC(O)—NR$^x$R$^y$, (C$_1$-C$_4$)alkyl-C(O)—N(R$^x$)(C$_1$-C$_4$)alkyl-(Het-1), (C$_1$-C$_4$)alkyl-C(O)-(Het-1), (C$_1$-C$_4$)alkyl-C(O)—N(R$^x$)(C$_1$-C$_4$)alkyl(NR$^x$R$^y$)—C(O)OH, (C$_1$-C$_4$)alkyl-C(O)—N(R$^x$)(C$_1$-C$_4$)alkyl-NR$^x$R$^y$, (C$_1$-C$_4$)alkyl-C(O)—N(R$^x$)(C$_1$-C$_4$)alkyl-N(R$^x$)—C(O)O—(C$_1$-C$_4$)alkyl, (C$_1$-C$_4$)alkyl-C(O)—N(R$^x$)(C$_1$-C$_4$)alkyl(N(R$^x$)—C(O)O—(C$_1$-C$_4$)alkyl)-C(O)OH, (C$_1$-C$_4$)alkyl-C(O)-(Het-1)-C(O)O—(C$_1$-C$_4$)alkyl, (C$_1$-C$_4$)alkyl-OC(O)O—(C$_1$-C$_4$)alkyl, (C$_1$-C$_4$)alkyl-OC(O)—(C$_1$-C$_4$)alkyl, (C$_1$-C$_4$)alkyl-OC(O)—(C$_3$-C$_8$)cycloalkyl, (C$_1$-C$_4$)alkyl-OC(O)-(Het-1), (C$_1$-C$_4$)alkyl-OC(O)—(C$_1$-C$_4$)alkyl-N(R$^x$)—C(O)O—(C$_1$-C$_4$)alkyl, (C$_1$-C$_4$)alkyl-NR$^x$R$^y$, (C$_1$-C$_4$)alkyl-S(O)$_n$-(Het-1), and (C$_1$-C$_4$)alkyl-O-(Het-1), wherein each alkyl, cycloalkyl, alkenyl, alkynyl, phenyl, and (Het-1) may be optionally substituted with one or more substituents independently selected from the group consisting of H, F, Cl, Br, I, CN, NO$_2$, NR$^x$R$^y$, (C$_1$-C$_4$)alkyl, (C$_1$-C$_4$)haloalkyl, (C$_3$-C$_8$)cycloalkyl, (C$_1$-C$_4$)alkoxy, (C$_2$-C$_6$)alkenyl, (C$_2$-C$_6$)alkynyl, S(O)$_n$—(C$_1$-C$_4$)alkyl, S(O)$_n$—(C$_1$-C$_4$)haloalkyl, OSO$_2$—(C$_1$-C$_4$)alkyl, OSO$_2$—(C$_1$-C$_4$)haloalkyl, C(O)H, C(O)OH, C(O)—NR$^x$R$^y$, (C$_1$-C$_4$)alkyl-NR$^x$R$^y$, C(O)—(C$_1$-C$_4$)alkyl, C(O)O—(C$_1$-C$_4$)alkyl, C(O)—(C$_1$-C$_4$)haloalkyl, C(O)O—(C$_1$-C$_4$)haloalkyl, C(O)—(C$_3$-C$_8$)cycloalkyl, C(O)O—(C$_3$-C$_8$)cycloalkyl, C(O)—(C$_2$-C$_6$)alkenyl, C(O)O—(C$_2$-C$_6$)alkenyl, (C$_1$-C$_4$)alkyl-O—(C$_1$-C$_4$)alkyl, (C$_1$-C$_4$)alkyl-S(O)$_n$—(C$_1$-C$_4$)alkyl, C(O)—(C$_1$-C$_4$)alkyl-C(O)O—(C$_1$-C$_4$)alkyl), phenyl, phenoxy, Si((C$_1$-C$_4$)alkyl)$_3$, S(O)$_n$—NR$^x$R$^y$, and (Het-1);

(H) R$^{17}$ is selected from the group consisting of (J), H, (C$_1$-C$_4$)alkyl, (C$_3$-C$_8$)cycloalkyl, (C$_2$-C$_6$)alkenyl, (C$_2$-C$_6$)alkynyl, C(O)—(C$_1$-C$_4$)alkyl, (C$_1$-C$_4$)alkyl-O—(C$_1$-C$_4$)alkyl, (C$_1$-C$_4$)alkyl-S(O)$_n$—(C$_1$-C$_4$)alkyl, (C$_1$-C$_4$)alkylphenyl, (C$_1$-C$_4$)alkyl-O-phenyl, C(O)-(Het-1), Het-1, (C$_1$-C$_4$)alkyl-(Het-1), (C$_1$-C$_4$)alkyl-OC(O)—(C$_1$-C$_4$)alkyl, (C$_1$-C$_4$)alkyl-OC(O)—(C$_1$-C$_4$)alkyl, (C$_1$-C$_4$)alkyl-OC(O)O—(C$_1$-C$_4$)alkyl, (C$_1$-C$_4$)alkyl-OC(O)—NR$^x$R$^y$, (C$_1$-C$_4$)alkyl-C(O)—N(R$^x$)(C$_1$-C$_4$)alkyl-(Het-1), (C$_1$-C$_4$)alkyl-C(O)-(Het-1), (C$_1$-C$_4$)alkyl-C(O)—N(R$^x$)(C$_1$-C$_4$)alkyl(NR$^x$R$^y$)—C(O)OH, (C$_1$-C$_4$)alkyl-C(O)—N(R$^x$)(C$_1$-C$_4$)alkyl-NR$^x$R$^y$, (C$_1$-C$_4$)alkyl-C(O)—N(R$^x$)(C$_1$-C$_4$)alkyl-N(R$^x$)—C(O)O—(C$_1$-C$_4$)alkyl, (C$_1$-C$_4$)alkyl-C(O)—N(R$^x$)(C$_1$-C$_4$)alkyl(N(R$^x$)—C(O)O—(C$_1$-C$_4$)alkyl)-C(O)OH, (C$_1$-C$_4$)alkyl-C(O)-(Het-1)-C(O)O—(C$_1$-C$_4$)alkyl, (C$_1$-C$_4$)alkyl-OC(O)O—(C$_1$-C$_4$)alkyl, (C$_1$-C$_4$)alkyl-OC(O)—(C$_1$-C$_4$)alkyl, (C$_1$-C$_4$)alkyl-OC(O)—(C$_3$-C$_8$)cycloalkyl, (C$_1$-C$_4$)alkyl-OC(O)-(Het-1), (C$_1$-C$_4$)alkyl-OC(O)—(C$_1$-C$_4$)alkyl-N(R$^x$)—C(O)O—(C$_1$-C$_4$)alkyl, (C$_1$-C$_4$)alkyl-NR$^x$R$^y$, (C$_1$-C$_4$)alkyl-S(O)$_n$-(Het-1), and (C$_1$-C$_4$)alkyl-O-(Het-1), wherein each alkyl, cycloalkyl, alkenyl, alkynyl, phenyl, and (Het-1) may be optionally substituted with one or more substituents independently selected from the group consisting of H, F, Cl, Br, I, CN, NO$_2$, NR$^x$R$^y$, (C$_1$-C$_4$)alkyl, (C$_1$-C$_4$)haloalkyl, (C$_3$-C$_8$)cycloalkyl, (C$_1$-C$_4$)alkoxy, (C$_2$-C$_6$)alkenyl, (C$_2$-C$_6$)alkynyl, S(O)$_n$—(C$_1$-C$_4$)alkyl, S(O)$_n$—(C$_1$-C$_4$)haloalkyl, OSO$_2$—(C$_1$-C$_4$)alkyl, OSO$_2$—(C$_1$-C$_4$)haloalkyl, C(O)H, C(O)OH, C(O)—NR$^x$R$^y$, (C$_1$-C$_4$)alkyl-NR$^x$R$^y$, C(O)—(C$_1$-C$_4$)alkyl, C(O)O—(C$_1$-C$_4$)alkyl, C(O)—(C$_1$-C$_4$)haloalkyl, C(O)O—(C$_1$-C$_4$)haloalkyl, C(O)—(C$_3$-C$_8$)cycloalkyl, C(O)O—(C$_1$-C$_4$)cycloalkyl, C(O)—(C$_2$-C$_6$)alkenyl, C(O)O—(C$_2$-C$_6$)alkenyl, (C$_1$-C$_4$)alkyl-O—(C$_1$-C$_4$)alkyl, (C$_1$-C$_4$)alkyl-S(O)$_n$—(C$_1$-C$_4$)alkyl, C(O)—(C$_1$-C$_4$)alkyl-C(O)O—(C$_1$-C$_4$)alkyl, phenyl, phenoxy, Si((C$_1$-C$_4$)alkyl)$_3$, S(O)$_n$—NR$^x$R$^y$, and (Het-1);

(I) L$^2$ is selected from the group consisting of (C$_3$-C$_8$)cycloalkyl, phenyl, (C$_1$-C$_4$)alkylphenyl, (C$_1$-C$_4$)alkyl-O-phenyl, (C$_2$-C$_6$)alkenyl-O-phenyl, (Het-1), (C$_1$-C$_4$)alkyl-(Het-1), and (C$_1$-C$_4$)alkyl-O-(Het-1), wherein each alkyl, cycloalkyl, alkenyl, phenyl, and (Het-1) may be optionally substituted with one or more substituents independently selected from the group consisting of H, F, Cl, Br, I, CN, NO$_2$, NR$^x$R$^y$, (C$_1$-C$_4$)alkyl, (C$_1$-C$_4$)haloalkyl, (C$_3$-C$_8$)cycloalkyl, (C$_1$-C$_4$)alkoxy, (C$_1$-C$_4$)haloalkoxy, (C$_2$-C$_6$)alkenyl, (C$_2$-C$_6$)alkynyl, S(O)$_n$—(C$_1$-C$_4$)alkyl, S(O)$_n$—(C$_1$-C$_4$)haloalkyl, OSO$_2$—(C$_1$-C$_4$)alkyl, OSO$_2$—(C$_1$-C$_4$)haloalkyl, C(O)H, C(O)—NR$^x$R$^y$, (C$_1$-C$_4$)alkyl-NR$^x$R$^y$, C(O)—(C$_1$-C$_4$)alkyl, C(O)O—(C$_1$-C$_4$)alkyl, C(O)—(C$_1$-C$_4$)haloalkyl, C(O)O—(C$_1$-C$_4$)haloalkyl, C(O)—(C$_3$-C$_8$)cycloalkyl, C(O)O—(C$_1$-C$_4$)cycloalkyl, C(O)—(C$_2$-C$_6$)alkenyl, C(O)O—(C$_2$-C$_6$)alkenyl, O—(C$_1$-C$_4$)alkyl, S—(C$_1$-C$_4$)alkyl, (C$_1$-C$_4$)alkyl-O—(C$_1$-C$_4$)alkyl, C(O)—(C$_1$-C$_4$)alkyl-C(O)O—(C$_1$-C$_4$)alkyl, phenyl, phenoxy, and (Het-1), wherein each alkyl, cycloalkyl, alkenyl, phenyl, and (Het-1) substituent may be optionally substituted with one or more substituents independently selected from the group consisting of H, F, Cl, Br, I, CN, NO$_2$, NR$^x$R$^y$, (C$_1$-C$_4$)alkyl, (C$_1$-C$_4$)haloalkyl, (C$_3$-C$_8$)cycloalkyl, (C$_1$-C$_4$)alkoxy, (C$_1$-C$_4$)haloalkoxy, (C$_2$-C$_6$)alkenyl, (C$_2$-C$_6$)alkynyl, S(O)$_n$—(C$_1$-C$_4$)alkyl, S(O)$_n$—(C$_1$-C$_4$)haloalkyl, OSO$_2$—(C$_1$-C$_4$)alkyl, OSO$_2$—(C$_1$-C$_4$)haloalkyl, C(O)H, C(O)—NR$^x$R$^y$, (C$_1$-C$_4$)alkyl-NR$^x$R$^y$, C(O)—(C$_1$-C$_4$)alkyl, C(O)O—(C$_1$-C$_4$)alkyl, C(O)—(C$_1$-C$_4$)haloalkyl, C(O)O—(C$_1$-C$_4$)haloalkyl, C(O)—(C$_3$-C$_8$)cycloalkyl, C(O)O—(C$_1$-C$_4$)cycloalkyl, C(O)—(C$_2$-C$_6$)alkenyl, C(O)O—(C$_2$-C$_6$)alkenyl, O—(C$_1$-C$_4$)alkyl, S—(C$_1$-C$_4$)alkyl, (C$_1$-C$_4$)alkyl-O—(C$_1$-C$_4$)alkyl, C(O)—(C$_1$-C$_4$)alkyl-C(O)O—(C$_1$-C$_4$)alkyl, phenyl, phenoxy, and (Het-1);

(J) R$^{16}$ and R$^{17}$ along with C$^x$(Q$^2$)(N$^x$), form a 4- to 7-membered saturated or unsaturated, hydrocarbyl cyclic group, which may further contain one or more heteroatoms selected from the group consisting of nitrogen, sulfur, and oxygen, wherein said hydrocarbyl cyclic group may be optionally substituted with one or more substituents independently selected from the group consisting of oxo, $R^{18}$, and $R^{19}$, wherein $R^{18}$ and $R^{19}$ are each independently selected from the group consisting of H, F, Cl, Br, I, CN, $NO_2$, oxo, thioxo, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n-(C_1-C_4)$alkyl, $S(O)_n-(C_1-C_4)$haloalkyl, $OSO_2-(C_1-C_4)$alkyl, $OSO_2-(C_1-C_4)$haloalkyl, C(O)H, $C(O)-(C_1-C_4)$alkyl, $C(O)O-(C_1-C_4)$alkyl, $C(O)-(C_1-C_4)$haloalkyl, $C(O)O-(C_1-C_4)$haloalkyl, $C(O)-(C_3-C_8)$cycloalkyl, $C(O)O-(C_3-C_8)$cycloalkyl, $C(O)-(C_2-C_6)$alkenyl, $C(O)O-(C_2-C_6)$alkenyl, $(C_1-C_4)$alkyl-O-$(C_1-C_4)$alkyl, $(C_1-C_4)$alkyl-$S(O)_n-(C_1-C_4)$alkyl, $C(O)-(C_1-C_4)$alkyl-$C(O)O-(C_1-C_4)$alkyl, phenyl, and (Het-1);

(K) $R^x$ and $R^y$ are each independently selected from the group consisting of H, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n-(C_1-C_4)$alkyl, $S(O)_n-(C_1-C_4)$haloalkyl, $OSO_2-(C_1-C_4)$alkyl, $OSO_2-(C_1-C_4)$haloalkyl, C(O)H, $C(O)-(C_1-C_4)$alkyl, $C(O)O-(C_1-C_4)$alkyl, $C(O)-(C_1-C_4)$haloalkyl, $C(O)O-(C_1-C_4)$haloalkyl, $C(O)-(C_3-C_8)$cycloalkyl, $C(O)O-(C_3-C_8)$cycloalkyl, $C(O)-(C_2-C_6)$alkenyl, $C(O)O-(C_2-C_6)$alkenyl, $(C_1-C_4)$alkyl-O-$(C_1-C_4)$alkyl, $(C_1-C_4)$alkyl-$S(O)_n-(C_1-C_4)$alkyl, $C(O)-(C_1-C_4)$alkyl-$C(O)O-(C_1-C_4)$alkyl, and phenyl, wherein each alkyl, haloalkyl, cycloalkyl, alkoxy, haloalkoxy, alkenyl, alkynyl, and phenyl may be optionally substituted with one or more substituents independently selected from the group consisting of H, F, Cl, Br, I, CN, $NO_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n-(C_1-C_4)$alkyl, $S(O)_n-(C_1-C_4)$haloalkyl, $OSO_2-(C_1-C_4)$alkyl, $OSO_2-(C_1-C_4)$haloalkyl, C(O)H, $C(O)-(C_1-C_4)$alkyl, $C(O)O-(C_1-C_4)$alkyl, $C(O)-(C_1-C_4)$haloalkyl, $C(O)O-(C_1-C_4)$haloalkyl, $C(O)-(C_3-C_8)$cycloalkyl, $C(O)O-(C_3-C_8)$cycloalkyl, $C(O)-(C_2-C_6)$alkenyl, $C(O)O-(C_2-C_6)$alkenyl, $(C_1-C_4)$alkyl-O-$(C_1-C_4)$alkyl, $(C_1-C_4)$alkyl-$S(O)_n-(C_1-C_4)$alkyl, $C(O)-(C_1-C_4)$alkyl-$C(O)O-(C_1-C_4)$alkyl, phenyl, and (Het-1);

(L) (Het-1) is a 5- or 6-membered, saturated or unsaturated, heterocyclic ring, containing one or more heteroatoms independently selected from nitrogen, sulfur, or oxygen, wherein each heterocyclic ring may be optionally substituted with one or more substituents independently selected from the group consisting of H, F, Cl, Br, I, CN, $NO_2$, oxo, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n-(C_1-C_4)$alkyl, $S(O)_n-(C_1-C_4)$haloalkyl, $OSO_2-(C_1-C_4)$alkyl, $OSO_2-(C_1-C_4)$haloalkyl, $C(O)-NR^xR^y$, $(C_1-C_4)$alkyl-$NR^xR^y$, $C(O)-(C_1-C4)$alkyl, $C(O)O-(C_1-C_4)$alkyl, $C(O)-(C_1-C_4)$haloalkyl, $C(O)O-(C_1-C_4)$haloalkyl, $C(O)-(C_3-C_8)$cycloalkyl, $C(O)O-(C_3-C_8)$cycloalkyl, $C(O)-(C_2-C_6)$alkenyl, $C(O)O-(C_2-C_6)$alkenyl, $(C_1-C_4)$alkyl-O-$(C_1-C_4)$alkyl, $(C_1-C_4)$alkyl-$S(O)_n-(C_1-C_4)$alkyl, $C(O)-(C_1-C_4)$alkyl-$C(O)O-(C_1-C_4)$alkyl, phenyl, and phenoxy, wherein each alkyl, haloalkyl, cycloalkyl, alkoxy, haloalkoxy, alkenyl, alkynyl, phenyl, and phenoxy substituent may be optionally substituted with one or more substituents independently selected from the group consisting of H, F, Cl, Br, I, CN, $NO_2$, $(C_1-C_4)$alkyl, $(C_1-C_4)$haloalkyl, $(C_3-C_8)$cycloalkyl, $(C_1-C_4)$alkoxy, $(C_1-C_4)$haloalkoxy, $(C_2-C_6)$alkenyl, $(C_2-C_6)$alkynyl, $S(O)_n-(C_1-C_4)$alkyl, $S(O)_n-(C_1-C_4)$haloalkyl, $OSO_2-(C_1-C_4)$alkyl, $OSO_2-(C_1-C_4)$haloalkyl, $C(O)-NR^xR^y$, $(C_1-C_4)$alkyl-$NR^xR^y$, $C(O)-(C_1-C_4)$alkyl, $C(O)O-(C_1-C_4)$alkyl, $C(O)-(C_1-C_4)$haloalkyl, $C(O)O-(C_1-C_4)$haloalkyl, $C(O)-(C_3-C_8)$cycloalkyl, $C(O)O-(C_3-C_8)$cycloalkyl, $C(O)-(C_2-C_6)$alkenyl, $C(O)O-(C_2-C_6)$alkenyl, $(C_1-C_4)$alkyl-O-$(C_1-C_4)$alkyl, $(C_1-C_4)$alkyl-$S(O)_n-(C_1-C_4)$alkyl, $C(O)-(C_1-C_4)$alkyl-$C(O)O-(C_1-C_4)$alkyl, phenyl, and phenoxy;

(M) n are each independently 0, 1, or 2; and N-oxides, agriculturally acceptable acid addition salts, solvates, crystal polymorphs, isotopes, resolved stereoisomers, and tautomers, of the molecules of Formula One.

2. A molecule according to claim 1, wherein $L^1$ is selected from the group consisting of,

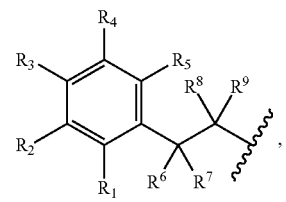

(1a)

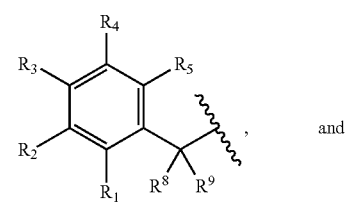

(1b)

and

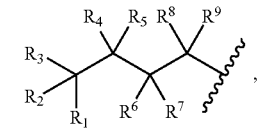

(1c)

wherein, $R^1$, $R^2$, $R^3$, $R^4$, $R^5$, $R^6$, $R^7$, $R^8$, $R^9$ are each one or more substituents independently selected from the group consisting of H, F, $CF_3$, and $OCF_3$.

3. A molecule according to claim 1, wherein Het is (1d)

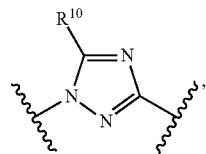
(1d)

wherein, $R^{10}$ is H.

4. A molecule according to claim 1, wherein $Ar^1$ is (1e)

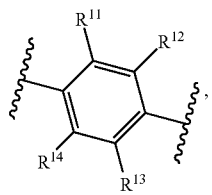
(1e)

wherein, $R^{11}$, $R^{12}$, $R^{13}$, and $R^{14}$ are each independently H.

5. A molecule according to claim 1, wherein $R^{15}$ is H.

6. A molecule according to claim 1, wherein $Q^1$ is O.

7. A molecule according to claim 1, wherein $Q^2$ is S.

8. A molecule according to claim 1, wherein $L^2$ is (1f)

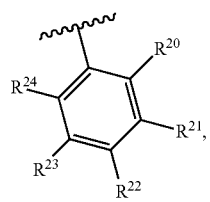
(1f)

wherein:

(1) $R^{20}$ is $CH(CH_3)_2$;

(2) $R^{21}$, $R^{22}$, and $R^{24}$ are each independently H; and (3) $R^{23}$ is $CH_3$.

9. A molecule according to claim 1, wherein $R^{16}$ and $R^{17}$ along with $C^x(Q^2)(N^x)$, is (1g)

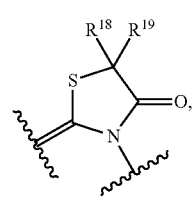
(1g)

wherein, $R^{18}$ and $R^{19}$ are each independently H.

10. A molecule according to claim 1, wherein (A) $L^1$ is selected from the group consisting of

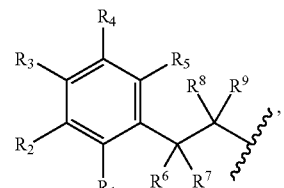
(1a)

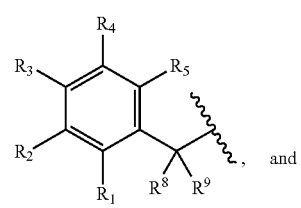
(1b)
and

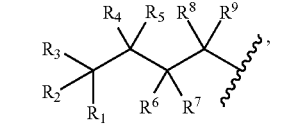
(1c)

wherein, $R^1$, $R^2$, $R^3$, $R^4$, $R^5$, $R^6$, $R^7$, $R^8$, $R^9$ are each independently selected from the group consisting of H, F, $(C_1-C_4)$haloalkyl, and $(C_1-C_4)$haloalkoxy;

(B) Het is (1d)

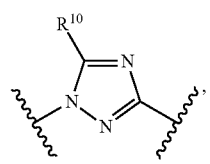
(1d)

wherein, $R^{10}$ is H;

(C) $Ar^1$ is (1e)

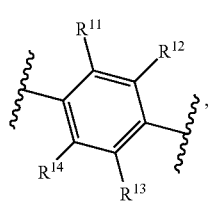
(1e)

wherein, $R^{11}$, $R^{12}$, $R^{13}$, and $R^{14}$ are each independently H;

(D) $R^{15}$ is H;

(E) $Q^1$ is O;

(F) $Q^2$ is S;

(G) $R^{16}$ is (J);

(H) $R^{17}$ is (J);

(I) $L^2$ is (1f)

(B) Het is (1d)

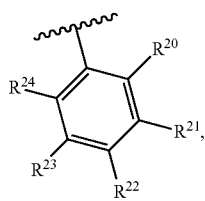

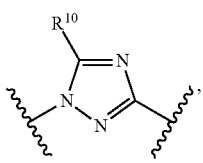

wherein, $R^{20}$, $R^{21}$, $R^{22}$, $R^{23}$, and $R^{24}$ are each independently selected from the group consisting of H and $(C_1-C_4)$alkyl; and wherein, $R^{10}$ is H;

(C) $Ar^1$ is (1e)

(J) $R^{16}$ and $R^{17}$ along with $C^x(Q^2)(N^x)$, is (1g)

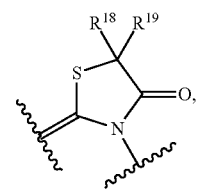

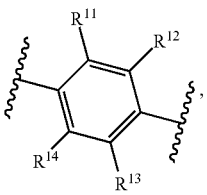

wherein, $R^{18}$ and $R^{19}$ are each independently H.

11. A molecule according to claim 1, wherein (A) $L^1$ is selected from the group consisting of wherein, $R^{11}$, $R^{12}$, $R^{13}$, and $R^{14}$ are each independently H;

(D) $R^{15}$ is H;

(E) $Q^1$ is O;

(F) $Q^2$ is S;

(G) $R^{16}$ is (J);

(H) $R^{17}$ is (J);

(I) $L^2$ is (1f)

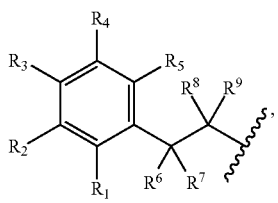

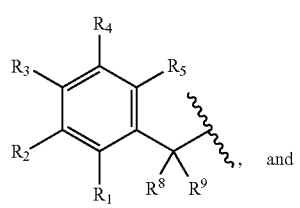

and

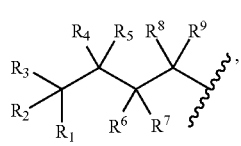

wherein, $R^{20}$, $R^{21}$, $R^{22}$, $R^{23}$, and $R^{24}$ are each independently selected from the group consisting of H, $CH_3$, and $CH(CH_3)_2$; and (J) $R^{16}$ and $R^{17}$ along with $C^x(Q^2)(N^x)$, is (1g)

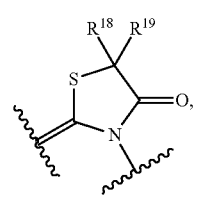

wherein, $R^1$, $R^2$, $R^3$, $R^4$, $R^5$, $R^6$, $R^7$, $R^8$, $R^9$ are each independently selected from the group consisting of H, F, $CF_3$, and $OCF_3$;

wherein, $R^{18}$ and $R^{19}$ are each independently H.

12. A molecule according to claim 1 wherein said molecule is selected from one of the following molecules

| No. | Structure |
|---|---|
| F1 | 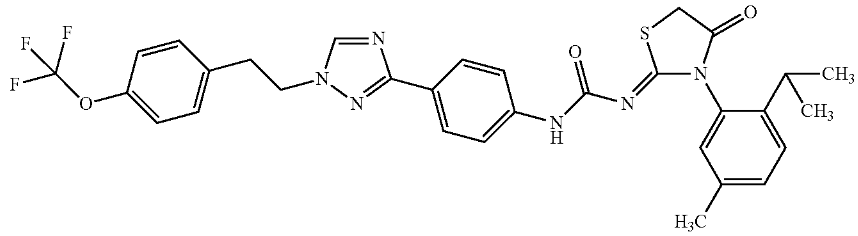 [SMILES: Cc1ccc(C(C)C)c(N2C(=O)CS/C2=N\C(=O)Nc2ccc(-c3ncn(CCc4ccc(OC(F)(F)F)cc4)n3)cc2)c1] |
| F2 | 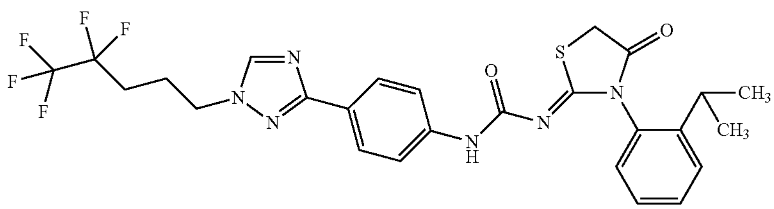 [SMILES: CC(C)c1ccccc1N1C(=O)CS/C1=N\C(=O)Nc1ccc(-c2ncn(CCCC(F)(F)C(F)(F)F)n2)cc1] |
| F3 | 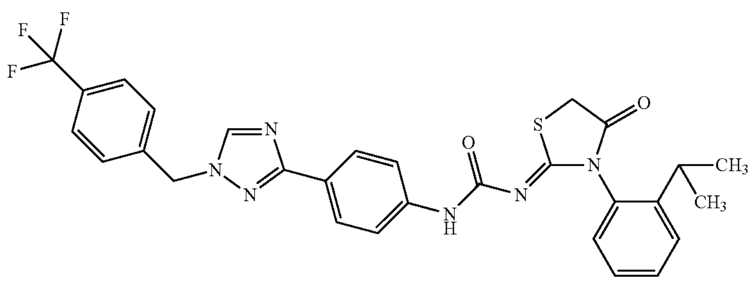 [SMILES: CC(C)c1ccccc1N1C(=O)CS/C1=N\C(=O)Nc1ccc(-c2ncn(Cc3ccc(C(F)(F)F)cc3)n2)cc1] |
| F4 | 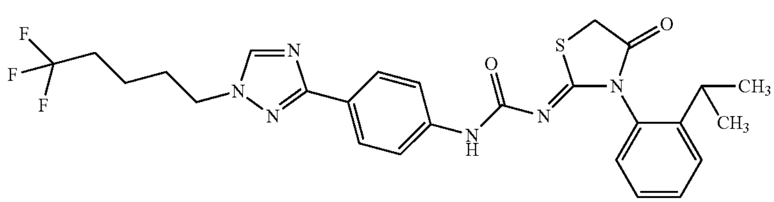 [SMILES: CC(C)c1ccccc1N1C(=O)CS/C1=N\C(=O)Nc1ccc(-c2ncn(CCCCC(F)(F)F)n2)cc1] |
| F5 | and |
| F6 | 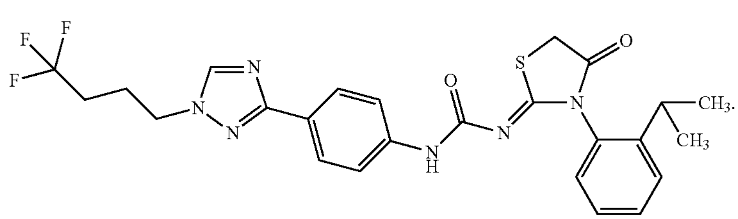 [SMILES: CC(C)c1ccccc1N1C(=O)CS/C1=N\C(=O)Nc1ccc(-c2ncn(CCCC(F)(F)F)n2)cc1] |

13. A pesticidal composition comprising (a) a molecule according to claim 1 and
(b) an active ingredient.

14. A process to control a pest said process comprising applying to a locus, a pesticidally effective amount of a molecule according to claim 1.

* * * * *